United States Patent
Kaplan et al.

(10) Patent No.: US 9,603,243 B2
(45) Date of Patent: Mar. 21, 2017

(54) SILK ELECTRONIC COMPONENTS

(75) Inventors: David Kaplan, Concord, MA (US);
Fiorenzo Omenetto, Wakefield, MA (US); Hu Tao, Medford, MA (US);
Richard Averitt, Newton, MA (US);
Andrew Strikwerda, Jamaica Plain, MA (US); Xin Zhang, Medford, MA (US); Konstantinos Tsioris, Somerville, MA (US)

(73) Assignees: TUFTS UNIVERSITY, Medford, MA (US); TRUSTEES OF BOSTON UNIVERSITY, Boston, MA (US)

( * ) Notice: Subject to any disclaimer, the term of this patent is extended or adjusted under 35 U.S.C. 154(b) by 734 days.

(21) Appl. No.: 13/641,000

(22) PCT Filed: Apr. 12, 2011

(86) PCT No.: PCT/US2011/032195
§ 371 (c)(1),
(2), (4) Date: Jun. 3, 2013

(87) PCT Pub. No.: WO2011/130335
PCT Pub. Date: Oct. 20, 2011

(65) Prior Publication Data
US 2013/0240251 A1    Sep. 19, 2013

Related U.S. Application Data

(60) Provisional application No. 61/323,172, filed on Apr. 12, 2010, provisional application No. 61/325,593, (Continued)

(51) Int. Cl.
*H05K 1/03* (2006.01)
*H01Q 7/00* (2006.01)
*G02B 1/00* (2006.01)

(52) U.S. Cl.
CPC ............... *H05K 1/032* (2013.01); *H01Q 7/00* (2013.01); *G02B 1/002* (2013.01)

(58) Field of Classification Search
CPC ........................................................ H01Q 7/00
See application file for complete search history.

(56) References Cited

U.S. PATENT DOCUMENTS 2,575,152 A * 11/1951 Whitner .................... D01F 4/00
106/157.9
5,245,012 A    9/1993 Lombari et al.
(Continued)

FOREIGN PATENT DOCUMENTS

| CN | 1329721 A | 1/2002 |
| CN | 2870195 Y | 2/2007 |

(Continued)

OTHER PUBLICATIONS

"Determination of silver nanoparticle release from antibacterial fabrics into artificial sweat," Kulthong et al., Particle and Fiber Toxicology, 2010, 7:8.*

(Continued)

*Primary Examiner* — Ian Rummel
(74) *Attorney, Agent, or Firm* — Choate, Hall & Stewart, LLP

(57) ABSTRACT

The invention relates to silk electronic components and methods for fabricating the same. The silk electronic components can be used as novel devices, such as implantable bioelectric and/or biophotonic devices, biosensors, surveillance devices, invisible cloaks, electromagnetic concentrators or antennas.

27 Claims, 21 Drawing Sheets

Related U.S. Application Data filed on Apr. 19, 2010, provisional application No. 61/446,158, filed on Feb. 24, 2011.

(56) References Cited

U.S. PATENT DOCUMENTS

| | | | |
|---|---|---|---|
| 6,902,932 | B2 | 6/2005 | Altman et al. |
| 7,841,863 | B2 | 11/2010 | Mathieu et al. |
| 8,206,774 | B2 | 6/2012 | Kaplan et al. |
| 8,666,471 | B2 | 3/2014 | Rogers et al. |
| 2004/0001299 | A1 | 1/2004 | van Haaster et al. |
| 2004/0005418 | A1* | 1/2004 | Schmid ............... B32B 15/20 428/34.1 |
| 2005/0260706 | A1 | 11/2005 | Kaplan et al. |
| 2006/0042822 | A1 | 3/2006 | Azeyanagi et al. |
| 2007/0007661 | A1 | 1/2007 | Burgess et al. |
| 2008/0197144 | A1* | 8/2008 | Rodgers ............... G06K 19/073 222/1 |
| 2009/0051071 | A1 | 2/2009 | Tamada et al. |
| 2009/0262766 | A1 | 10/2009 | Chen et al. |
| 2011/0227046 | A1 | 9/2011 | Hwang et al. |

FOREIGN PATENT DOCUMENTS

| | | |
|---|---|---|
| JP | 2007-520369 A | 7/2007 |
| JP | 2010-503238 A | 1/2010 |
| JP | 2010-508852 A | 3/2010 |
| JP | 2011-199254 A | 10/2011 |
| WO | WO-97/08315 A1 | 3/1997 |
| WO | WO-03/056297 A2 | 7/2003 |
| WO | WO-2004/062697 A2 | 7/2004 |
| WO | WO-2004/080346 A2 | 9/2004 |
| WO | WO-2005/000483 A1 | 1/2005 |
| WO | WO-2005/012606 A2 | 2/2005 |
| WO | WO-2005/123114 A2 | 12/2005 |
| WO | WO-2006/101223 A1 | 9/2006 |
| WO | WO-2007/016524 A2 | 2/2007 |
| WO | WO-2008/030960 A2 | 3/2008 |
| WO | WO-2008/118133 A2 | 10/2008 |
| WO | WO-2008/127401 A2 | 10/2008 |
| WO | WO-2008/127402 A2 | 10/2008 |
| WO | WO-2008/127403 A2 | 10/2008 |
| WO | WO-2008/137703 A1 | 11/2008 |
| WO | WO-2008/140562 A2 | 11/2008 |
| WO | WO-2008/150861 A1 | 12/2008 |
| WO | WO-2009/061823 A1 | 5/2009 |
| WO | WO-2010/057142 A2 | 5/2010 |
| WO | WO-2011/115643 A1 | 9/2011 |

OTHER PUBLICATIONS

U.S. Appl. No. 61/224,618, filed Jul. 10, 2009, Numata et al.
U.S. Appl. No. 61/227,254, filed Jul. 21, 2009, Kaplan et al.
Altman, G.H. et al., Silk-based biomaterials, Biomaterials, 24:401-416 (2003).
Amsden, J.J. et al., Spectral analysis of induced color change on periodically nanopatterned silk films, Opt. Express, 17(23):21271-9 (2009).
Apanius, M. et al., Silicon shadow mask fabrication for patterned metal deposition with microscale dimensions using a novel corner compensation scheme, Sensor Actuat. A: Phys., 140:168-175 (2007).
Asakura, T. et al., Comparative structure analysis of tyrosine and valine residues in unprocessed silk fibroin (silk I) and in the processed silk fiber (silk II) from Bombyx mori using solid-state (13)0,(15)N, and (2)H NMR, Biochemistry, 41(13):4415-24 (2002).
Ayub, Z. H. et al., Mechanism of the Gelation of Fibroin Solution, Viosci. Biotech. Biochem, 57(11):1910-1912 (1993).
Bain, C.D. et al., Formation of monolayer films by the spontaneous assembly of organic thiols from solution onto gold, J. Am. Chem. Soc., 111(1):321-335 (1989).
Barber, J. et al., Temperature-dependent far-infrared spectra of single crystals of high explosives using terahertz time-domain spectroscopy, J. Phys. Chem. A., 109(15):3501-5 (2005).
Bingham, C.M. et al, Planar wallpaper group metamaterials for novel terahertz applications, Opt. Express, 16(23):18565-75 (2008).
Bini, E. et al., Mapping domain structures in silks from insects and spiders related to protein assembly, Journal of Molecular Biology, 335(1):27-40 (2004).
Boccaccini, A.R. et al., Electrophoretic deposition of biomaterials, J. R. Soc. Interface, 7 Suppl 5:S581-613 (2010).
Chang et al., Porous Silk Scaffolds can be used for tissue engineering annulus fibrosus, Eur Spine J., 16:1848-1857 (2007).
Chen, H.T. et al., Active terahertz metamaterial devices, Nature, 444(7119):597-600 (2006).
Cheong, M. and Zhitomirsky, I., Electrodeposition of alginic acid and composite films, Colloids and Surfaces A: Physicochemical and Engineering Aspects, 328(1-3):73-78 (2008).
Cord, B et al., Robust shadow-mask evaporation via lithographically controlled undercut, J. Vac. Sci. Technol. B, 24(6):3139-3143 (2006).
Demura et al., Immobilization of peroxidase with a Bombyx mori silk fibroin membrane and its application to biophotosensors, J. Biotechnol., 10:113-120 (1989).
Demura, M. et al., Applications of 4M 14 silk fibroin enzyme immobilization material and the sensing function thereof, Polymer Reprints, Japan, 38(9): 3053-3055 (1989).
Dicko, C. et al., Spider silk protein refolding is controlled by changing pH 5, Biomacromolecules, 5(3):704-710 (2004).
Duvillaret et al., A Reliable Method for Extraction of Material Parameters in Terahertz Time-Domain Spectroscopy, IEEE J. Sel. Top. Quantum Electron, 2(3):739-746 (1996).
Extended European Search Report for EP 11769485.1, 6 pages (Oct. 23, 2013).
Foo, C. W. P., Role of pH and charge on silk protein assembly in insects and spiders, App. Phys. A, 82:223-233 (2006).
Forgotson, N. et al., Journal of Vacuum Science and Technology B: Microelectronics and Nanometer Structures, 14:732 (2009).
Frey-Wyssling, A., On the density and the optics of silk fibroin, Biochim. Biophys. Acta., 17(1):155-6 (1955).
Jiang, C. et al., Mechanical Properties of Robust Ultrathin Silk Fibroin Films, Advanced Functional Materials, 17: 2229-2237 (2007).
Jin, H.J. et al., Human bone marrow stromal cell responses on electrospun silk fibroin mats, Biomaterials, 25(6):1039-47 (2004).
Jin, I.J. et al., Water-Stable Silk Films with Reduced Beta-Sheet Content, Adv. Funct. Mater., 15:1241-1247 (2005).
Kang, D.J. et al., Well-Controlled Microcellular Biodegradable PLA/Silk Composite Foams Using Supercritical CO2, Macromol. Mater. Eng., 294: 620-624 (2009).
Kikuchi, Y. et al., Structure of the Bombyx mori fibroin light-chain-encoding gene: upstream sequence elements common to the light and heavy chain, Gene, 110(2):151-8 (1992).
Kim et al. Silicon Electronics on Silk as a Path to Bioresorbable, Implantable Devices, Appl. Phys. Lett. 95:133701-133703 (2009).
Kim, D.H. et al., Dissolvable films of silk fibroin for ultrathin conformal bio-integrated electronics, Nat. Mater., 9(6):511-517 (2010).
Kim, U. et al., Structure and Properties of Silk Hydrogels, Biomacromolecules, 5: 786-792 (2004).
Lawrence, B.D. et al., Bioactive silk protein biomaterial systems for optical devices, Biomacromolecules, 9:1214-1220 (2008).
Lei, M. et al., High-resolution technique for fabricating environmentally sensitive hydrogel microstructures, Langmuir, 20(21):8947-51 (2004).
Leisk, G.G. et al., Electrogelation for Protein Adhesives, Advanced Materials, 22:711-715 (2010).
Li, C. et al., Electrospun Silk-BMP-2 scaffolds for bone tissue engineering, Biomaterials, 27:3115-3124 (2006).
Li, X.G. et al., Conformational transition and liquid crystalline state of regenerated silk fibroin in water, Biopolymers, 89(6):497-505 (2008).
Liu, Y. et al., Biofabrication to build the biology-device interface, Biofabrication, 2(2):022002 (2010).
Lu, S. et al., Stabilization of Enzymes in Silk Films, Biomacromolecules, 10:1032-1042 (2009).

(56) References Cited

OTHER PUBLICATIONS

Lucas, F. et al., The silk fibroins, Advances in Protein Chemistry, 107-242 (1958).
Ma, R. et al., Electrodeposition of hyaluronic acid and hyaluronic acid-bovine serum albumin films from aqueous solutions, Colloids Surf. B Biointerfaces, 77(2):279-85 (2010).
Maniglio, D. et al., Electrodeposition of Silk Fibroin on Metal Substrates, Journal of Bioactive and Compatible Polymers, 25:441-454 (2010).
Murphy, A.R. et al., Modification of Silk Fibroin Using Diazonium Coupling Chemistry and the Effects on hMSC Proliferation and Differentiation, Biomaterials, 29(19):2829-2838 (2008).
Nagarkar, S. et al., Structure and gelation mechanism of silk hydrogels, Phys. Chem. Chem. Phys., 12(15):3834-44 (2010).
Nishizawa, S. et al., Terahertz Tim-Domain Spectroscopy, Terahertz Optoelectronics, Topics in Applied Physics, 97:203-270 (2005).
O'Hara, J.F. et al., Thin-film sensing with planar terahertz metamaterials: sensitivity and limitations, Opt. Express, 16(3):1786-95 (2008).
Omenetto, F. and Kaplan, D., A new route for silk, Nature Photonics, 2:641-643 (2008).
Omenetto, F.G. and Kaplan, D.L., New Opportunities for an Ancient Material, Science, 329:528-531 (2010).
Padilla, W.J. et al., Electrically resonant terahertz metamaterials: Theoretical and experimental investigations, Phys. Rev. B, 75:041102(R) (2007).
Padilla, W.J. et al., Negative refractive index materials, Materials Today, 9(7-8):28-34.
Parker et al., Biocompatible Silk Printed Optical Waveguides, Adv. Mater., 21:2411-2415 (2009).
Pendry, J.B. et al., Controlling electromagnetic fields, Science, 312(5781):1780-2 (2006).
Pendry, J.B. et al., Magnetism from conductors and enhanced nonlinear phenomena, IEEE Transactions on Microwave Theory and Techniques, 47(11):2075-2084 (1999).
Perry, H. et al., Nano- and Micropatterning of Optically Transparent, Mechanically Robust, Biocompatible Sillk Fibroin Films, Advanced Materials, 20:3070-3072 (2008).
Popescu, R. et al., Molecular Crystals and Liquid Crystals, 522:229 (2010).
Pritchard, E.M. et al., Sustained-release silk biomaterials for drug delivery and tissue engineering scaffolds, Bioengineering Conference, IEEE 35th Annual Northeast, 2 pages (2009).
Pupeza, I. et al., Highly accurate optical material parameter determination with THz time-domain spectroscopy, Opt. Express, 15(7):4335-50 (2007).
Sashina et al., Structure and Solubility of Natural Silk Fibroin, Russ. J. Appl. Chem., 79: 869-76 (2006).
Schurig, D. et al., Electric-field-coupled resonators for negative permittivity metamaterials, Applied Physics Letters, 88:041109 (2006).
Schurig, D. et al., Metamaterial electromagnetic cloak at microwave frequencies, Science, 314(5801):977-80 (2006).
Servoli, E. et al., Folding and assembly of fibroin driven by an AC electric field: Effects on film properties, Macromolecular Bioscience, 8(9):827-835 (2008).
She, H. et al., Estimation of Adhesion Hysteresis at Polymer/Oxide Interfaces Using Rolling Contact Mechanics, Langmuir, 14:3090-3100 (1998).
Shelby, R.A. et al., Experimental verification of a negative index of refraction, Science, 292(5514):77-9 (2001).
Shi, X.W. et al., Chitosan biotinylation and electrodeposition for selective protein assembly, Macromol. Biosci., 8(5):451-7 (2008).
Shi, X.W. et al., Reagentless Protein Assembly Triggered by Localized Electrical Signals, Advanced Materials, 21(9): 984-988 (2009).
Sillen, C.W.M.P. et al., Gas bubble behaviour during water electrolysis, International Journal of Hydrogen Energy, 7(7):577-587 (1982).
Smith, D.R. et al., Composite medium with simultaneously negative permeability and permittivity, Phys. Rev. Lett., 84(18):4184-7 (2000).
Sofia, S. et al., Functionalized silk-based biomaterials for bone formation, Journal of Biomedical Materials Research, 54(1): 139-148 (2001).
Sookne, A.M. and Harris, M., Electrophoretic Studies of Silk, Textile Res., 9:374-383 (1939).
Takei, F. et al., Further evidence for importance of the subunit combination of silk fibroin in its efficient secretion from the posterior silk gland cells, Journal of Cellular Biology, 105(1):175-180 (1987).
Tanaka, K. et al., Determination of the site of disulfide linkage between heavy and light chains of silk fibroin produced by Bombyx mori, Biochimica et Biophysica Acta, 1432:92-103 (1999).
Tanaka, K. et al., Immunological identification of the major disulfide-linked light component of silk fibroin, Journal of Biochemistry, 114(1):1-4 (1993).
Tao et al, Gold nanoparticle-doped biocompatible silk films as a path to implantable thermo-electrically wireless powering devices, Applied Physics Letters, 97:123702 (2010).
Tao, H. et al., Terahertz metamaterials on free-standing highly-flexible polyimide substrates, J. Phys. D: Appl. Phys., 41:232004 (2008).
Tao, H. et al., A metamaterial absorber for the terahertz regime: design, fabrication and characterization, Opt. Express, 16(10):7181-8 (2008).
Tao, H. et al., Highly flexible wide angle of incidence terahertz metamaterial absorber: Design, fabrication, and characterization, Phys. Rev. B, 78:241103(R) (2008).
Tao, H. et al., Metamaterial silk composites at terahertz frequencies, Adv. Mater., 22(32):3527-31 (2010).
Terry, A.E. et al., pH induced changes in the rheology of silk fibroin solution from the middle division of Bombyx mori silkworm, Biomacromolecules, 5:768-776 (2004).
Valluzzi, R., et al., Orientation of silk III at the air-water interface, Int. J. Biol. Macromol., 24(2-3): 237-242 (1999).
Yi, H. et al., Biofabrication with chitosan. Biomacromolecules, 6(6):2881-94 (2005).
Yucel, T. et al., Non-equilibrium Silk Fibroin Adhesives, J. Struct Biol., 170(2): 406-412 (2010).
Zhou, C.Z. et al, Fine organization of Bombyx mori fibroin heavy chain gene, Nucleic Acids Research, 28(12):2413-2419 (2000).
Zhou, C.Z. et al., Silk fibroin: structural implications of a remarkable amino acid sequence, Proteins: Structure, Function, and Genetics, 44(2):119-122 (2001).
Zhu, J. et al., Electrospinning and rheology of regenerated Bombyx mori silk fibroin aqueous solutions: The effects of pH and concentration, Polymer, 49:2880-2885 (2008).
Popescu, R. et al., Biopolymer thin films for photonics applications, Key Engineering Materials, 415:33-36 (2009).
Zhou, S. and Yan, C., Simulation study on a negative refractive index material with high transmission at 748THz—The violet end of the visible region, Physics Journal, 59(1):360-364 (2010). [English Abstract Only].
International Preliminary Report on Patentability of PCT/US2011/032195, 7 pages (Oct. 26, 2012).
International Search Report of PCT/US2011/032195, mailed Oct. 27, 2011, 3 pages.
Written Opinion of PCT/US2011/032195, mailed Oct. 27, 2011, 5 pages.
Croenne, C. et al., Left handed metamaterials at Terahertz frequencies, Infrared and Millimeter Waves, pp. 866-868 (Sep. 9, 2007).
Liu et al., Metamaterials on parylene thin film substrates: Design, fabrication, and characterization at terahertz frequency, Applied Physics Letters, 96:011906, 3 pages (2010).
Sameoto, D. et al., Micromask generation for polymer morphology control: nanohair fabrication for synthetic dry adhesives, Advances in Science and Technology, 54:439-444 (2009).
Yang, Y. H., et al., Influence of pH Value on the Structure of Regenerated Bombyx mori Silk Fibroin in Aqueous Solution by Optical Spectroscopy, Acta Chimica Sinica, 64:1730 (2006) [English Abstract Only].

(56) References Cited

OTHER PUBLICATIONS

Zha, J., Study of properties of photonic crystal on Terahertz brand and guided media, National Excellent MA Theses, pp. 43-48 (Nov. 15, 2009). [English Abstract Only].

Zhou, S. and Yan, C., Simulation study on a negative refractive index material with high transmission at 748THz—the violet end of the visible region, Physics Journal, 59(1):360-364 (2010) [English Abstract Only].

* cited by examiner

FIG. 4 Simulation and experiment results showing mimicking of the electromagnetic response the molecule biotin using terahertz MMs

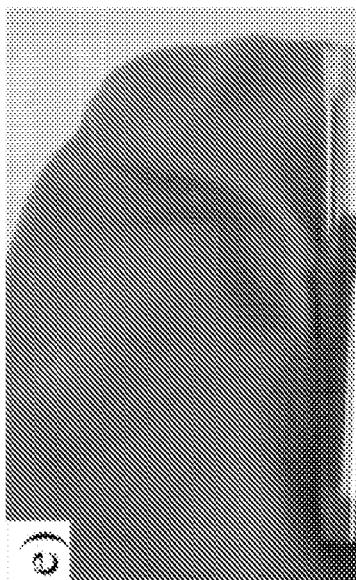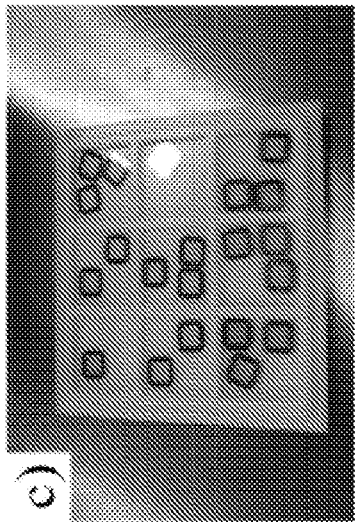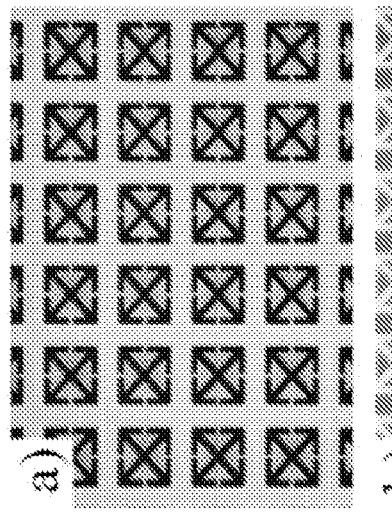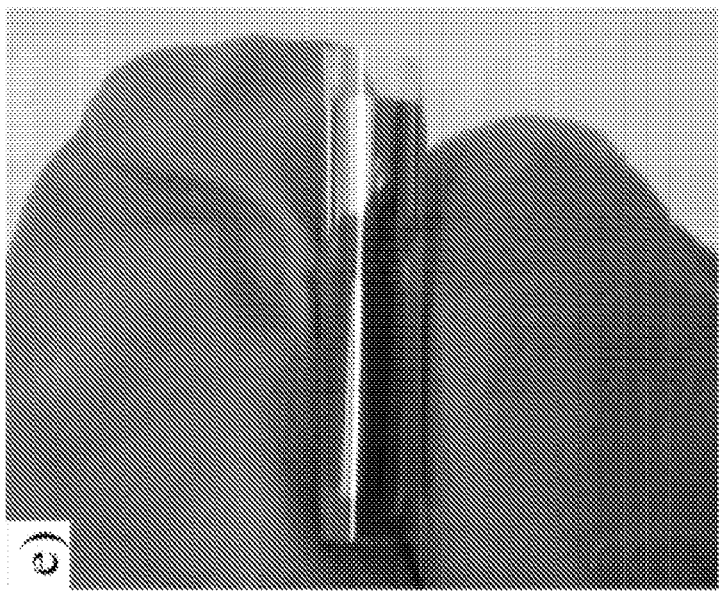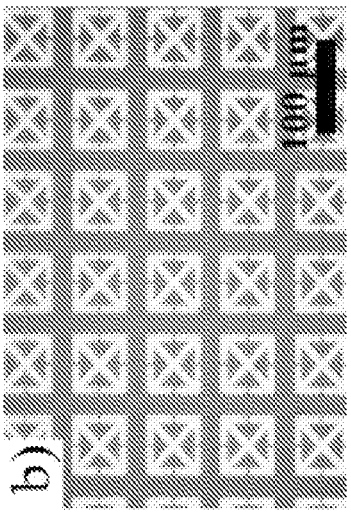
FIG. 8A  FIG. 8C  FIG. 8E
FIG. 8B  FIG. 8D

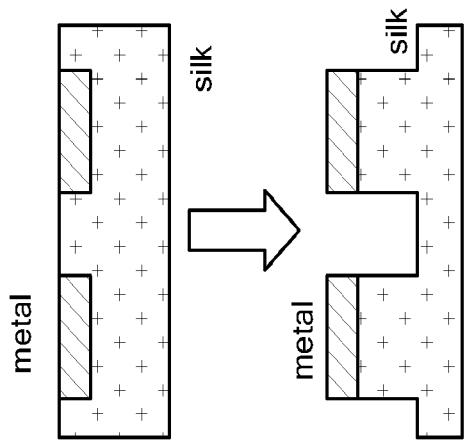
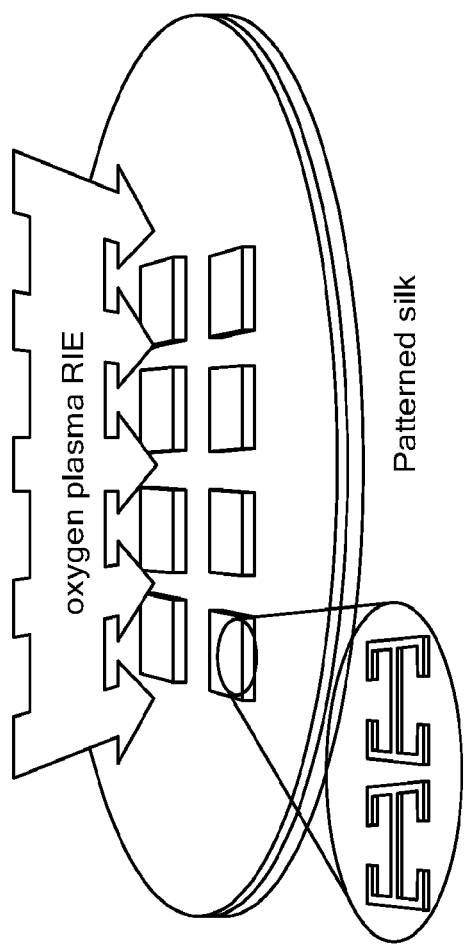
FIG. 10

SILK ELECTRONIC COMPONENTS

RELATED APPLICATIONS

This application is a 35 U.S.C. §371 National Stage of International Application No. PCT/US2011/32195, entitled "Silk Electronic Components" and filed on Apr. 12, 2011, which claims the benefit of and priority to U.S. Provisional Application No. 61/323,172 filed Apr. 12, 2010, 61/325,593 filed Apr. 19, 2010, and 61/446,158 filed Feb. 24, 2011, the contents of all of which are hereby incorporated by reference in their entirety.

SEQUENCE LISTING

The present specification makes reference to amino acid sequences, which are included in a Revised Sequence Listing (submitted electronically as a .txt file named "Sequence_Listing.txt"). The revised .txt file was generated on Jun. 3, 2013 and is 9 kb in size. The entire contents of the Revised Sequence Listing are herein incorporated by reference.

GOVERNMENT SUPPORT

This invention was made with government support under grant FA9550-07-1-0079 awarded by the United States Air Force and grant W911NF-07-1-0618 awarded by the United States Army. The government has certain rights in the invention.

BACKGROUND

Electronic components are fundamental to an enormous number of devices that power our modern lives. Perhaps the simplest of these components, the antenna, converts the power of electromagnetic radiation into voltage. Resonator components amplify radiation of specified frequency.

The present invention provides novel electronic components with remarkable attributes. Among other things, provided components are biocompatible and create possibilities for development and/or implementation of electronic devices in biological contexts not previously accessible.

SUMMARY

The present invention encompasses the recognition that silk materials are unusually useful as matrices for electronic components. Among other things, the present invention provides silk electronic components comprising a silk matrix and a patterned structure composed of a conductive material, such as metal. In some embodiments, the patterned conductive structure is an antenna, such as a metal antenna. In some embodiments, the patterned conductive structure is a resonator (e.g., a split-ring resonator, "SRR"), e.g., a metal resonator. In some embodiments, the patterned conductive structure is a radio-frequency identification device (RFID), e.g., a metal RFID. In some embodiments, provided silk electronic components are metamaterials; the present invention therefore provides metamaterial compositions and methods for fabricating the same.

According to the present invention, silk attributes that make it particularly amenable to use in provided silk electronic components include, among other things, its ability to assemble into a material showing smoothness, in some embodiments almost at atomic scale. In some embodiments, the silk matrix in provided silk electronic components shows smoothness that is less than about 10 nm, 9 nm, 8 nm, 7 nm, 6 nm, 5 nm, 4 nm, 3 nm, 2 nm or about 1 nm.

Alternatively or additionally, attributes of silk materials that make it particularly useful in accordance with some embodiments of the present invention include its amenability to processes for deposition of patterned structures composed of conductive material, e.g., metal. In some embodiments, silk materials utilized in accordance with the present invention are amenable to lithography techniques for application of structures that are composed of conductive material, such as metal. Surface smoothness may contribute to amenability to lithography. In some embodiments, silk materials utilized in accordance with the present invention are amenable to transfer by contact. In such embodiments, utilized silk materials show desirable metal adhesion properties.

Alternatively or additionally, attributes of silk materials that make it particularly useful in accordance with some embodiments of the present invention include its biocompatibility.

Alternatively or additionally, attributes of silk materials that make it particularly useful in accordance with some embodiments of the present invention include its amenability to controlled degradation. As described in more detail below, much is known about fabricating silk films with a known time course of degradation. WO 2008/118133; WO 2004/080346; WO 2005/123114; WO 2007/016524; WO 2008/150861.

Alternatively or additionally, attributes of silk materials that make it particularly useful in accordance with some embodiments of the present invention include its tensile strength.

Alternatively or additionally, attributes of silk materials that make it particularly useful in accordance with some embodiments of the present invention include its flexibility.

Among other things, the present invention provides the recognition that these various attributes render silk a material of particular interest and value for use in silk electronic components. Moreover, the present invention identifies those particular silk compositions, forms, or materials useful in relevant electronic applications.

In some embodiments, the present invention provides silk electronic components that operate at teraherz (THz, 1 THz=1012 Hz) frequencies. The THz region of the electromagnetic spectrum has the potential for applications ranging from spectroscopic imaging to short-range secure communication. Naturally occurring materials, however, typically do not have the appropriate response at THz frequencies. Thus, to date, important THz components and devices such as switches, modulators, and phase shifters, have not been readily available in nature. Appropriate components and devices remain to be explored for the generation, detection, and spatial and temporal control of THz radiation to realize the applications in THz regime. By further extending the material design implemented in THz frequencies, the designed components and devices would be applicable at a broader wavelength regime. In certain embodiments, the present invention provides new and valuable THz components comprising a silk matrix and a patterned structure of conductive nature.

The development of metamaterials has dramatically expanded the general view of electromagnetic material interactions. Metamaterials with a user-designed electromagnetic response at a precisely controlled target frequency may lead to novel electromagnetic responses or phenomena, such as negative refractive index, perfect lenses, or perfect absorbers. Designing novel devices that ideally integrate the electromagnetic properties of the metamaterial structure without impairing the anticipated functions of the devices would be desirable in various applications such as biosensing and biodetecting. The present invention provides silk metamaterials, and further provides methods and devices that utilize them.

Moreover, the present invention encompasses the recognition that construction of metamaterials that are not constrained as planar structures is also desirable for various applications, such as implantable bioelectronic and biophotonic devices. A resonant metamaterial absorber at THz frequencies was fabricated based on two metallic layers structure separated by polyimide. See Tao et al., Phys. Rev. B, 78: 241103(R) (2008). However, the particular structure described in Tao et al. was fabricated on a rigid semiconductor substrate. Recently, a large area, free-standing metamaterial composites consisting of split ring resonators on a polyimide substrate as thin as 6 microns (~λ/50 in the propagation direction) has been fabricated with a high-quality resonant response, which may provide potential applications for non-planar metamaterial composites in areas such as electromagnetic cloaks or concentrators. See Tao et al., J. Phys. D: Appl. Phys., 41: 232004 (2008).

Although metamaterial composite using polyimide as non-planar substrate is an effective electromagnetic material, it may not necessarily provide the biocompatibility and biodegradability and confer additional biofunctionality to the metamaterials for using as a bio-integrated device. The present invention encompasses the recognition that there remains a need in the art to develop a metamaterial composite that can integrate the metamaterial structures on a highly transparent and flexible substrate that are biocompatible and biodegradable so as to be incorporated in versatile bio-integrated devices. Additionally, according to the present invention, metamaterial composite using a matrix that can incorporate bio-dopants, such as enzymes and proteins, or electrically and optically active dopants, is also desirable to hybridize multiple functionalities into bio-integrated device designs. Moreover, the present invention encompasses the recognition that various properties of silk render it particularly suitable for use in a metamaterial, and furthermore permit development of biocompatible metamaterials, in some embodiments including one or more bio-dopants.

Silk metamaterial composites provided in accordance with the present invention can comprise an array of metamaterial elements disposed on or embedded in the silk matrix, forming a resonant electromagnetic structure that modulates an electromagnetic radiation at a wide range of frequencies including terahertz regime. A simple methodology is provided herein to directly spray large-area metamaterial structures on biocompatible silk substrates, resulting in a silk metamaterial composite with a resonant electromagnetic structure that exhibits strong resonances at desired frequencies. Such a silk metamaterial composite can modulate an electromagnetic radiation at a wide range of electromagnetic spectrum including, but not limited to, a THz regime.

Silk metamaterial composites, or other silk electronic components described herein, can be used in novel devices such as biosensors, labels and identifiers, surveillance devices, invisible cloaks, electromagnetic concentrators or antennas, particularly in implantable bioelectric and/or biophotonic devices in the areas of in vivo bio-tracking, biomimicry, silk electronics, silk photonics, and implantable biosensor and biodetectors.

One aspect of the invention relates to a silk electronic component or metamaterial composite having resonant sub-wavelength magnetic properties that comprises one or more layers of metamaterial or patterned structure made of conductive material (e.g., metal) and a silk substrate that carries the one or more layers of metamaterial or patterned structure made of conductive material (e.g., metal) on the substrate.

Some embodiments of the invention provide a silk metamaterial composite for modulating an electromagnetic radiation, comprising a resonant electromagnetic structure comprising an array of metamaterial elements and a silk matrix, where the resonant electromagnetic structure of the silk metamaterial composite is constructed to modulate the electromagnetic radiation. The metamaterial elements may be disposed on or embedded in the silk matrix. At least some of the metamaterial elements are smaller than the wavelength of the electromagnetic radiation for inducing subwavelength resonant electromagnetic response.

Some embodiments of the invention provide novel devices applications of the silk metamaterial composite as described herein. For example, the silk metamaterial composite can be fabricated into biosensing and bio-detecting devices, surveillance devices, electromagnetic cloaking devices, electromagnetic antenna devices, and the like.

In some embodiments, provided herein is an implantable device comprising a silk metamaterial composite comprising an array of metamaterial elements, disposed on or embedded in a silk matrix, where the sizes of the metamaterial elements are less than the wavelength of the electromagnetic radiation, and the silk metamaterial composite is capable of modulating the electromagnetic radiation.

Another aspect of the invention relates to a method of fabricating a silk metamaterial composite having resonant electromagnetic properties. The method comprises the steps of contact-positioning a shadow mask on to a silk substrate; and spray-depositing a conductive material on a silk substrate through the shadow mask thereby forming an array of metamaterial elements on the silk substrate. The shadow mask used herein provides a desired geometry for the metamaterial elements that defines the resonant electromagnetic properties of the silk metamaterial composite.

BRIEF DESCRIPTION OF THE DRAWING

FIG. 8A shows a microscopic photography of a portion of the as-fabricated micro stencil; FIG. 8B shows a microscopic photography of a portion of the sprayed array of the metamaterial elements; FIG. 8C is a photograph of micro stencils for fabricating metamaterial; FIG. 8D is a photograph of the as-fabricated silk metamaterial composite; and FIG. 8E shows a wrapped "capsule" of the silk metamaterial composite.

FIG. 10 shows the use of patterned conductive structures as a hard mask for subsequent RIE processes.

FIG. 11 also shows a SEM image of an array of aluminum patterned conductive structures overlaying RIE etched structures (e.g., resonators). The structures produced by casting and subsequent RIE processing are consistent over the 100×100 SRR array.

FIG. 20B shows metamaterial structures obtained in the STAMP process. FIG. 20C shows an optical transmission micrograph of an aluminum metamaterial patterned silk film.

DETAILED DESCRIPTION OF CERTAIN EMBODIMENTS

Silk Matrix

Figure 1:
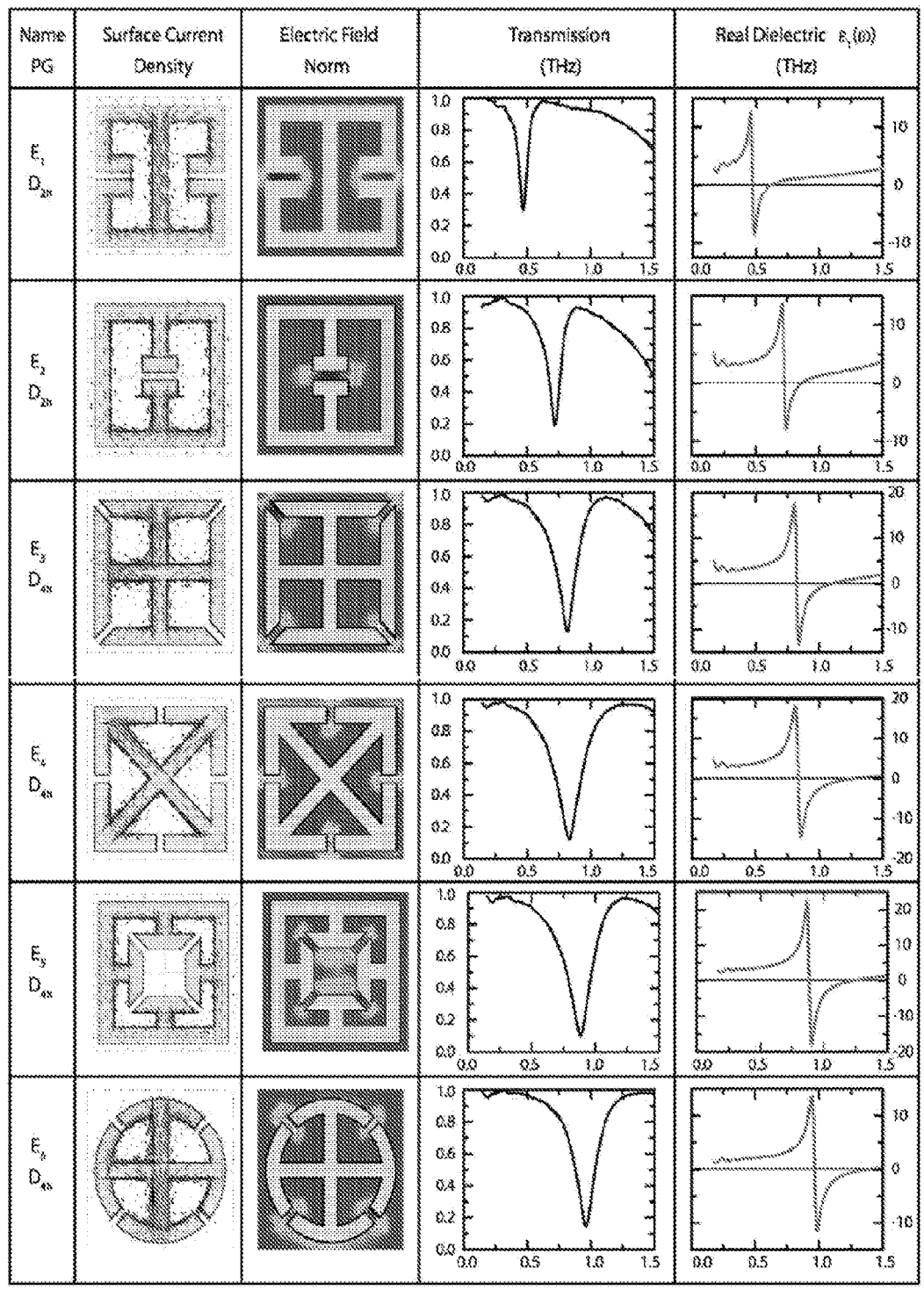
FIGS. 1 and 2 show images of exemplary silk metamaterial composites and their different frequency responses at the terahertz (THz) regime.

Silk is a natural protein fiber produced in a specialized gland of certain organisms. Silk production in organisms is especially common in the Hymenoptera (bees, wasps, and ants), and is sometimes used in nest construction. Other types of arthropod also produce silk, most notably various arachnids such as spiders (e.g., spider silk). Silk fibers generated by insects and spiders represent the strongest natural fibers known and rival even synthetic high performance fibers.

Silk has been a highly desired and widely used textile since its first appearance in ancient China. See Elisseeff, "The Silk Roads: Highways of Culture and Commerce," Berghahn Books/UNESCO, New York (2000); Vainker, "Chinese Silk: A Cultural History," Rutgers University Press, Piscataway, N.J. (2004). Glossy and smooth, silk is favored by not only fashion designers but also tissue engineers because it is mechanically tough but degrades harmlessly inside the body, offering new opportunities as a highly robust and biocompatible material substrate. See Altman et al., Biomaterials, 24: 401 (2003); Sashina et al., Russ. J. Appl. Chem., 79: 869 (2006).

Silk is naturally produced by various species, including, without limitation: *Antheraea mylitta; Antheraea pernyi; Antheraea yamamai; Galleria mellonella; Bombyx mori; Bombyx mandarina; Galleria mellonella; Nephila clavipes; Nephila senegalensis; Gasteracantha mammosa; Argiope aurantia; Araneus diadematus; Latrodectus geometricus; Araneus bicentenaries; Tetragnatha versicolor; Araneus ventricosus; Dolomedes tenebrosus; Euagrus chisoseus; Plectreurys tristis; Argiope trifasciata*; and *Nephila madagascariensis*.

In general, silk for use in accordance with the present invention may be produced by any such organism, or may be prepared through an artificial process, for example, involving genetic engineering of cells or organisms to produce a silk protein and/or chemical synthesis. In some embodiments of the present invention, silk is produced by the silkworm, *Bombyx mori*.

As is known in the art, silks are modular in design, with large internal repeats flanked by shorter (~100 amino acid) terminal domains (N and C termini) Silks have high molecular weight (200 to 350 kDa or higher) with transcripts of 10,000 base pairs and higher and >3000 amino acids (reviewed in Omenatto and Kaplan (2010) Science 329: 528-531). The larger modular domains are interrupted with relatively short spacers with hydrophobic charge groups in the case of silkworm silk. N- and C-termini are involved in the assembly and processing of silks, including pH control of assembly. The N- and C-termini are highly conserved, in spite of their relatively small size compared with the internal modules.

Table 1, below, provides an exemplary list of silk-producing species and silk proteins:

TABLE 1

An exemplary list of silk-producing species and silk proteins (adopted from Bini et al. (2003), J. Mol. Biol. 335(1): 27-40).

| Accession | Species | Producing gland | Protein |
|---|---|---|---|
| A. Silkworms | | | |
| AAN28165 | *Antheraea mylitta* | Salivary | Fibroin |
| AAC32606 | *Antheraea pernyi* | Salivary | Fibroin |
| AAK83145 | *Antheraea yamamai* | Salivary | Fibroin |
| AAG10393 | *Galleria mellonella* | Salivary | Heavy-chain fibroin (N-terminal) |
| AAG10394 | *Galleria mellonella* | Salivary | Heavy-chain fibroin (C-terminal) |
| P05790 | *Bombyx mori* | Salivary | Fibroin heavy chain precursor, Fib-H, H-fibroin |
| CAA27612 | *Bombyx mandarin* | Salivary | Fibroin |
| Q26427 | *Galleria mellonella* | Salivary | Fibroin light chain precursor, Fib-L, L-fibroin, PG-1 |
| P21828 | *Bombyx mori* | Salivary | Fibroin light chain precursor, Fib-L, L-fibroin |
| B. Spiders | | | |
| P19837 | *Nephila clavipes* | Major ampullate | Spidroin 1, dragline silk fibroin 1 |
| P46804 | *Nephila clavipes* | Major ampullate | Spidroin 2, dragline silk fibroin 2 |
| AAK30609 | *Nephila senegalensis* | Major ampullate | Spidroin 2 |
| AAK30601 | *Gasteracantha mammosa* | Major ampullate | Spidroin 2 |
| AAK30592 | *Argiope aurantia* | Major ampullate | Spidroin 2 |
| AAC47011 | *Araneus diadematus* | Major ampullate | Fibroin-4, ADF-4 |
| AAK30604 | *Latrodectus geometricus* | Major ampullate | Spidroin 2 |
| AAC04503 | *Araneus bicentenarius* | Major ampullate | Spidroin 2 |
| AAK30615 | *Tetragnatha versicolor* | Major ampullate | Spidroin 1 |
| AAN85280 | *Araneus ventricosus* | Major ampullate | Dragline silk protein-1 |
| AAN85281 | *Araneus ventricosus* | Major ampullate | Dragline silk protein-2 |
| AAC14589 | *Nephila clavipes* | Minor ampullate | MiSp1 silk protein |
| AAK30598 | *Dolomedes tenebrosus* | Ampullate | Fibroin 1 |
| AAK30599 | *Dolomedes tenebrosus* | Ampullate | Fibroin 2 |
| AAK30600 | *Euagrus chisoseus* | Combined | Fibroin 1 |
| AAK30610 | *Plectreurys tristis* | Larger ampule-shaped | Fibroin 1 |
| AAK30611 | *Plectreurys tristis* | Larger ampule-shaped | Fibroin 2 |
| AAK30612 | *Plectreurys tristis* | Larger ampule-shaped | Fibroin 3 |
| AAK30613 | *Plectreurys tristis* | Larger ampule-shaped | Fibroin 4 |
| AAK30593 | *Argiope trifasciata* | Flagelliform | Silk protein |
| AAF36091 | *Nephila madagascariensis* | Flagelliform | Fibroin, silk protein (N-terminal) |
| AAF36092 | *Nephila madagascariensis* | Flagelliform | Silk protein (C-terminal) |
| AAC38846 | *Nephila clavipes* | Flagelliform | Fibroin, silk protein (N-terminal) |
| AAC38847 | *Nephila clavipes* | Flagelliform | Silk protein (C-terminal) |

Silk Fibroin

Fibroin is a type of structural protein produced by certain spider and insect species that produce silk. Cocoon silk produced by the silkworm, *Bombyx mori*, is of particular interest because it offers low-cost, bulk-scale production suitable for a number of commercial applications, such as textile.

Silkworm cocoon silk contains two structural proteins, the fibroin heavy chain (~350 k Da) and the fibroin light chain (~25 k Da), which are associated with a family of non-structural proteins termed sericin, which glue the fibroin brins together in forming the cocoon. The heavy and light chains of fibroin are linked by a disulfide bond at the C-terminus of the two subunits (Takei, F., Kikuchi, Y., Kikuchi, A., Mizuno, S, and Shimura, K. (1987) J. Cell Biol., 105, 175-180; Tanaka, K., Mori, K. and Mizuno, S. (1993) J. Biochem. (Tokyo), 114, 1-4; Tanaka, K., Kajiyama, N., Ishikura, K., Waga, S., Kikuchi, A., Ohtomo, K., Takagi, T. and Mizuno, S. (1999) Biochim. Biophys. Acta, 1432, 92-103; Y Kikuchi, K Mori, S Suzuki, K Yamaguchi and S Mizuno, Structure of the *Bombyx mori* fibroin light-chain-encoding gene: upstream sequence elements common to the light and heavy chain, Gene 110 (1992), pp. 151-158). The sericins are a high molecular weight, soluble glycoprotein constituent of silk which gives the stickiness to the material. These glycoproteins are hydrophilic and can be easily removed from cocoons by boiling in water.

As used herein, the term "silk fibroin" refers to silk fibroin protein, whether produced by silkworm, spider, or other insect, or otherwise generated (Lucas et al., Adv. Protein Chem., 13: 107-242 (1958)). In some embodiments, silk fibroin is obtained from a solution containing a dissolved silkworm silk or spider silk. For example, in some embodiments, silkworm silk fibroins are obtained, from the cocoon of *Bombyx mori*. In some embodiments, spider silk fibroins are obtained, for example, from *Nephila clavipes*. In the alternative, in some embodiments, silk fibroins suitable for use in the invention are obtained from a solution containing a genetically engineered silk harvested from bacteria, yeast, mammalian cells, transgenic animals or transgenic plants. See, e.g., WO 97/08315 and U.S. Pat. No. 5,245,012, each od which is incorporated herein as reference in its entirety.

Thus, in some embodiments, a silk solution is used to fabricate compositions of the present invention contain fibroin proteins, essentially free of sericins. In some embodiments, silk solutions used to fabricate various compositions of the present invention contain the heavy chain of fibroin, but are essentially free of other proteins. In other embodiments, silk solutions used to fabricate various compositions of the present invention contain both the heavy and light chains of fibroin, but are essentially free of other proteins. In certain embodiments, silk solutions used to fabricate various compositions of the present invention comprise both a heavy and a light chain of silk fibroin; in some such embodiments, the heavy chain and the light chain of silk fibroin are linked via at least one disulfide bond. In some embodiments where the heavy and light chains of fibroin are present, they are linked via one, two, three or more disulfide bonds.

Although different species of silk-producing organisms, and different types of silk, have different amino acid compositions, various fibroin proteins share certain structural features. A general trend in silk fibroin structure is a sequence of amino acids that is characterized by usually alternating glycine and alanine, or alanine alone. Such configuration allows fibroin molecules to self-assemble into a beta-sheet conformation. These "Ala-rich" hydrophobic blocks are typically separated by segments of amino acids with bulky side-groups (e.g., hydrophilic spacers).

In some embodiments, core repeat sequences of the hydrophobic blocks of fibroin are represented by the following amino acid sequences and/or formulae:

$(GAGAGS)_{5-15}$; (SEQ ID NO: 1)

$(X = V, I, A)$; (SEQ ID NO: 2)

GAAS; (SEQ ID NO: 3)

$(S_{1-2}A_{11-13})$; (SEQ ID NO: 4)

$GX_{1-4}GGX$; (SEQ ID NO: 5)

GGGX (X = A, S, Y, R, D, V, W, R, D); (SEQ ID NO: 6)

$(S_{1-2}A_{1-4})_{1-2}$; (SEQ ID NO: 7)

GLGGLG; (SEQ ID NO: 8)

GXGGXG (X = L, I, V, P); (SEQ ID NO: 9)

$(GP(GGX)_{1-4} Y)_n$ (X = Y, V, S, A); (SEQ ID NO: 10)

GRGGAn; (SEQ ID NO: 11)

GGXn (X = A, T, V, S); GAG(A)$_{6-7}$GGA; and (SEQ ID NO: 12)

GGX GX GXX (X = Q, Y, L, A, S, R). (SEQ ID NO: 13)

In some embodiments, a fibroin peptide contains multiple hydrophobic blocks, e.g., 3, 4, 5, 6, 7, 8, 9, 10, 11, 12, 13, 14, 15, 16, 17, 18, 19 and 20 hydrophobic blocks within the peptide. In some embodiments, a fibroin peptide contains between 4-17 hydrophobic blocks.

In some embodiments of the invention, a fibroin peptide comprises at least one hydrophilic spacer sequence ("hydrophilic block") that is about 4-50 amino acids in length. Non-limiting examples of the hydrophilic spacer sequences include:

TGSSGFGPYVNGGYSG; (SEQ ID NO: 14)

YEYAWSSE; (SEQ ID NO: 15)

SDFGTGS; (SEQ ID NO: 16)

RRAGYDR; (SEQ ID NO: 17)

EVIVIDDR; (SEQ ID NO: 18)

TTIIEDLDITIDGADGPI and (SEQ ID NO: 19)

TISEELTI. (SEQ ID NO: 20)

In certain embodiments, a fibroin peptide contains a hydrophilic spacer sequence that is a derivative of any one of the representative spacer sequences listed above. Such derivatives are at least 75%, at least 80%, at least 85%, at least 90%, or at least 95% identical to any one of the hydrophilic spacer sequences.

In some embodiments, a fibroin peptide suitable for the present invention contains no spacer.

As noted, silks are fibrous proteins and are characterized by modular units linked together to form high molecular weight, highly repetitive proteins. These modular units or domains, each with specific amino acid sequences and chemistries, are thought to provide specific functions. For example, sequence motifs such as poly-alanine (polyA) and poly-alanine-glycine (poly-AG) are inclined to be beta-sheet-forming; GXX motifs contribute to 31-helix formation; GXG motifs provide stiffness; and, GPGXX (SEQ ID NO: 22) contributes to beta-spiral formation. These are examples of key components in various silk structures whose positioning and arangement are intimately tied with the end material properties of silk-based materials (reviewed in Omenetto and Kaplan (2010) Science 329: 528-531).

It has been observed that the beta-sheets of fibroin proteins stack to form crystals, whereas the other segments form amorphous domains. It is the interplay between the hard crystalline segments, and the strained elastic semi amorphous regions, that gives silk its extraordinary properties.

Non-limiting examples of repeat sequences and spacer sequences from various silk-producing species are provided in Table 2 below.

TABLE 2

Hydrophobic and hydrophilic components of fibroin sequences (adopted from Bini et al. (2003), J. Mol. Biol. 335(1): 27-40).

| Species | Hydrophilic blocks | | | Hydrophobic blocks | | |
|---|---|---|---|---|---|---|
| | N-term aa | C-term aa | Hydrophilic spacer (aa) % representative sequence | Range, aa | # of Blocks | Core repeat sequences |
| A. *Lepidoptera* (Heavy chain fibroin) | | | | | | |
| *Bombyx mori* | 151 | 50 | 32-33, TGSSGFGPYVNGGYSG, (SEQ ID NO: 14) | 159-607 | 12 | $(GAGAGS)_{5-15}$, (SEQ ID NO: 1); $(GX)_{5-15}$ (X = V, I, A), (SEQ ID NO: 2); GAAS (SEQ ID NO: 3) |
| *Bombyx mandarina* | 151 | | YEYAWSSE, (SEQ ID NO: 15) | | | |
| *Antheraea mylitta* | 86 | | SDFGTGS, (SEQ ID NO: 16) | | | |
| *Antherara pernyi* | 87 | 32 | | | | |
| *Antheraea yamamai* | 87 | 32 | 7, RRAGYDR, (SEQ ID NO: 17) | 140-340 | 16 | $(S_{1-2}A_{11-13})$, (SEQ ID NO: 4); $GX_{1-4}GGX$, (SEQ ID NO: 5); GGGX (X = A, S, Y, R, D V, W, R, D), (SEQ ID NO: 6) |
| *Galleria mellonella* | 189 | 60 | 6-8, EVIVIDDR, (SEQ ID NO: 18) | 75-99 | 13 | $(S_{1-2}A_{1-4})_{1-2}$, (SEQ ID NO: 7); GLGGLG, (SEQ ID NO: 8); GXGGXG (X = L, I, V, P), (SEQ ID NO: 9); GPX (X = L, Y, I) |
| B. *Arachnida* | | | | | | |
| *Nephila clavipes* | 115 | 89 | | | | |
| *Nephila madascariensis* | 115 | 89 | 26, TTIIEDLDITIDG ADGPI, (SEQ ID NO: 19) | 260-380 | 5 | (GP(GGX)1-4 Y)n (X = Y, V, S, A), (SEQ ID NO: 10) |
| *Argiope trifasciata* | | 113 | | | | GRGGAn, (SEQ ID NO: 11); GGXn (X = A, T, V, S) |
| *Major ampullata* | | | TISEELTI, (SEQ ID NO: 20) | | | |
| *Nephila clavipes* | | 97 | No spacer | 19-46 | | $GAG(A)_{6-7}GGA$, (SEQ ID NO: 12); GGX GX GXX (X = Q, Y, L, A, S, R), (SEQ ID NO: 13) |
| *Gasteracantha mammosa* | | 89 | No spacer | | | |
| *Argiope aurantia* | | 82 | No spacer | | | |

TABLE 2-continued

Hydrophobic and hydrophilic components of fibroin sequences
(adopted from Bini et al. (2003), J. Mol. Biol. 335(1): 27-40).

| | Hydrophilic blocks | | | Hydrophobic blocks | | |
|---|---|---|---|---|---|---|
| Species | N-term aa | C-term aa | Hydrophilic spacer (aa) representative sequence | Range, % aa | # of Blocks | Core repeat sequences |
| Nephila sesegalensis | | 82 | No spacer | | | |
| Latrodectus geometricus | | 88 | No spacer | | | |
| Araneus diadematus | | 94 | No spacer | | | |

The particular silk materials explicitly exemplified herein were typically prepared from material spun by silkworm, *B. Mori*. Typically, cocoons are boiled for ~30 min in an aqueous solution of 0.02M $Na_2CO_3$, then rinsed thoroughly with water to extract the glue-like sericin proteins. The extracted silk is then dissolved in LiBr (such as 9.3 M) solution at room temperature, yielding a 20% (wt.) solution. The resulting silk fibroin solution can then be further processed for a variety of applications as described elsewhere herein. Those of ordinary skill in the art understand other sources available and may well be appropriate, such as those exemplified in the Table above.

Fibroin Structure and Self-Assembly

The complete sequence of the *Bombyx mori* fibroin gene has been determined (C.-Z Zhou, F Confalonieri, N Medina, Y Zivanovic, C Esnault and T Yang et al., Fine organization of *Bombyx mori* fibroin heavy chain gene, Nucl. Acids Res. 28 (2000), pp. 2413-2419). The fibroin coding sequence presents a spectacular organization, with a highly repetitive and G-rich (~45%) core flanked by non-repetitive 5' and 3' ends. This repetitive core is composed of alternate arrays of 12 repetitive and 11 amorphous domains. The sequences of the amorphous domains are evolutionarily conserved and the repetitive domains differ from each other in length by a variety of tandem repeats of subdomains of ~208 bp.

The silkworm fibroin protein consists of layers of antiparallel beta sheets whose primary structure mainly consists of the recurrent amino acid sequence (Gly-Ser-Gly-Ala-Gly-Ala)n (SEQ ID NO: 21). The beta-sheet configuration of fibroin is largely responsible for the tensile strength of the material due to hydrogen bonds formed in these regions. In addition to being stronger than Kevlar, fibroin is known to be highly elastic. Historically, these attributes have made it a material with applications in several areas, including textile manufacture.

Fibroin is known to arrange itself in three structures at the macromolecular level, termed silk I, silk II, and silk III, the first two being the primary structures observed in nature. The silk II structure generally refers to the beta-sheet conformation of fibroin. Silk I, which is the other main crystal structure of silk fibroin, is a hydrated structure and is considered to be a necessary intermediate for the preorganization or prealignment of silk fibroin molecules. In the nature, silk I structure is transformed into silk II structure after spinning process. For example, silk I is the natural form of fibroin, as emitted from the *Bombyx mori* silk glands. Silk II refers to the arrangement of fibroin molecules in spun silk, which has greater strength and is often used commercially in various applications. As noted above, the amino-acid sequence of the β-sheet forming crystalline region of fibroin is dominated by the hydrophobic sequence. Silk fibre formation involves shear and elongational stress acting on the fibroin solution (up to 30% wt/vol.) in the gland, causing fibroin in solution to crystallize. The process involves a lyotropic liquid crystal phase, which is transformed from a gel to a sol state during spinning—that is, a liquid crystal spinning process 1. Elongational flow orients the fibroin chains, and the liquid is converted into filaments.

Silk III is a newly discovered structure of fibroin (Valluzzi, Regina; Gido, Samuel P.; Muller, Wayne; Kaplan, David L. (1999). "Orientation of silk III at the air-water interface". International Journal of Biological Macromolecules 24: 237-242). Silk III is formed principally in solutions of fibroin at an interface (i.e. air-water interface, water-oil interface, etc.).

Silk can assemble, and in fact can self-assemble, into crystalline structures. Silk fibroin can be fabricated into desired shapes and conformations, such as silk hydrogels (WO2005/012606; PCT/US08/65076), ultrathin films (WO2007/016524), thick films, conformal coatings (WO2005/000483; WO2005/123114), foams (WO 2005/012606), electrospun mats (WO 2004/000915), microspheres (PCT/US2007/020789), 3D porous matrices (WO2004/062697), solid blocks (WO2003/056297), microfluidic devices (PCT/US07/83646; PCT/US07/83634), electro-optical devices (PCT/US07/83639), and fibers with diameters ranging from the nanoscale (WO2004/000915) to several centimeters (U.S. Pat. No. 6,902,932). The above mentioned applications and patents are incorporated herein by reference in their entirety. For example, silk fibroin can be processed into thin, mechanically robust films with excellent surface quality and optical transparency, which provides an ideal substrate acting as a mechanical support for high-technology materials, such as thin metal layers and contacts, semiconductor films, dielectic powders, nanoparticles, and the like.

Unique physiochemical properties of silk allows its use in a variety of applications. For example, silk is stable, flexible, durable and biocompatible. Biocompatibility broadly refers to silk's safe and non-toxic nature, including being biodegradable, edible, implantable and non-antigenic (e.g., does not cause irritation or induce immune response). Furthermore, useful silk materials can be prepared through processes that can be carried out at room temperature and are water-based.

Surface Properties of Silk-Based Materials

In addition, silk-based materials can be prepared in accordance with the present invention to be smooth and/or adhesive at the molecular level. In some embodiments, silk-based materials provided by and/or utilized in accordance with the present invention are both smooth and adhesive at the molecular level. Silk-based materials showing molecular level smoothness and/or adhesiveness permit certain applications that are not possible with other materials. Smoothness/roughness plays an important role in determining how a real object will interact with its environment. In certain embodiments, silk-based materials provided by and/or used in accordance with the present invention have affinity for biological surfaces, e.g., cells and soft tissues. Moreover, silk-based materials provided by and/or utilized in accordance with certain embodiments of the present invention exhibit excellent adhesion to conductive materials, such as metal. The present invention embraces the recognition that certain silk materials have can act as in interface between a biological element and a non-biological element (e.g., a conductive and/or electronic element).

In accordance with certain embodiments of the invention, some provided silk-based materials can be prepared to show tackiness (e.g., stickability) when wet. This property, particularly when coupled with surface smoothness as described herein, can render certain silk materials uniquely suitable to serve as nano- and/or micro-scale adhesives that attach (e.g., glue) an electronic (e.g., conductive) element with a biological surface in a way other matrices cannot.

It should be appreciated that not all silk-based compositions necessarily have the surface properties described herein (e.g., an extraordinary high degree of smoothness) that are particularly desirable for silk electronic components. For example, prior to the present invention and its appreciation of certain desirable properties the typical surface roughness of available silk materials was commonly in the range of approximately 10 nm and greater. While this is significantly more "smooth" as compared to other widely used matrix materials, such as PDMS, nano-scale applications for purposes of supporting a non-biological structures composed of conductive materials such as metal, in particular, posed a technical challenge.

As provided in the Example sections below, the present inventors have developed fabrication methods to produce silk matrices of superior surface qualities and malleability (e.g., flexibility) suitable for a nano-scale manipulation directed to silk electronic components of the present invention. In some embodiments, silk matrices prepared according to the methods described herein are characterized by having the surface roughness of less than about 5 nm. In some embodiments, silk matrices suitable for the present invention have the surface roughness of less than about 4.0 nm, about 3.5 nm, about 3.0 nm, about 2.5 nm, about 2.0 nm, about 1.5 nm, or about 1 nm.

Silk matrices that provide excellent surface properties include but are not limited to a STAMP-based silk matrix (see below) and electrogelation-based silk matrix.

The "Silk Transfer Applied Micro Patterning" (STAMP) method enables patterning of large area silk fibroin protein films with metallic micro fabricated features. All processing is performed under ambient conditions in an aqueous environment, which is advantageous in incorporating biological materials such as proteins in these compositions and methods. Thus, the micro patterns fabricated enable masking biopolymer films for dry etching to produce protein-based metamaterial structures. A simple fabrication technique, which in a single step transfers metal micro patterns to free standing silk films under ambient processing conditions. This process is herein referred to as "Silk Transfer Applied Micro Pattering" or STAMP. Additionally, this method adds versatility and utility to silk protein device fabrication by allowing the use of the patterned films as hard masks for oxygen based reactive ion etching (RIE). While RIE per se is a widely used tool for versatile and high throughput micro- and nano patterning, its utility for biopolymers is limited [19] due in part to the lack of convenient methods to apply etching masks to biopolymer films. Thus, the methods described in the present application provide significant versatility in their applications for the fabrication of silk electronic components.

Like STAMP-based silk materials, electrogelation ("e-gel")-based silk matrices exhibit extraordinary smooth surface morphology. As determined by atomic force microscopy (AFM), silk materials prepared by electrogelation may have a surface that is around 1 nm in surface roughness. Such property allows the silk matrix to be etched or manipulated with a nano-scale resolution.

In some embodiments of the present invention, for example when a silk-based material is prepared by methods described herein, silk fibroin assumes a predominantly beta-sheet conformation. As already noted, this configuration is believed to be responsible for the strength and elasticity of silk material. It is now recognized by the inventors of the present invention that the beta-sheet configuration also provides extraordinary surface smoothness of silk materials, including silk film. This unique property of silk-based materials makes it possible for silk to serve as the "glue" at the interface between a biological surface and a high-technology element.

Previously, one of the technical challenges in fashioning a bio-high tech device was the lack of suitable medium that could stably bridge a biological surface (e.g., cells or soft tissues) with a nano-scale high technology components, such as optical and electronic devices.

The present inventors have now discovered that silk-based materials can be used to provide an extraordinary smooth surface at the nano- and micro-scale which can form an interface between biological and high technology elements. As described in more detail below, the methods described herein can be used to make and use a wide variety of biocompatible devices comprising high tech components such as sensors and resonators.

Degradation Properties of Silk-Based Materials

Additionally, as will be appreciated by those of skill in the art, much work has established that researchers have the ability to control the degradation process of silk. According to the present invention, such control can be particularly valuable in the fabrication of electronic components, and particularly of electronic components that are themselves and/or are compatible with biomaterials. Degradability (e.g., bio-degradability) is often essential for biomaterials used in tissue engineering and implantation. The present invention encompasses the recognition that such degradability is also relevant to and useful in the fabrication of silk electronic components.

According to the present invention, one particularly desirable feature of silk-based materials is the fact that they can be programmably degradable. That is, as is known in the art, depending on how a particular silk-based material is prepared, it can be controlled to degrade at certain rates. Degradability and controlled release of a substance from silk-based materials have been published; see, for example, WO 2004/080346, WO 2005/012606, WO 2005/123114, WO 2007/016524, WO 2008/150861, WO 2008/118133, each of which is incorporated by reference herein.

Control of silk material production methods as well as various forms of silk-based materials can generate silk compositions with known degradataion properties. For example, using various silk fibroin materials (e.g., microspheres of approximately 2 μm in diameter, silk film, silk hydrogels) entrapped agents such as therapeutics can be loaded in active form, which is then released in a controlled fashion, e.g., over the course of minutes, hours, days, weeks to months. It has been shown that layered silk fibroin coatings can be used to coat substrates of any material, shape and size, which then can be used to entrap molecules for controlled release, e.g., 2-90 days.

As noted above, crystalline silk materials can show unusual surface smoothness. According to the present invention, silk materials showing surface smoothness within the range of, for example, about 1 nm to 10 nm, are particularly useful in the fabrication of electronic components as described herein.

Crystalline Silk Materials

As known in the art and as described herein, silk proteins can stack with one another in crystalline arrays. Various properties of such arrays are determined, for example, by the degree of beta-sheet structure in the material, the degree of cross-linking between such beta sheets, the presence (or absence) of certain dopants or other materials.

In many embodiments, one or more of these features is intentionally controlled or engineered to achieve particular characteristics of a silk matrix.

In many embodiments, the present invention utilizes a crystalline silk material (e.g., not an amorphous material).

Is some embodiments, crystalline silk materials for use in accordance with the present invention are characterized by having smooth surface morphology, adhesive to conductive materials such as metal, and conforms to biological materials.

Additional Elements

In some embodiments, provided silk electronic components include one or more other elements in addition to a silk matrix and a patterned conductive structure.

One or more additional elements of silk electronic components for example may be a dopant or doping agent. The art is familiar with such agents.

For example, in some embodiments, one or more additional elements is present in or on the silk matrix. In some embodiments, one or more additional elements is distributed throughout the silk matrix. In other embodiments, one or more additional elements is distributed unevenly within the silk matrix. In some embodiments, uneven distribution of one or more additional elements form a gradient within the silk matrix. In some embodiments, one or more additional elements is localized to one or more portions within the silk matrix.

In some embodiments, a provided silk electronic component comprises one or more additional polymer elements. In some embodiments, such a polymer element is or comprises a biological polymer (e.g., a protein or nucleic acid). In some embodiments, such a polymer element does not comprise, or does not include, a biological polymer. In some embodiments, a provided silk electronic component does not include any polymer other than silk.

In some embodiments, a provided silk electronic component comprises one or more polypeptides or proteins. In some embodiments, a provided electronic component comprises one or more enzymes. In some embodiments, a provided silk electronic component comprises one or more antibodies.

In some embodiments, a provided silk electronic component comprises one or more pharmacologic agents.

In some embodiments, one or more active agents can be combined in silk fibroin solution for further processing into silk matrix, or can be otherwise introduced into a silk matrix or composition. The variety of active agents that can be used in conjunction with the silk matrix of the invention is vast. For example, the active agent may be a therapeutic agent or biological material, such as cells, proteins, peptides, nucleic acid analogues, nucleotides, oligonucleotides, nucleic acids (DNA, RNA, siRNA), peptide nucleic acids, aptamers, antibodies or fragments or portions thereof, hormones, hormone antagonists, growth factors or recombinant growth factors and fragments and variants thereof, cytokines, enzymes, antibiotics or antimicrobial compounds, anti-inflammation agent, antifungals, antivirals, toxins, prodrugs, chemotherapeutic agents, small molecules, drugs (e.g., drugs, dyes, amino acids, vitamins, antioxidants) and combinations thereof.

Exemplary antibiotics suitable for inclusion in the silk ionomer composition of the invention include, but are not limited to, aminoglycosides (e.g., neomycin), ansamycins, carbacephem, carbapenems, cephalosporins (e.g., cefazolin, cefaclor, cefditoren, cefditoren, ceftobiprole), glycopeptides (e.g., vancomycin), macrolides (e.g., erythromycin, azithromycin), monobactams, penicillins (e.g., amoxicillin, ampicillin, cloxacillin, dicloxacillin, flucloxacillin), polypeptides (e.g., bacitracin, polymyxin B), quinolones (e.g., ciprofloxacin, enoxacin, gatifloxacin, ofloxacin, etc.), sulfonamides (e.g., sulfasalazine, trimethoprim, trimethoprim-sulfamethoxazole (co-trimoxazole)), tetracyclines (e.g., doxycyline, minocycline, tetracycline, etc.), chloramphenicol, lincomycin, clindamycin, ethambutol, mupirocin, metronidazole, pyrazinamide, thiamphenicol, rifampicin, thiamphenicl, dapsone, clofazimine, quinupristin, metronidazole, linezolid, isoniazid, fosfomycin, and fusidic acid.

Exemplary cells suitable for use herein include, but are not limited to, progenitor cells or stem cells, smooth muscle cells, skeletal muscle cells, cardiac muscle cells, epithelial cells, endothelial cells, urothelial cells, fibroblasts, myoblasts, chondrocytes, chondroblasts, osteoblasts, osteoclasts, keratinocytes, hepatocytes, bile duct cells, pancreatic islet cells, thyroid, parathyroid, adrenal, hypothalamic, pituitary, ovarian, testicular, salivary gland cells, adipocytes, and precursor cells.

Exemplary antibodies include, but are not limited to, abciximab, adalimumab, alemtuzumab, basiliximab, bevacizumab, cetuximab, certolizumab pegol, daclizumab, eculizumab, efalizumab, gemtuzumab, ibritumomab tiuxetan, infliximab, muromonab-CD3, natalizumab, ofatumumab omalizumab, palivizumab, panitumumab, ranibizumab, rituximab, tositumomab, trastuzumab, altumomab pentetate, arcitumomab, atlizumab, bectumomab, belimumab, besilesomab, biciromab, canakinumab, capromab pendetide, catumaxomab, denosumab, edrecolomab, efungumab, ertumaxomab, etaracizumab, fanolesomab, fontolizumab, gemtuzumab ozogamicin, golimumab, igovomab, imciromab, labetuzumab, mepolizumab, motavizumab, nimotuzumab, nofetumomab merpentan, oregovomab, pemtumomab, pertuzumab, rovelizumab, ruplizumab, sulesomab, tacatuzumab tetraxetan, tefibazumab, tocilizumab, ustekinumab, visilizumab, votumumab, zalutumumab, and zanolimumab.

In some embodiments, silk electronic components of the present invention further comprises a polypeptide (e.g., protein), including but are not limited to: one or more antigens, cytokines, hormones, chemokines, enzymes, and any combination thereof.

Exemplary enzymes suitable for use herein include, but are not limited to, peroxidase, lipase, amylose, organophosphate dehydrogenase, ligases, restriction endonucleases, ribonucleases, DNA polymerases, glucose oxidase, laccase, and the like.

Additional or alternative active agents suitable for use herein include cell growth media, such as Dulbecco's Modified Eagle Medium, fetal bovine serum, non-essential amino acids and antibiotics; growth and morphogenic factors such as fibroblast growth factor, transforming growth factors, vascular endothelial growth factor, epidermal growth factor, platelet derived growth factor, insulin-like growth factors), bone morphogenetic growth factors, bone morphogenetic-like proteins, transforming growth factors, nerve growth factors, and related proteins (growth factors are known in the art, see, e.g., Rosen & Thies, CELLULAR & MOLECULAR BASIS BONE FORMATION & REPAIR (R. G. Landes Co., Austin, Tex., 1995)); anti-angiogenic proteins such as endostatin, and other naturally derived or genetically engineered proteins; polysaccharides, glycoproteins, or lipoproteins; anti-infectives such as antibiotics and antiviral agents, chemotherapeutic agents (i.e., anticancer agents), anti-rejection agents, analgesics and analgesic combinations, anti-inflammatory agents, and steroids.

In some embodiments, an active agent may also be an organism such as a bacterium, fungus, plant or animal, or a virus. In some embodiments, an active agent may include or be selected from neurotransmitters, hormones, intracellular signal transduction agents, pharmaceutically active agents, toxic agents, agricultural chemicals, chemical toxins, biological toxins, microbes, and animal cells such as neurons, liver cells, and immune system cells. The active agents may also include therapeutic compounds, such as pharmacological materials, vitamins, sedatives, hypnotics, prostaglandins and radiopharmaceuticals.

An active agent for use in accordance with the present invention may be an optically or electrically active agent, including but not limited to, chromophores; light emitting organic compounds such as luciferin, carotenes; light emitting inorganic compounds, such as chemical dyes; light harvesting compounds such as chlorophyll, bacteriorhodopsin, protorhodopsin, and porphyrins; light capturing complexes such as phycobiliproteins; and related electronically active compounds; and combinations thereof.

Overview of Patterned Conductive Structures

A silk matrix can support one or more patterned conductive structures. The combination of the silk matrix and patterned conductive structure can exhibit a unique electromagnetic signature. Many factors can influence the electromagnetic signature. Exemplary factors include, but are not limited to, the geometry of the patterned conductive structure, dielectric properties of the patterned conductive structure and/or silk matrix, and dopants in the silk matrix.

In some embodiments, the electromagnetic signature can change when a change occurs in the dielectric constant of the silk matrix, the silk matrix with dopants, and/or the patterned conductive structure. Such a change can be induced by chemical, biochemical, or other environmental factors, such as temperature, mechanical strain, gas concentration, gas release, chemical reactions (e.g., surface reactions, bulk reactions), hydration, and/or material removal.

In some embodiments, material phase changes in the silk matrix (e.g., controlled dissolution, heating, melting, surface binding) can influence the electromagnetic signature. In some embodiments, material reconfiguration of the silk matrix and patterned conductive structures (e.g., stretching, contraction, bending, and/or folding of the silk matrix) can influence the electromagnetic signature. In some embodiments, a change can shift the resonance frequency of the electromagnetic signature to another frequency. For example, the change can shift the resonance frequency to higher or lower frequencies. In some embodiments, a change can modulate the amplitude of the resonant response of the electromagnetic signature. In some embodiments, a change can shift the resonance frequency and modulate the amplitude of the resonant response of the electromagnetic signature. In some embodiments, the change can alter the width of a feature of the electromagnetic signature (e.g., the full width at half maximum of the spectral response).

By controlling the geometry of patterned conductive structures, the dopants in the silk matrix, or various other factors, a user can design a silk matrix with patterned conductive structures that exhibits desired electromagnetic responses at target frequencies. In some embodiments, the user can design a silk matrix with patterned conductive structures that exhibits desired electromagnetic responses at target frequencies in response to an environmental factor.

Examples of Patterned Conductive Structures

A patterned conductive structure can be a structure with a user-designed electromagnetic response. In some embodiments, the patterned conductive structure is or comprises a source, lens, switch, modulator, detector, or any combination thereof. In some embodiments, the patterned conductive structure is or comprises an antenna. In some embodiments, the patterned conductive structure is or comprises a radiofrequency identification (RFID) device. In some embodiments, the patterned conductive structure is or comprises a metamaterial structure.

In some embodiments, the patterned conductive structure is or comprises an electrode. In some embodiments, the patterned conductive structure is or comprises a passive electronic. In some embodiments, the patterned conductive structure is or comprises a thin film semiconductor component. In some embodiments, the patterned conductive structure is or comprises a solar cell. In some embodiments, the patterned conductive structure is or comprises a capacitor, inductor, or resistor.

In some embodiments, the patterned conductive structure is or comprises a light emitting diode (LED). In some embodiments, the patterned conductive structure is or comprises a transistor. In some embodiments, the patterned conductive structure is or comprises a conductive coil. In some embodiments, the patterned conductive structure is or comprises a coil that receives power. In some embodiments, the patterned conductive structure is or comprises a photodetector. In some embodiments, the patterned conductive structure is or comprises a vertical cavity surface emitting laser (VCSEL). In some embodiments, the patterned conductive structure is or comprises a thin-film electronic. In some embodiments, the patterned conductive structure is or comprises a resonator cavity.

Figure 2:
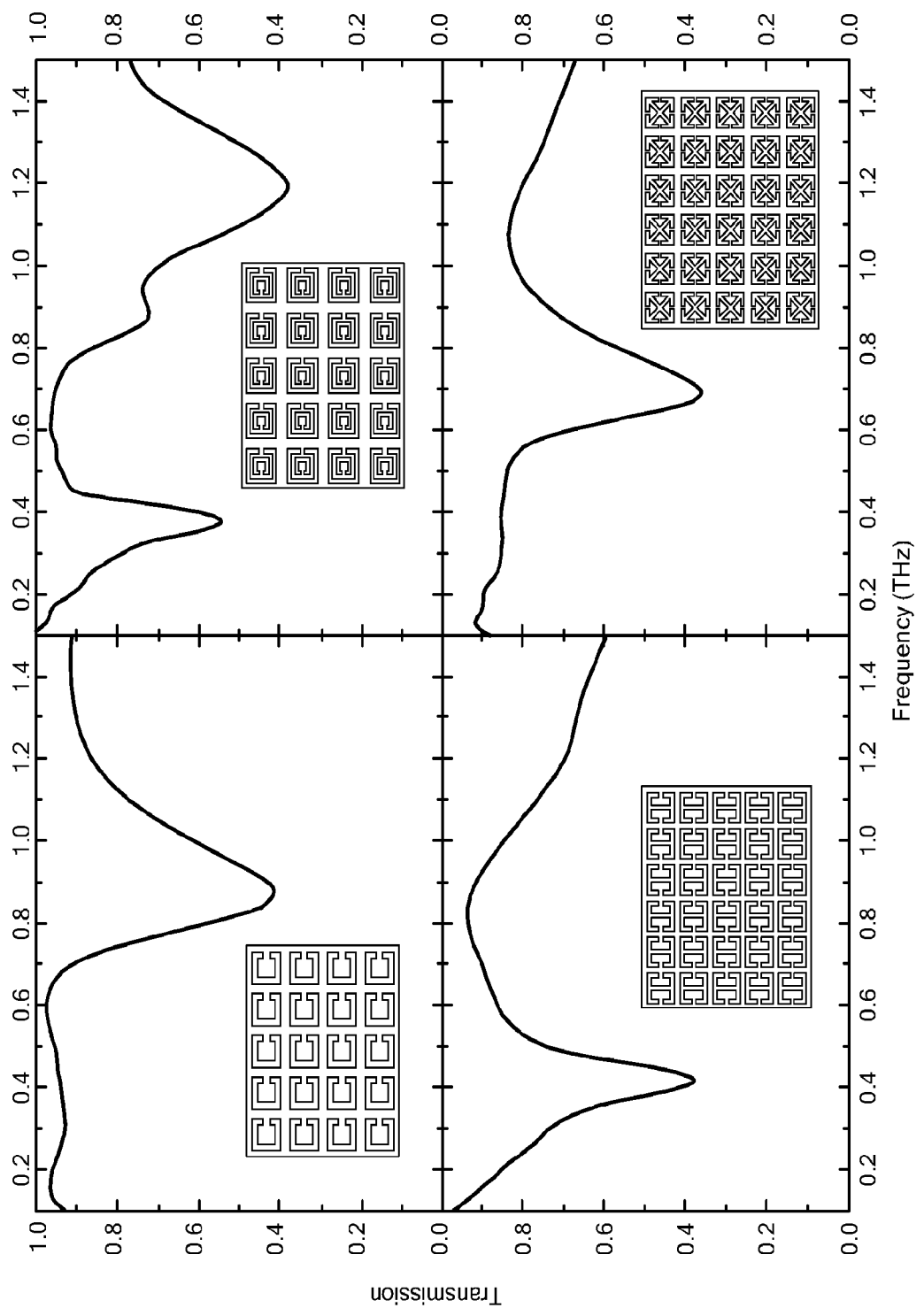

In some embodiments, the patterned conductive structure is or comprises a resonator. A resonator can be a magnetic or electric resonator. Exemplary electric resonators include split-ring resonators (SRR), polarization-sensitive electric resonators, polarization non-sensitive electric resonators, or combinations thereof. Exemplary patterns for resonators and their electromagnetic signatures are depicted in FIGS. 1 and 2. The exemplary patterns can differ from one another by the number of gaps, placement of the gaps, distance between gaps, and/or thickness of line width, any combination thereof, or any other factor as would be appreciated by one of ordinary skill in the art. The differences in the geometries of the resonators can affect their electromagnetic signatures.

In some embodiments, a patterned conductive structure can be disposed on a silk matrix. For example, a patterned conductive structure can be spray-deposited on a surface of a silk matrix. In another example, a patterned conductive structure can be transferred by contact from a substrate to a surface of a silk matrix. In some embodiments, a patterned conductive structure can be embedded in a silk matrix. For example, a patterned conductive structure can be formed on a substrate, and a silk fibroin solution can be spun onto the substrate. The silk proteins can self-assemble into a matrix around the patterned conductive structure, thereby embedding the conductive material (e.g., metal) within the matrix.

In some embodiments, the patterned conductive structures comprise a layer of conductive material. In some embodiments, the patterned conductive structures comprise more than one layer of conductive material. The patterned conductive structures can have dimensions of any size. For example, dimensions of the patterned conductive structures can be on the order of micrometers or nanometers. Exemplary dimensions include structures that measure 10 µm×10 µm, 50 µm×50 µm, 100 µm×100 µm, 4 cm×4 cm, or 6 cm×6 cm in their entirety, although other dimensions may be used. In some embodiments, features of the patterned conductive structure can measure 200-500 nm along a dimension. In some embodiments, features of the patterned conductive structure can measure 200-500 nm along a dimension. Features of other sizes can be used.

The geometry of patterned conductive structures can be scaled to create a larger or smaller structure. For example, a pattern for a conductive structure can be scaled from an order of micrometers to an order of nanometers, or the reverse.

In any of the embodiments described herein, parameters of the patterned conductive structures and/or silk matrices can be varied. For example, the thickness of the structures, the thickness of the silk matrix, the filling factor and/or orientation of the structures, the spacing between structures, the conductivity of the material used, and/or the geometry of the structures can be varied.

Behaviors of Patterned Conductive Structures

In some embodiments, a patterned conductive structure can respond to electromagnetic radiation at a desired wavelength or range of wavelengths. Exemplary wavelengths include microwave, infrared, visible, and/or ultraviolet wavelengths. In response to the radiation, a patterned conductive structure can exhibit an electromagnetic signature at a targeted frequency or range of frequencies. In some embodiments, the electromagnetic signature can exhibit notable features (e.g., peaks, troughs, known patterns involving peaks and troughs) at terahertz (THz), megahertz (MHz), and/or petahertz (PHz) frequencies. The electromagnetic signature can include a resonant electromagnetic response. The response can include the amplitude and phase of the transmission, reflection, and/or absorption of electromagnetic radiation at various frequencies, including the resonance frequency.

In some embodiments, at least one dimension of a patterned conductive structure can be as small as or smaller than a wavelength of incident electromagnetic radiation. For example, for visible light with wavelengths shorter than one micrometer (e.g., 560 nanometers for sunlight), a dimension of a patterned conductive structures can be less than the 560 nanometers, or even 280 nanometers. For microwave radiation, dimensions of a patterned conductive structure can be on the order of one decimeter.

Figure 3:
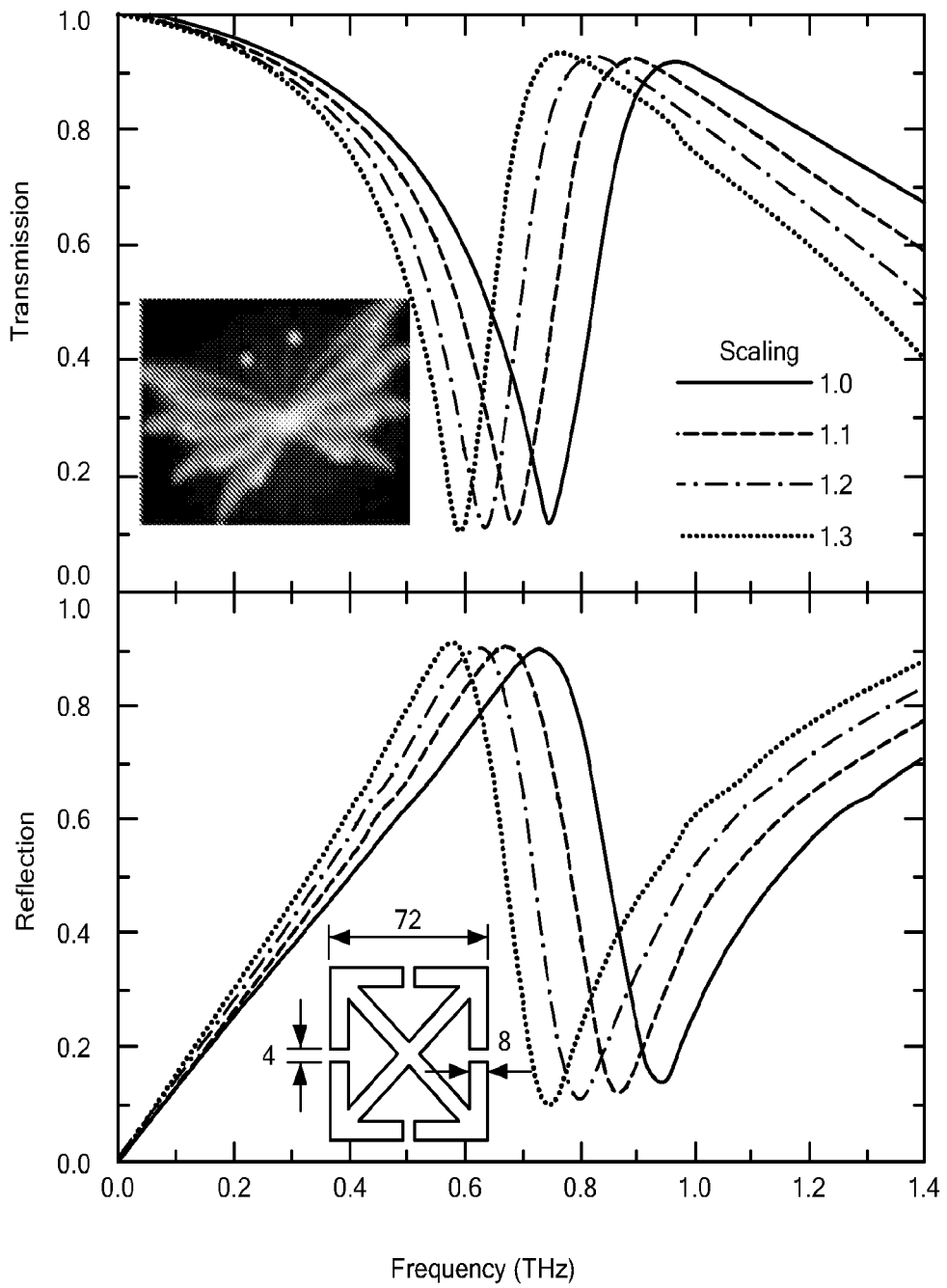
FIG. 3 shows electromagnetic signatures of split-ring resonators scaled to different sizes.

In some embodiments, a patterned conductive structure can respond to electromagnetic radiation according to the structure's geometric scale. In some embodiments, a patterned conductive structure can respond to infrared radiation. When the structure is geometrically scaled, the scaled structure can respond to microwave or ultraviolet radiation, instead of infrared radiation. In some embodiments, a structure geometrically scaled to be smaller can response to shorter wavelengths of electromagnetic radiation. For example, a patterned conductive structure can be on the order of a wavelength or half-wavelength of incident electromagnetic radiation. In some embodiments, patterned conductive structures of about 400 nm respond to visible radiation. In some embodiments, patterned conductive structures of about 1 µm respond to infrared radiation. FIG. 3 depicts electromagnetic signatures of a split-ring resonator when the resonator is scaled to be larger or smaller.

In some embodiments, patterned conductive structures (e.g., resonators) can be conduits for resonant electromagnetic modes. For example, a 30 µm ring resonator can support THz modes. Ring resonators on the order of several cm can support GHz modes. Ring resonators on the order of tens of cm can support MHz modes.

In some embodiments, dopants in the silk matrix can change dielectric properties of the silk matrix and/or the patterned conductive structure. Thus, dopants can change the intensity and/or amplitude of transmitted, reflected, and/or absorbed electromagnetic radiation. An exemplary dopant is or comprises horseradish peroxidase (HRP). When a silk matrix doped with HRP is exposed to teramethylbenzidine (TMB), the electromagnetic signature of patterned conductive structures on the doped silk matrix can shift to lower frequencies. The dopants can change the resonance frequency of the patterned conductive structures. In some embodiments, portions of the patterned conductive structures can be removed to alter the electromagnetic responses of the structures.

Figure 4:
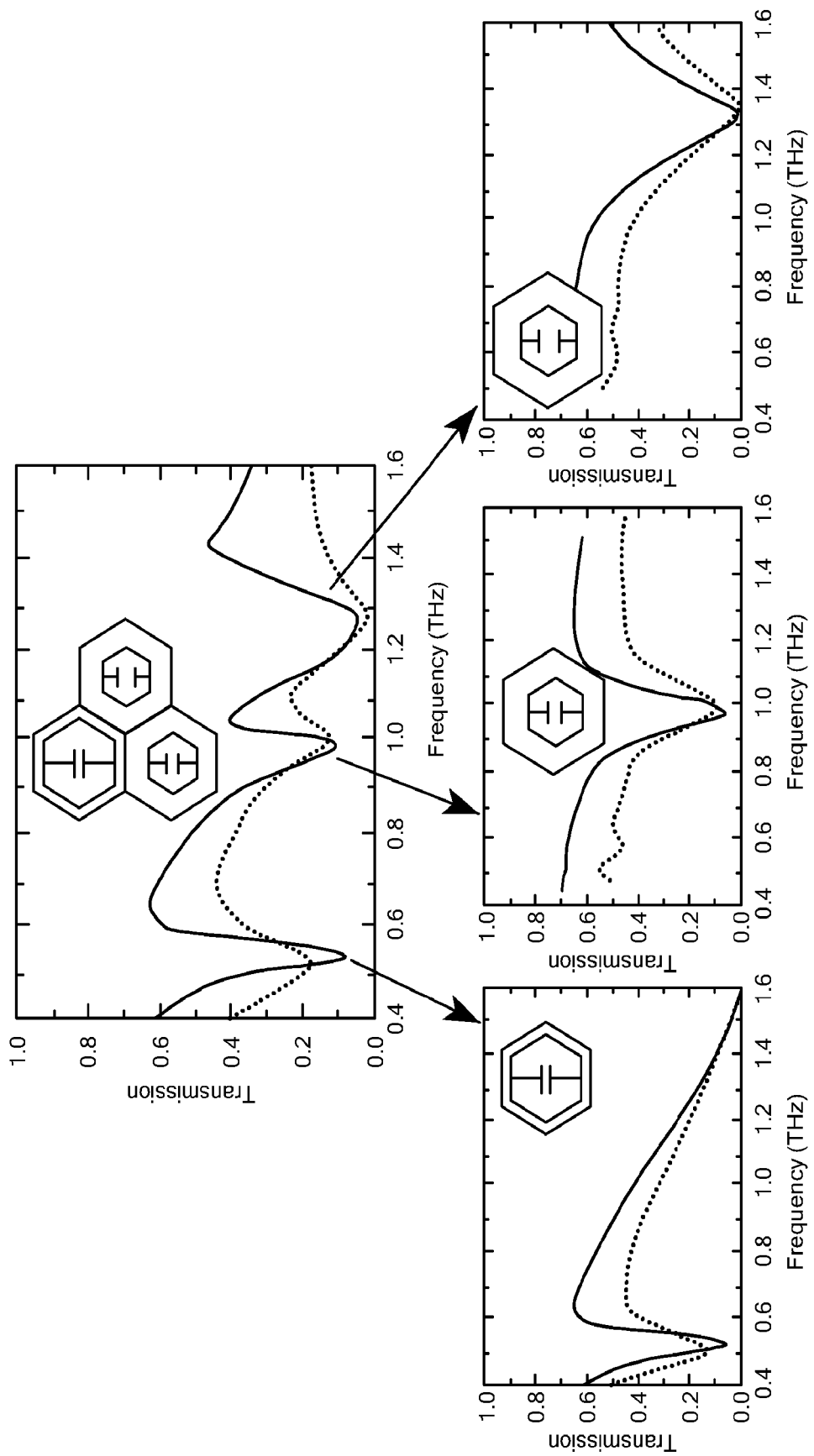
FIG. 4 shows electromagnetic signatures of resonators whose signatures can be superimposed to mimic a molecule.

In some embodiments, each patterned conductive structure can exhibit its own electromagnetic signature. When structures are patterned on the same silk matrix, the individual responses of the structures can be superimposed to yield a collective, broadband response for the structures. For example, as depicted in FIG. 4, resonators with different electromagnetic responses in the terahertz range can be fabricated on a single silk matrix. The responses of the resonators can be superimposed to create a silk matrix with patterned conductive structures that mimics the electromagnetic response of a biological molecule, such as biotin.

In some embodiments, the electromagnetic response of the patterned conductive structures can originate from oscillating electrons in the conductive material (e.g., metal). The oscillations can permit the design of a specific resonant response according to the electrical permittivity ($\in$) or magnetic permeability ($\mu$) of the patterned conductive structure.

In some embodiments, a resonator, such as an SRR, can exhibit a resonant magnetic or electric response to achieve an effective negative permeability ($\mu$) at a frequency range above the resonance frequency. A resonator can exhibit a resonant response to the electric component of a light field when the electric field is aligned perpendicular to the resonator gap to excite the circulating currents within the resonator, resulting in effective negative permittivity ($\in$).

In some embodiments, an SRR can be modeled as a LC resonator (i.e., a resonant circuit with an inductor and a capacitor). The resonance frequency of the SRR can be represented as $\omega_0 \sim \sqrt{1/LC}$, wherein the inductance can result from the current path of the SRR and capacitance can be determined by the split gap and the dielectric properties of the silk matrix and other elements in the gap. A change in the capacitance or inductance can change the SRR's resonant response. As an SRR can be sensitive to its environment, an SRR can be suitable for integration into devices for sensing and detecting applications.

In some embodiments, terahertz time-domain spectroscopy (THz-TDS) can be used to characterize the electromagnetic signature of the patterned conductive structures on a silk matrix. The measurements can be performed at room temperature in a dry (<0.1% humidity) air atmosphere. The transmission of the THz electric field can be measured for a sample and a reference respectively, with the reference being air in this example. The amplitude and phase of the electric field spectral can be calculated through Fourier transformation of the time-domain pulses. The spectral transmission can be obtained by dividing the transmission of the sample by the transmission of the reference, as illustrated in the inset of FIG. 5.

Figure 5:
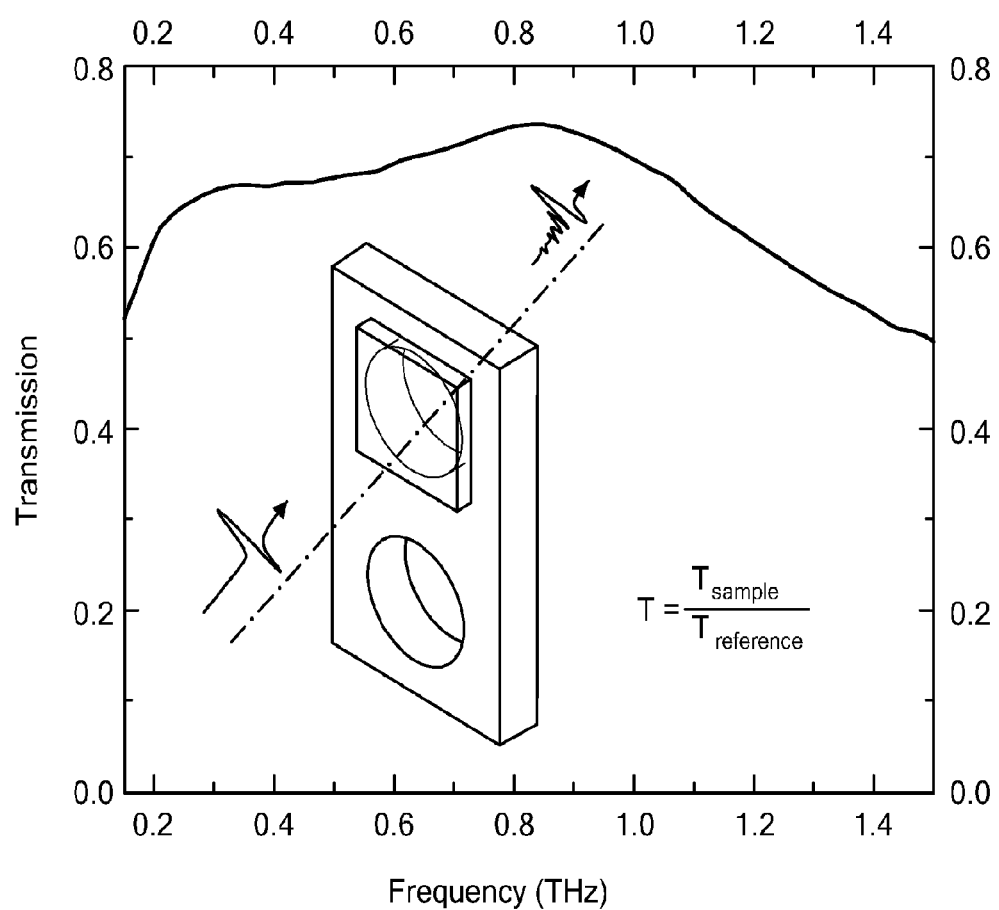
FIG. 5 is a graph characterizing the field transmission of pure silk films, 80-μm thick, as a function of frequency ranging from 0.15 THz to 1.5 THz, measured by THz time-domain spectroscopy. The inset of the graph is a schematic showing the transmission measurements of a sample (top hole) and a reference (bottom hole) and the calculation of the spectral transmission through dividing the transmission of the sample by the transmission of the reference.

THz-TDS measurements can be carried out on a series of 80 μm thick pure silk matrices, which can show high field transmission of ~60% of terahertz radiation in the range from about 0.2 THz to about 1.5 THz, as shown in FIG. 5. In some embodiments, the refractive index of the pure silk films can be n=1.91+i0.12, from 0.15 THz to 1.5 THz.

In some embodiments, split ring resonators, polarization non-sensitive electric resonators, and polarization sensitive electric resonators can be fabricated and characterized with THz-TDS measurements. For example, a first sample can be a single split ring resonators (Sample No. 1), a second sample can be a polarization non-sensitive electric resonator (Sample No. 2), and a third sample can be a polarization sensitive electric resonator (Sample No. 3). Sample No. 1 can have dimensions of 50 μm×50 μm. Samples No. 2 and Sample No. 3 can have dimensions of 100 μm×100 μm. The samples can be diced into 1 cm×1 cm squares and mounted at normal incidence to the THz beam with the electric field perpendicular to the SRR gap.

Figure 6A:
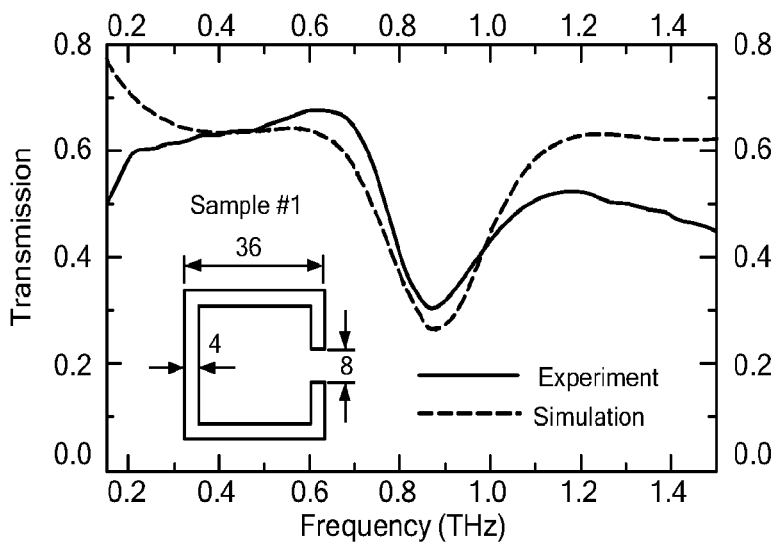
FIG. 6A-6C are graphs depicting the experimental (black solid lines) and simulation (red dash lines) transmission spectra of the silk metamaterial composites as a function of frequency ranging from 0.15 THz to 1.5 THz. The electric field (E) is aligned perpendicular to the split ring resonator (SRR) gap. The insets of the graphs show the design and unit cell dimension of the different SRR elements.
Figure 6B:
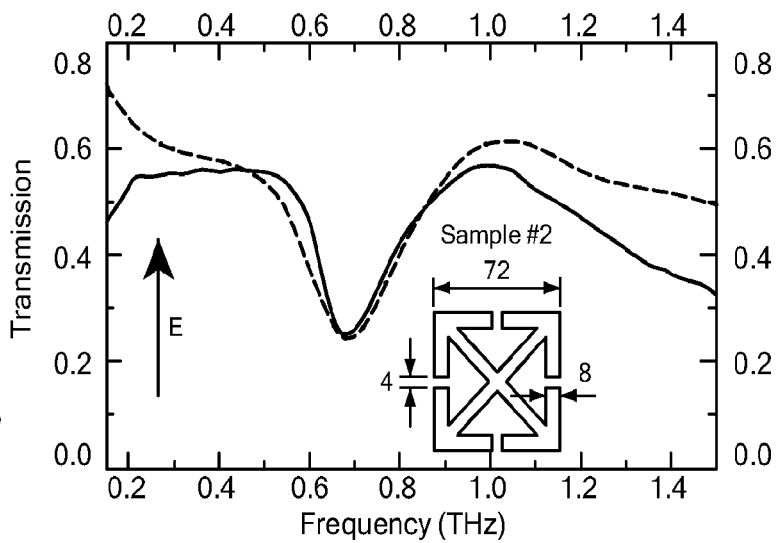
Figure 6C:
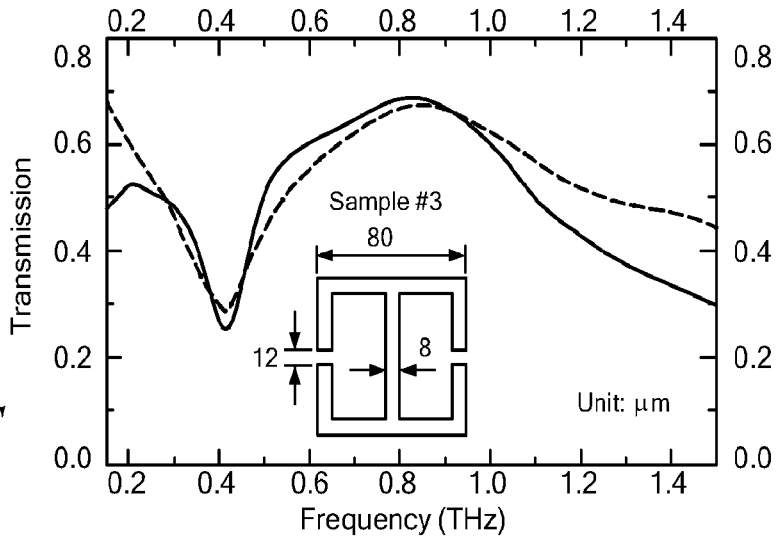

FIG. 6 depicts experimental and simulation results of the samples. The black solid lines show the experimentally measured field transmission as a function of frequency. The red dash lines are the results of electromagnetic simulations using CST Microwave Studio™ 2008 (CST Computer Simulation Technology AG, Darmstadt, Germany). In the electromagnetic simulations, the dimensions shown in FIG. 6 were used for the resonator elements and the experimentally measured refractive index for silk matrices (n=1.91+i0.12) was used.

As shown in FIG. 6, the experimental results are in reasonable agreement with the simulation data, although noticeable off-resonance disagreement occurs consistently in all three samples, which may arise partly from the fabrication imperfections and the surface roughness of the samples. As expected from simulation results, Sample No. 1, having smaller dimensions than Sample No. 2 and Sample No. 3, presents a higher resonance frequency (0.85 THz) than those of Sample No. 2 (0.7 THz) and Sample No. 3 (0.4 THz).

Fabrication

Patterned conductive structures can be fabricated on silk matrices with patterning techniques that can avoid prolonged times of sample preparation, elevated temperature, and/or high vacuums. Such patterning techniques can be inexpensive. Pattern techniques can be performed at ambient temperature and pressure conditions, thereby preserving the functionality of biological dopants in silk matrices. Exemplary temperatures include 40° C. or lower. Exemplary pressures include 700-800 mTorr. Another exemplary pressure is 760 mTorr.

In some embodiments, the patterned conductive structures can be formed by spray deposition. Spray deposition techniques have optimal performance when applied to substrates with high degrees of smoothness. As the silk matrices of the present disclosure exhibit high levels of smoothness and superior levels of smoothness compared to other biopolymers, the silk matrices can facilitate the direct spraying of large area patterns with good uniformity.

A shadow mask can be attached to the silk matrix. In some embodiments, the shadow mask can be accurately positioned and/or fixed relative to the silk matrix via alignment under microscopy. In some embodiments, the shadow mask can be contact-positioned on a silk matrix, e.g., the shadow mask can be placed in contact with silk matrix and aligned and/or positioned without use of adhesives. In some embodiments, clamps and/or clips can secure contact between the shadow mask and the silk matrix. In some embodiments, the edges of the shadow mask can be attached to the silk matrix with tapes, by way of example.

A conductive material can be spray-deposited on the silk matrix through the shadow mask, thereby forming a patterned conductive structure or an array of patterned conductive structures on the matrix. The shadow mask can provide a predetermined geometry (e.g., structural features, patterns for the array) for the patterned conductive structures. After the conductive material is applied to the silk matrix, in some embodiments, the shadow mask can be removed without use of solvents or other treatments. For example, clamps and/or clips can be removed from the shadow mask and silk matrix. The shadow mask can be manually separated from the silk matrix. In some embodiments, the shadow mask can be removed by peeling off tape that attaches the shadow mask to the silk matrix. Then, a solvent can be applied to the silk matrix to remove residual adhesive material due to the tape.

In some embodiments, the shadow mask can be a stencil (e.g., a large area stencil, micro-stencil, nano-stencil). In some embodiments, the deposition can be used in combination with soft fabrication techniques (e.g., elastomeric stamps, molds, conformable photomasks).

Figure 7:
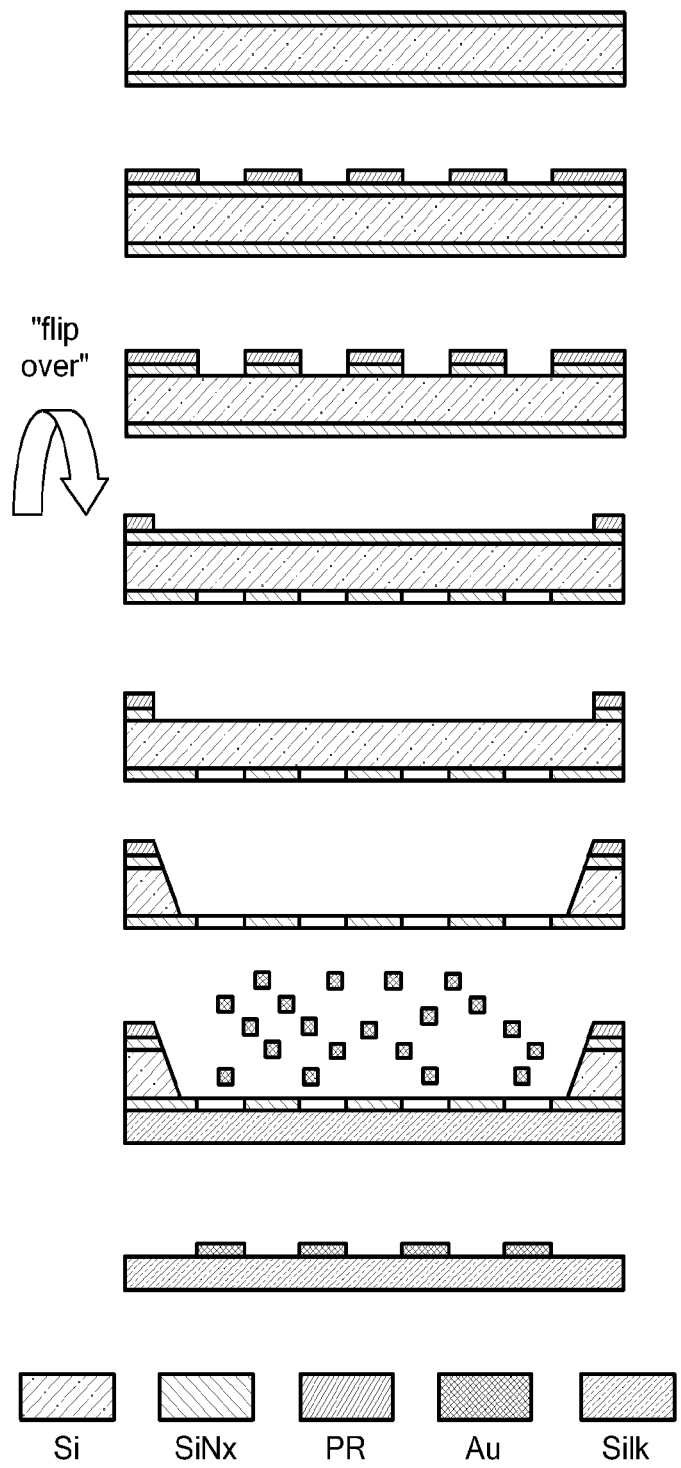
FIG. 7 is a scheme depicting the fabrication process of metamaterials on silk substrates using the shadow mask patterning technique.

Referring now to FIG. 7, a process of spraying metal on silk matrices to form patterned conductive structures is shown and described. First, micro-stencils with the desired patterns corresponding to the patterned conductive structures can be fabricated on a commercially purchased 4" silicon wafer. A 400 nm-thick low-stress silicon nitride (SiNx) film can be pre-deposited on both sides of the silicon wafer by low-pressure chemical vapor deposition (LPCVD). The patterns of resonators (e.g., SRRs) can be fabricated using standard UV photolithography followed by reactive ion etching (RIE) using Sulfur hexafluoride ($SF_6$) and Helium (He) at 110° C. for 6 minutes, with Microposit® S1813 photoresists placed on the top side of the silicon wafer as the etching mask to define the stencil patterns. The silicon wafer can be flipped over. Open windows for performing backside wet-etching can be patterned on the backside of the wafer using a similar process as described above. This process can be followed by backside wet-etching through rinsing the wafer in a stirred 25% concentrated KOH solution at 70° C. for a few hours. The suspended stencil structures can be released when KOH has etched through the wafer from the backside and reached the SiNx film on the top side. The stencils can be as large as a few $cm^2$ or even larger without an upper limit, depending on the quality of the pre-deposited SiNx film.

Inserts A and C of FIG. 8 depict exemplary fabricated micro stencils. Insert A depicts a 4" silicon wafer onto which a 7×7 stencil array has been patterned. The area of each stencil is approximately 1 cm×1 cm with a total area of SRR array being approximately 8 mm×8 mm in the center of the stencil. A 1 mm wide silicon frame was kept on the edges of the stencils as the supporting structure for later handling.

The micro stencils can be carefully attached to the 80 µm thick silk matrices in contact mode. The micro stencils can be aligned to the silk matrices under microscopy. The edges of the micro stencils can be attached to the silk matrices with scotch tapes. A thin layer of 100 nm thick gold can be sprayed on the silk matrices uniformly at a rate of ~3 Å/s. After spraying the metal layers, the micro stencils can be removed by peeling off the tape and releasing the silk matrices. The silk matrices with the patterned conductive structures can exhibit good uniformity, mechanical robustness, and flexibility. For example, the silk matrices with patterned conductive structures can be wrapped into a capsule-like cylinder with a diameter of ~3 mm with no distortion or cracking observed, as shown in Insert E of FIG. 8.

In some embodiments, the patterned conductive structures can be formed on a silk matrix via an evaporation process. A conductive material can be evaporated through the openings of the shadow mask to be deposited on the silk matrix. Exemplary evaporation processes include electron-beam evaporation and thermal evaporation, although any evaporation process known to one of ordinary skill in the art may be used. In some embodiments, the evaporation process can be controlled under 40° C., a safe temperature for maintaining the quality of the silk matrix. In some embodiments, the evaporation process can be repeated with different conductive materials and/or different shadow mask designs to create multi-layered patterns.

In some embodiments, the patterned conductive structures can be formed using inkjet printing, such as direct-write assembly. In some embodiments, the printing is filamentary. In some embodiments, the printing is droplet-based. A computer-controlled three-axis translation stage can control a syringe barrel that houses a conductive material (e.g., metal, metal solution). The syringe barrel can connect to one or more nozzles, such as fine deposition nozzles. Application of pressure to the syringe barrel can force the conductive material through a nozzle onto a silk matrix. A computer program can control the syringe barrel and nozzles to deposit the conductive material onto the silk matrix according to a geometric pattern for a conductive structure.

In some embodiments, the patterned conductive structures can be formed on a silk matrix via transfer by contact. A pattern can be formed on a substrate. In some embodiments, the pattern can be etched into the substrate. In some embodiments, the pattern can be elevated relative to a surface of the substrate. In some embodiments, the pattern can be cast onto the substrate. A conductive material can be deposited on the substrate to conform to the pattern. In some embodiments, a silk matrix (e.g., a free-standing silk matrix) can be applied to the substrate. In some embodiments, pressure can be applied to the silk matrix and substrate to transfer the deposited conductive material from the substrate to the silk matrix. The transfer by contact can occur under ambient pressure and/or temperature conditions.

In some embodiments, the substrate can be an elastomeric stamp or a composite elastomeric stamp. In some embodiments, the substrate can be a glass plate coated with polyimide-poly(methylmethacrylate) (PMMA). In some embodiments, the substrate can include teflon. In some embodiments, the substrate can include a hydrophobic material. Substrates can be coated with a hydrophobic material, such as triethoxysilane, trichlorovinylsilane, or trichlorosilane. In some embodiments, the substrate can be a silicon (Si) wafer.

The substrate can be treated with a silanizing agent to reduce the adhesion of the metal to a surface of the substrate, allow for pattern transfer to the silk matrix, and allow for manual detachment of the silk matrix from the substrate. Patterns can be deposited on the substratewafer via standard photolithography techniques, shadow masking techniques, or any other technique as would be appreciated by one of ordinary skill in the art.

In some embodiments, the patterned conductive structures can be formed on a silk matrix via casting. Casting on silk matrices of the present disclosure can be achieved under ambient pressure and/or temperature conditions, thereby allowing, if desired, biological dopants to be incorporated into the silk matrices while maintaining their biological functions. Casting can use patterned substrates such as the silicon wafers described in reference to the transfer by contact process.

Figure 9:
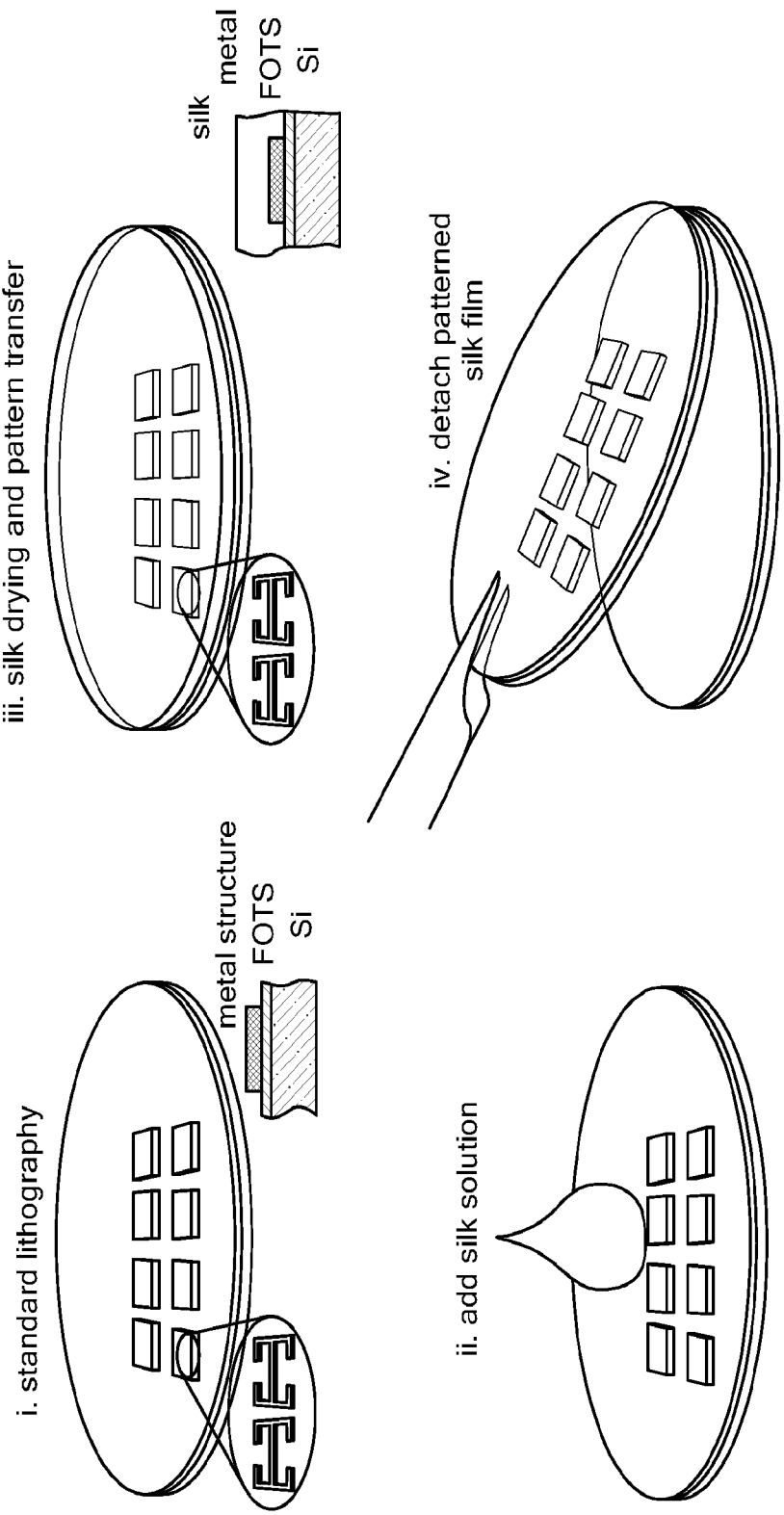
FIG. 9 shows an exemplary process that allows the direct transfer of patterned structures onto a surface of a silk matrix.

Referring now to FIG. 9, an exemplary process for casting patterned conductive structures onto a silk matrix is shown and described. An aqueous silk solution can be applied onto the patterned silicon wafer onto which metal has been deposited and/or a silanizing agent has been applied. The silk solution can dry (e.g., overnight) to form a silk matrix through self-assembly, by way of example. As the solution dries into a silk matrix, the silk proteins can bind to the metal deposited on the silicon wafer. Thus, the metal can be transferred from the silicon wafer onto the silk matrix to form the patterned conductive structures. The silk matrix can be manually detached from the silicon wafer. The patterned conductive structures can be examined by optical and/or scanning electron microscopy (SEM) to verify successful transfer with high-fidelity on the microscale.

In some embodiments, a 4" silicon wafer (e.g., a Nova wafer) can be treated with the silanizing agent tridecafluoro-1,1,2,2-tetrahydrooctyl trichlorosilane (FOTS), which can reduce sticking of deposited metal to the wafer. The silicon wafer can be placed in a vacuum chamber under a house vacuum with drops of the FOTS solution to evaporate for approximately 24 hours. A thin layer of metal (e.g., between about 100 nm and about 300 nm of aluminum or gold) can be sputtered onto the silicon wafer. Standard photolithography can be performed using photoresists, such as S1813 photoresist manufactured by Rohm & Haas. Residual metal can be wet etched in an etching solution. Remaining photoresist can be removed to reveal the patterned metal. 2 ml of an 8% wt/v silk solution can be evenly distributed over the silicon wafer surface and allowed to dry at room temperature over night. The silk matrix with the transferred patterned conductive structures can be removed from the silicon wafer using, e.g., a razor blade and tweezers, Patterned conductive structures formed via casting can be enhanced via dry etching (e.g., oxygen based reactive ion etching, or RIE). The transferred patterned conductive structures can function as masks (e.g., hard masks) for subsequent dry etching processes. The increased surface area and/or increased dielectric contrast of the patterned and etched structures can exhibit responses with higher sensitivity than non-etched patterned conductive structures. In some embodiments, a silk matrix with patterned conductive structures can be mounted with double sided adhesive copper tape to a cooled chuck to achieve thermal conductivity for the etching. Exemplary RIE conditions include 20 W plate power, <6 µTorr base pressure, and 20 minutes processing time.

Referring now to FIG. 10, the use of patterned conductive structures as a hard mask for subsequent RIE processes is shown and described. The oxygen plasma RIE etches away portions of the silk matrix not subject to the patterned conductive structures. Thus, the structures obtained from the etching process closely represent the metal patterns deposited on the surface of the matrix.

Figure 11:
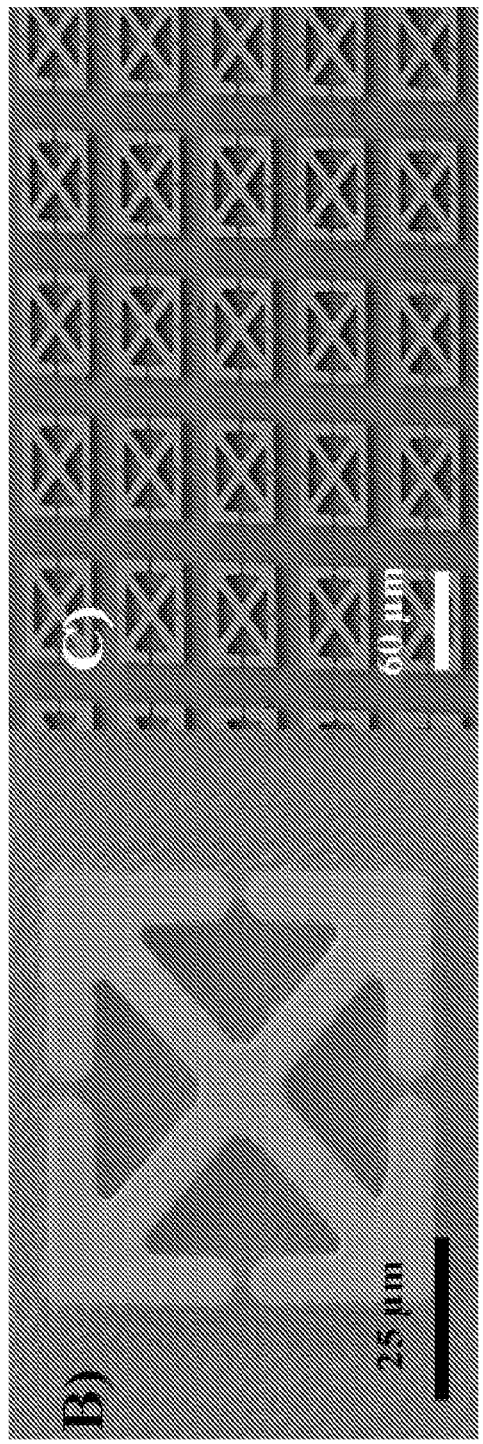
FIG. 11 shows a scanning electron microscope (SEM) image of an aluminum patterned conductive structure overlaying an RIE etched structure.
Figure 12:
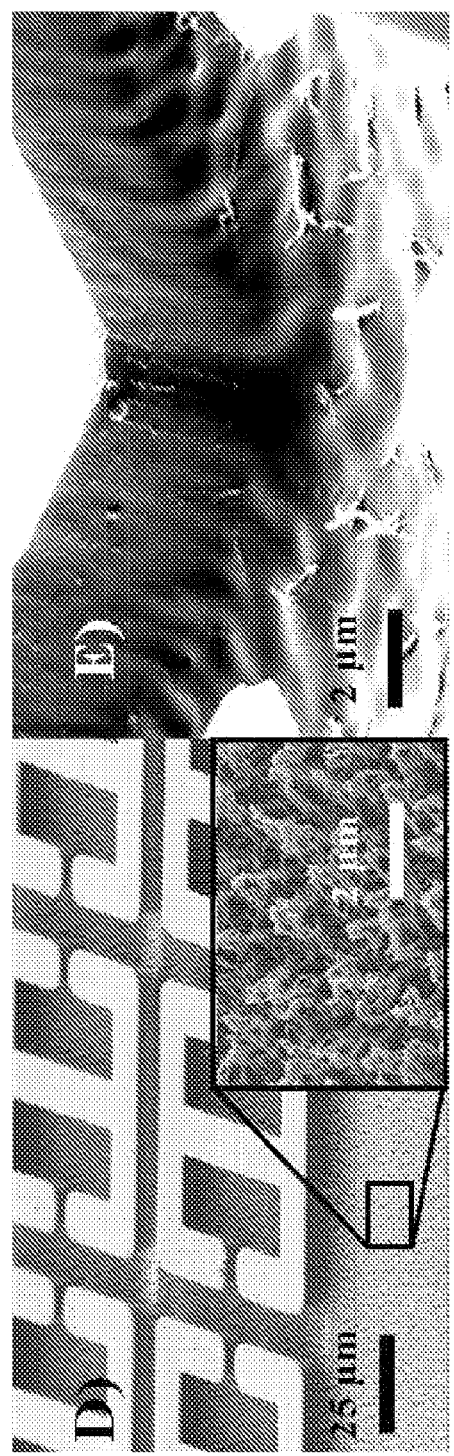
FIG. 12 shows a SEM image of gold patterned conductive structures (e.g., SRR) overlaying an RIE etched structure. The dimensions of these structures were approximately 6 μm at the gap of each resonator.

FIG. 11 depicts a scanning electron microscope (SEM) image of an aluminum patterned conductive structure overlaying an RIE etched structure. FIG. 11 also depicts a SEM image of an array of aluminum patterned conductive structures overlaying RIE etched structures (e.g., resonators). The structures produced by casting and subsequent RIE processing are consistent over the 100×100 SRR array. FIG. 12 depicts a SEM image (lefthand side) of gold patterned conductive structure (e.g., SRR) overlaying an RIE etched structure. The dimensions of these structures were approximately 6 μm at the gap of each resonator.

The conductive material used for the patterns can affect the surface structures obtained during RIE processing. For example, aluminum-coated structures depicted on the righthand side of FIG. 12 can exhibit smoother surfaces than gold-coasted structures, depicted in the insert in the lefthand side of FIG. 12. Conductive materials with higher resistance to sputtering and/or lower likelihood of inducing micro masking effects can result in structures with smoother surfaces. In some embodiments, the conductive metal is or comprises chromium.

Figure 13:
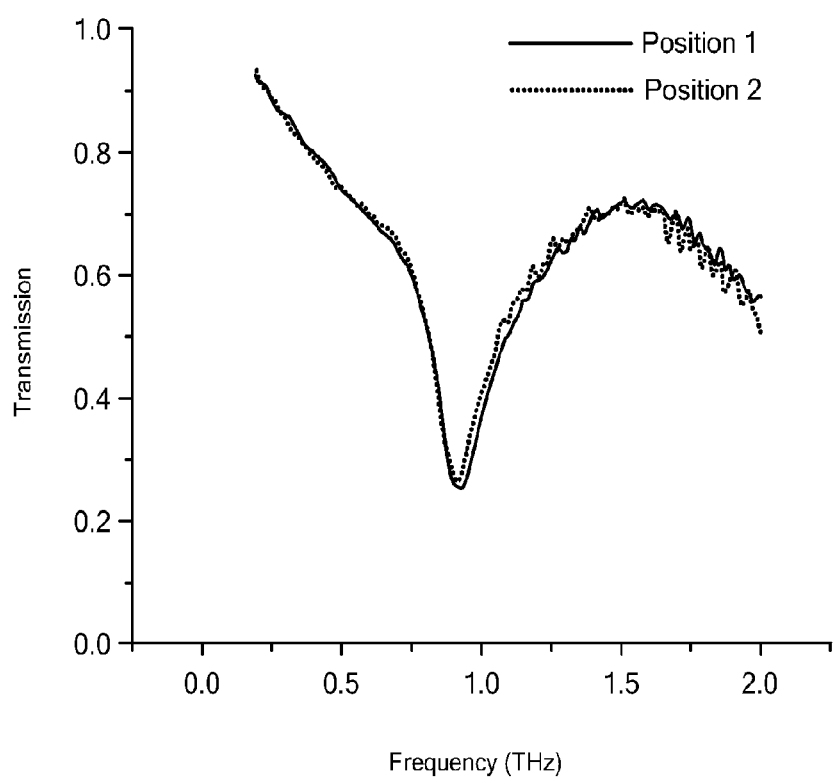
FIG. 13 shows the electromagnetic response of patterned aluminum structures that have been subjected to further RIE processing.

FIG. 13 depicts the electromagnetic response of patterned aluminum structures that have been subjected to further RIE processing. The electromagnetic transmission spectrum corresponds to the aluminum- and gold-patterned structures of FIGS. 11 and 12. The structures were analyzed by terahertz time-domain spectroscopy (THz-TDS). The strong resonance response detected near 1 THz suggests the functionality and integrity of the structures after the RIE processing. The THz beam was directed at the center of an 8 mm×8 mm RIE-etched patterned area, probing the resonance response and verify the consistency for two orthogonal polarizations. The resonance response can be sensitive to changes in the structures' dimensions, indicating small manufacturing tolerances. The effect of the electromagnetic frequency on the transmission did not vary for the two polarizations (correlation coefficient r>0.99, p<0.001), indicating excellent symmetry of the structures and corroborating fabrication consistency.

In some embodiments, the patterned conductive structures can be formed on a silk matrix via various lithography processes. Such lithography processes can include processes commonly applied to substrates, such as silicon. Exemplary lithography processes include nanoimprint lithography, optical lithography (e.g., water-based optical lithography), plasma etching, and laser machining. In some embodiments, the patterned conductive structures can be formed on a silk matrix via various printing processes. Exemplary printing processes include microfluidic printing, inkjet printing, laser printing, and thermal printing.

In any of these embodiments, the process for forming patterned conductive structures can be adapted to create structures that response to electromagnetic radiation at different wavelengths, e.g., microwave radiation, visible radiation. For example, standard UV photolithography can be used to make micro-stencils for patterned conductive structures. By switching to electron-beam writing, which can fabricate smaller features down to tens of nanometers, patterns on the micro-stencils can be scaled to create nanostencils.

Any of the fabrication processes of the patterned conductive structures described herein can be conducted in a dry, chemical-free environment. Such an environment can reduce the likelihood of possible contamination that might be involved in other photolithography-based conductive material patterning methods, such as lift-off processes and wet-etching. Such methods help in maintaining the integrity and biocompatibility of the silk matrices without adversely affecting the matrices, thereby readily producing applications implantable into a human body, by way of example.

In some embodiments, the conductive material can be a conductive metal, such as gold or copper. Other exemplary metals include, but are not limited to, copper, gold, silver, platinum, chromium, cobalt, aluminum, nickel, rhodium, titanium, magnesium, iron, zirconium, molybdenum, palladium, hafnium, iridium, tungsten, tantalum, and combinations thereof. In some embodiments, the conductive material can be a non-metal. Exemplary non-metals include indium tin oxide (ITO), polysilicon, graphite, and combinations thereof.

In some embodiments, heat-based or reaction-based chemistries can be used to remove portions of the patterned conductive structures. In some embodiments, a process can selectively dissolve an area of a structure.

In some embodiments, the silk matrix with patterned conductive structures do not include adhesive layers, elastomeric layers (e.g., PDMS layers), barrier layers, and/or encapsulation layers over the patterned conductive structures.

Applications

In some embodiments, a silk matrix with a patterned conductive structure can be used as a biological and/or chemical analyte sensor. A biological and/or chemical analyte can interact with a dopant in the silk matrix. The resonance frequency or resonance strength and/or amplitude of the changed electromagnetic signature can indicate the presence of the analyte.

In some embodiments, a silk matrix with a patterned conductive structure can be used for biomimicry. For example, resonators can be selected whose electromagnetic responses collectively match the response for a chemical and/or biological molecule, such as biotin. When the resonators are fabricated on a silk matrix, the resonators' electromagnetic responses can be superimposed to recreate the response of the chemical or biological molecule.

In some embodiments, a silk matrix with a patterned conductive structure can be used for wireless powering units. The patterned conductive structures can be conductive coils. The wireless powering unit can be implantable in a human body. The patterned conductive structures can transduce energy received from outside the human body to power a device within or proximate to the body.

In some embodiments, a silk matrix with a patterned conductive structure can be used for sensing physiological parameters of a human body. Resonators and/or antennae can sample and/or probe bodily fluids for analysis. The analysis can generate information about blood oxygenation or pulsatile response, by way of example, thereby enabling diagnosis. In some embodiments, resonators and/or antennae can indicate the pulse rate of the human body.

In some embodiments, a silk matrix with a patterned conductive structure can be used for determining a state of hydration. In some embodiments, a shift in the resonance frequency of the conductive material structure can correspond to the removal of residual water from a dried silk matrix.

For example, the shift can indicate that the total water content of the silk matrix is less than 10%.

In some embodiments, a silk matrix with a patterned conductive structure can be used for security in pharmaceuticals. The silk matrix can be used as a coating on pharmaceutical doses (e.g., tablets, pills), and can be consumable with the dose. The patterned conductive structure can form a hologram and/or kinegram on the silk matrix, by way of example. The patterned conductive structure can be used for branding, certification, security, tracking, or any combination thereof.

In some embodiments, a silk matrix with a patterned conductive structure can be used for tracking. For example, a patterned conductive structure can be an antenna with an RFID electromagnetic signature. Silk matrices with antennae can be attached to any object, such as packaging, food, pills, inventory, etc. The antennae can operate at various frequencies, such as MHz, GHz, or THz. The antennae can be scanned and information contained on the antennae can be entered into a database. Thus, the locations of objects associated with scanned antennae can be recorded.

In some embodiments, silk matrixes with an RFID device can be attached to a person. The silk matrix can adhere to the person by applying water to the matrix, then applying the matrix to the person's skin. The matrix conforms to the person's skin, thereby attaching to the skin. In some embodiments, the matrix can be attached to children to track the location of children in crowded spaces. In some embodiments, the matrix can serve as a form of identification. After information on the antennae is scanned, an administrator can determine whether the person should be allowed entry into, e.g., an event or a building.

In some embodiments, a silk matrix with an antenna can be attached to documents, such as legal documents. Application of a substance (e.g., ink) to the antenna as a person signs the document can change the electromagnetic signature of the antenna. The electromagnetic signature of the antenna with the applied ink can provide a form of certification for the document.

In some embodiments, a silk matrix with a patterned conductive structure can be used as a sensor. The silk matrix and structure can be designed such that their interactions with a predetermined chemical cause the patterned conductive structure to exhibit a predetermined electromagnetic signature. For example, as food spoils, dopants in the silk matrix can interact with the ethylene released from the shift to shift the electromagnetic signature of the patterned conductive structure to a predetermined frequency. In another example, dopants in the silk matrix can interact with bacteria (e.g., e-coli, *salmonella, listeria, shigella*) to shift the electromagnetic signature of the patterned conductive structure. Users can detect this shift to determine the food has spoiled or been contaminated.

A silk matrix with a patterned conductive structure can be designed to detect glucose. A user can place a drop of blood on the patterned conductive structure, and the level of glucose in the blood can change the electromagnetic signature of the structure. A device can scan and interpret the electromagnetic signature to determine the level of glucose in the user's blood.

In some embodiments, a silk matrix with a patterned conductive structure can be used for remote sensing. The silk matrix and/or patterned conductive structure can change its color or reflectivity in response to an environmental factor. For example, signs with the silk matrix can be placed near natural gas repositories. If the repository begins to leak natural gas, the gas can interact with the silk matrix and patterned conductive structures. In response, the matrix and structures can change color and/or reflectivity to indicate that a gas leak is present at the site.

In some embodiments, a silk matrix with a patterned conductive structure can be used for bio-sensors, bio-detectors, and/or implantable bio-tracking devices. Implantable devices can have conformal surfaces that affix to curvilinear surfaces of internal or external organs.

In some embodiments, a silk matrix with a patterned conductive structure can be used for optical devices. Exemplary optical devices and/or applications for optical devices include lenses, mirrors, laser writing, data encoding, and fiber optics. In some embodiments, a silk matrix with a patterned conductive structure can be used as photonic lattices, colorimetric sensors, or label-free contrast agent. In some embodiments, a silk matrix with a patterned conductive structure can be used as gold electrodes, thin film transistors, or bio-dielectrics.

The patterned conductive structures on the silk matrix can be used in devices such as labels and identifiers, surveillance devices, invisible cloaks, electromagnetic cloaking devices, electromagnetic concentrators, or electromagnetic antennas. The patterned conductive structures on the silk matrix can be used in implantable bioelectric and/or biophotonic devices in the areas of in vivo bio-tracking, bio-mimicry, silk electronics, silk photonics, and implantable biosensor and bio-detectors.

In some embodiments, the patterned conductive structures can be electrodes for measuring neural activity in-vivo. For example, an array of electrodes can be deposited on a silk matrix. The silk matrix and electrodes can be applied to a human brain that will be subject to surgical procedures. The silk matrix can be dissolved away, leaving the electrodes on the brain to monitor the brain's functions during surgery.

The patterned conductive structures resonant at terahertz frequencies can be used for identification and bio-sensing, as numerous chemical and biological agents show unique "fingerprints" at the THz range.

While various embodiments of the methods and systems have been described, these embodiments are exemplary and in no way limit the scope of the described methods or systems. Those having skill in the relevant art may effect changes to form and details of the described methods and systems without departing from the broadest scope of the described methods and systems. Thus, the scope of the methods and systems described herein should not be limited by any of the exemplary embodiments and should be defined in accordance with the accompanying claims and their equivalents.

EXAMPLES

Example 1

Preparation of Silk Films

Figure 14:
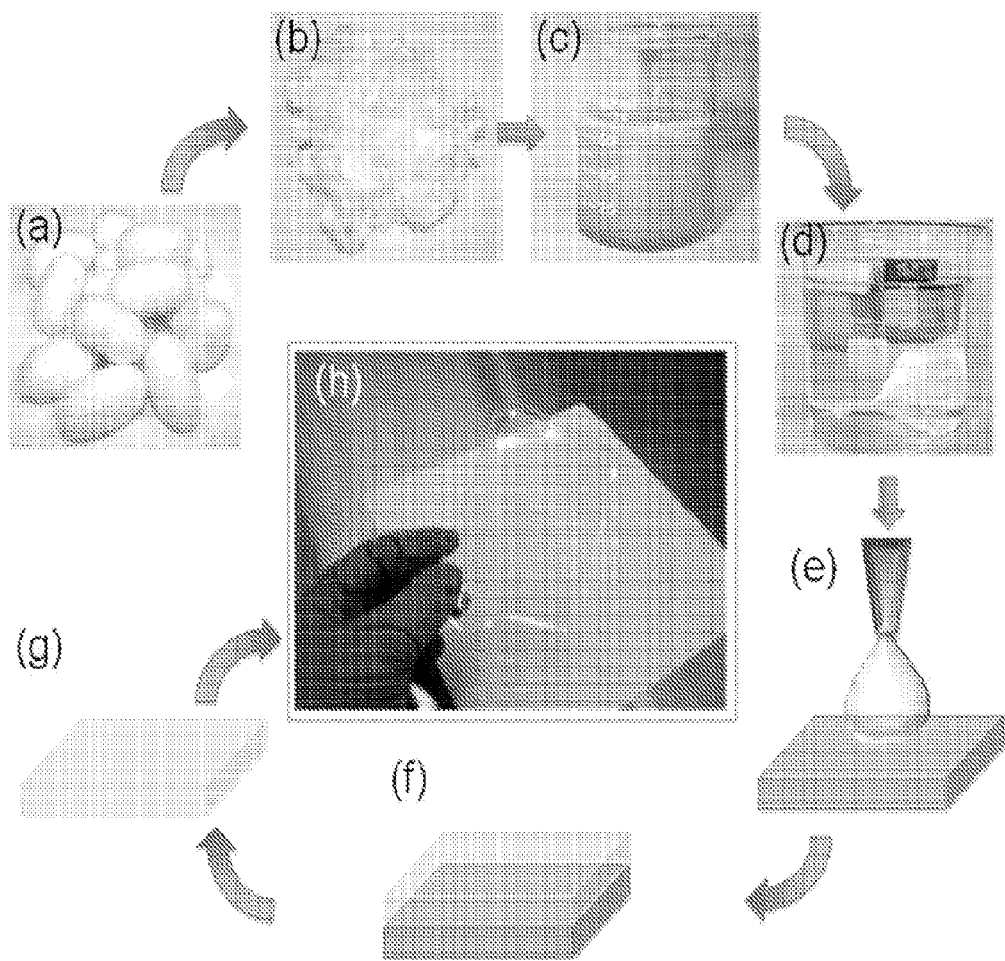
FIG. 14 is a scheme illustrating a process for the preparation of a silk film. Silk cocoons were cut and cleaned (a), boiled with sodium carbonate to extract the water soluble sericin (b), dissolved in lithium bromide (c), dialyzed against water to remove the lithium bromide (d), and then filtered forming a clear water-based silk solution. The silk solution (either undoped or doped with desired biodopants, such as enzymes or proteins) was cast on a PDMS mold (e), cured overnight (f), and then detached after transition to the solid phase (g), yielding an optical transparent biocompatible silk film (h).

A typical preparation process of the silk films is shown in FIG. 14. *Bombyx mori* cocoons were processed in to soluble silk fibroin solution and then cast on polydimethylsiloxane (PDMS) molds.

Silk fibroin solution was obtained as previously described. See Perry et al., Adv. Mater., 20: 3070-72 (2008); Sofia et al., J. Biomed. Mats. Res. 54: 139 (2001). Briefly, *Bombyx mori* cocoons were cleaned and cut into small pieces (FIG. 14a). In a subsequent degumming process, sericin, a water-soluble glycoprotein bound to raw silk fibroin filaments, was removed from the silk strands by boiling *Bombyx mori* cocoons in a 0.02 M aqueous solution of $NaCO_3$ for 60 minutes (FIG. 14b). The resulting silk fibroin was dried and then dissolved in a 9.3 M aqueous solution of LiBr at 60° C. for 4 hours (FIG. 14c). The LiBr salt was removed from the silk fibroin solution over the course of several days, through a water-based dialysis process using Slide-A-Lyzer® 3.5K MWCO dialysis cassettes (Pierce, Rockford, Ill.) (FIG. 14d). The resulting solution was then centrifuged and filtered via syringe based microfiltration (5 μm pore size, Millipore Inc., Bedford, Mass.) to remove any remaining particulates. This process can yield 6%-10% (w/v) silk fibroin solution with minimal contaminants and reduced scattering for optical applications. The silk fibroin solution may be diluted to a lower concentration.

The silk fibroin solution may also be concentrated, for example, to about 30% (w/v). See, e.g., WO 2005/012606. Briefly, the silk fibroin solution with a lower concentration may be dialyzed against a hygroscopic polymer, such as PEG, amylose or sericin, for a time period sufficient to result in a desired concentration.

After preparation of the silk fibroin solution, 15 mL of the solution was cast on a flat PDMS mold (3 inch×5 inch) (FIG. 14e) and allowed to crystallize in air overnight (FIG. 14f). The resulting film was easily removed from the PDMS (FIG. 14g and FIG. 14h) and was approximately 80 μm thick. See Lawrence et al., Biomacromolecules, 9: 1214-20 (2008). Adjusting the concentration and/or the volume of the silk fibroin solution cast on the substrate and curing parameters can result in silk films from 2 nm to 1 mm thick. Alternatively, the silk fibroin solution can be spin-coated on a substrate using various concentrations and spin speeds to produce films from 2 nm to 100 μm. The resulting silk fibroin films were observed to have excellent surface quality and optical transparency.

Example 2

Silk Metamaterial Compositions

One aspect of the invention relates to a silk metamaterial composite having resonant sub-wavelength magnetic properties that comprises one or more layers of metamaterial structure and a silk substrate that carries the one or more layers of metamaterial structure on the substrate.

Other novel devices applications of the silk metamaterial composite are envisioned and are embraced by the present invention. For example, the silk metamaterial composite can be fabricated into sensors and detectors, labels and identifiers, surveillance devices, electromagnetic cloaking devices, electromagnetic antenna devices, and the like.

Some embodiments of the invention provide a silk metamaterial composite for modulating an electromagnetic radiation, comprising a resonant electromagnetic structure comprising an array of metamaterial elements and a silk matrix, where the resonant electromagnetic structure of the silk metamaterial composite is constructed to modulate the electromagnetic radiation. The metamaterial elements may be disposed on or embedded in the silk matrix. At least some of the metamaterial elements are smaller than the wavelength of the electromagnetic radiation for inducing subwavelength resonant electromagnetic response.

Metamaterials are artificially structured materials engineered to provide properties which may not be readily available in nature. The views of electromagnetic material interactions have been dramatically expanded by the development of metamaterials. See Shelby et al., Science, 292: 77-79 (2001); Smith et al., Phys. Rev. Lett., 84: 4184-87 (2000). Metamaterials are resonant sub-wavelength electromagnetic composites typically consisting of highly conductive materials, for instance, highly conductive metals such as gold or copper. The electromagnetic response of metamaterials typically originates from oscillating electrons in highly conducting materials, allowing for means to design a specific resonant response of the electrical permittivity ($\in$) or magnetic permeability (μ). This design flexibility allows for construction of materials with a user-designed electromagnetic response (often unavailable with naturally occurring materials) at a precisely controlled target frequency (See Bingham et al., Opt. Express, 16: 18565 (2008)), which may lead to novel electromagnetic responses or phenomena, such as negative refractive index, perfect lenses, perfect absorbers, and invisible cloaks. See Smith et al., Phys. Rev. Lett., 84: 4184-87 (2000); Pendry et al., Science, 312: 1780 (2006); Schurig et al., Science, 314: 977 (2006).

The term "metamaterial structure" may include any one to three dimensional structural arrangements of metamaterial elements, which exhibit subwavelength characteristics to the desired electromagnetic regime. Metamaterial structure herein includes a resonant electromagnetic structure, and may or may not include the substrate where the metamaterial elements are deposed on or embedded in, depending on various factors, for instance, whether the substrate interferes with the structure of metamaterial elements or whether the substrate contains other dopants (or active agent) interfering with the structure of metamaterial elements or modulations of electromagnetic properties of metamaterials. The structural features of metamaterials should be at least as small as the wavelength of the electromagnetic radiation they interact with in order to affect electromagnetic waves. For example, for visible light typically having wavelengths of less than one micrometer (e.g., 560 nanometers for sunlight), the sizes of metamaterial elements are generally less than the wavelength, e.g., half or less than half of the wavelength; for microwave radiation, such structure features would be on the order of one decimeter.

Metamaterials elements typically are made from highly conductive materials, for instance, conductive metals, such as gold or copper. The electromagnetic response of the metamaterials typically originates from oscillating electrons in the conductive materials, which allows for a designed specific resonant response. Any conductive metal that can be sputtered or evaporated, and deposited on a substrate can be used herein to fabricate metamaterial elements. Exemplary suitable metals include, but are not limited to, copper, gold, silver, platinum, chromium, cobalt, aluminum, nickel, rhodium, titanium, magnesium, iron, zirconium, molybdenum, palladium, hafnium, iridium, tungsten, tantalum, and combinations thereof.

Figure 15:
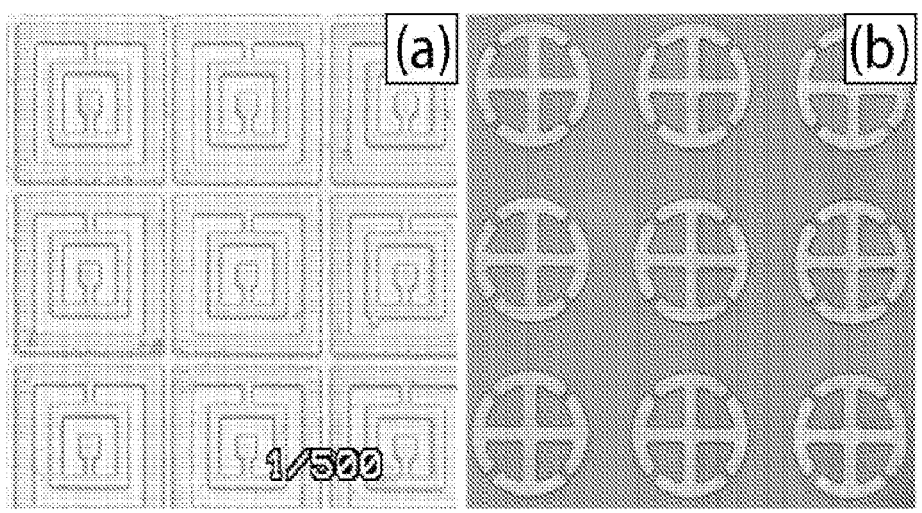
FIG. 15 shows images of exemplary magnetic (a) and electric (b) metamaterial structures having a planar array of (a) split ring resonator "particles" and (b) purely electric resonators, respectively. These devices (unit cell 50 μm×50 μm) exhibit a magnetically (a) and electrically (b) resonant response at far-infrared frequencies.

Metamaterial elements may include any metamaterial elements known to the skilled in the art that can be designed to present structures with a user-designed electromagnetic response, including but not limited to, sources, lenses, switches, modulators and detectors. In one embodiment, the metamaterial element is a resonator element including magnetic resonator and electric resonator, for instance, split-ring resonator, polarization-sensitive electric resonator, polarization non-sensitive electric resonator, or combinations thereof. For example, FIG. 15 shows exemplary magnetic and electric resonators having a planar periodic array of split-ring resonators and electric resonators. The devices containing these subwavelength resonators (e.g., unit cell of the resonators: 50 μm×50 μm) exhibit a magnetically or electrically resonant response at far-infrared frequencies. Exemplary designs and properties of certain resonators may be found in, e.g., U.S. Patent Application Publication No 2009/0262766, which is incorporated herein by reference in its entirety.

The canonical sub-wavelength metamaterial element is a split-ring resonator (SRR). Initially, SRR was proposed as an "atom" designed to exhibit a strongly resonant magnetic response thereby achieving an effective negative permeability ($\mu$) at certain frequency regime above the resonance frequency. See Pendry et al., IEEE Trans. Microwave Theory Tech., 47: 2075 (1999). It was then further demonstrated that SRRs can also show a resonant response to the electric component of a light field when the electric field is aligned perpendicular to the SRR gap to excite the circulating currents within the resonator, resulting in effective negative permittivity ($\in$). See Schurig et al., Appl. Phys. Lett. 88: 041109 (2006); Chen et al., Nature, 444: 597 (2006). In both cases, the electromagnetic response originates from oscillating electrons in highly conductive metals, such as gold or copper, allowing for a tailored electromagnetic response. The SRR can be thought of as a LC (i.e., a resonant circuit consisting of an inductor, and a capacitor) resonator in a simple representation with a resonance frequency of $\omega_0 \sim \sqrt{1/LC}$, where the inductance results from the current path of the SRR and capacitance is mainly determined by the split gap. See Padilla et al., Mater. Today, 9: 28 (2006). Any change in the capacitance or the inductance will result in a change in the resonant response making metamaterials sensitive to the local environment. Therefore, metamaterials can be integrated into devices for sensing and detecting applications.

The resonance electromagnetic responses of metamaterial structure, which include the amplitude and phase of the transimission, reflection and absorption, and the resonance frequency, depend not only on the geometries and materials properties of the metamaterial structures, but also on the dielectric properties of the substrate for the metamaterial structure. Typically any change in the substrate which may affect its dielectric properties can affect the resonance responses of the metamaterial. This property can be used for integration of metamaterial structure with particular substrates for fabrication of devices for sensing and tracking applications.

Generally any non-conductive materials can be used as the substrate. For example, biopolymers such as silk fibroin, collagen and chitosan, are promising materials for fabrication into bio-integrated devices. According to the present invention, silk fibroin is a particularly appealing biopolymer candidate for forming such devices because of its versatile physical and chemical properties, as well as its capability of accommodating various active agents.

Furthermore, according to the present invention, construction of metamaterials that are not constrained as planar structures is also desirable for various applications, such as implantable bioelectronic and biophotonic devices. As described herein, silk metamaterials can be constructed to include multilayer electromagnetic composites, particularly those composites that are not constrained as planar structures. These non-planar metamaterial composites, particularly multilayer electromagnetic composites, can be fabricated on ultrathin, highly transparent, and highly flexible substrates.

In one embodiment, the silk matrix of a silk metametarial composite is silk film. The silk fibroin film may be prepared by depositing an aqueous silk fibroin-containing solution on a support substrate, such as a PDMS, glass or quartz substrate, and allowing the silk fibroin solution to dry into a film. In this regard, the substrate coated with silk fibroin-based solution may be exposed in air for a period of time, such as several hours. Depositing the silk fibroin solution can be performed by, e.g., using a spin-coating method, where the silk fibroin solution is spin-coated onto the substrate to allow the fabrication of thin membranes of non-uniform in height; or simply by pouring silk fibroin solution over the top of the substrate.

Regarding the preparation of a silk fibroin solution, this may be done in an all-aqueous manner. See, e.g., U.S. Patent Application Publication No. 2005/0260706; WO 2005/012606, which are incorporated herein by reference in their entirety. Optionally, a micro-filtration step may be used herein. For example, the prepared silk fibroin solution may be processed further by centrifugation and syringe based micro-filtration before depositing on the substrate. This process enables the production of 6%-10% w/v silk fibroin solution of excellent quality and stability. The micro-filtration step is often desirable for the generation of high-quality optical films with maximized transparency and, consequently minimized scattering.

Example 3

Exemplary Polymer Components that can be Utilized in Electronic Components as Described Herein In some embodiments of the present invention, one or more biocompatible and/or biodegradable polymers may be blended in silk fibroin solution for further processing into silk matrix. For example, additional biopolymers, such as chitosan, exhibit desirable mechanical properties, can be processed in water, blended with silk fibroin, and form generally clear films for optical applications. Other biopolymers, such as collagen, gelatin, agarose, chitin, polyhydroxyalkanoates, pullan, starch (amylose amylopectin), cellulose, alginate, fibronectin, keratin, hyaluronic acid, pectin, polyaspartic acid, polylysin, pectin, dextrans, and related biopolymers, or a combination thereof, may be utilized in specific applications, and synthetic biodegradable polymers such as polyethylene oxide, polyethylene glycol, polylactic acid, polyglycolic acid, polycaprolactone, polyorthoester, polycaprolactone, polyfumarate, polyanhydrides, and related copolymers may also be selectively used. The polymer selected herein to be blended into the silk matrix should not negatively impact the optical transparency and electromagnetic properties of the silk matrix.

Example 4

Chemical Modifications of Silk Fibroin

In some embodiments, silk fibroin for use in accordance with the present invention can be chemically modified, e.g., with one or more active agents, for example through diazonium or carbodiimide coupling reactions, avidin-biodin interaction, or gene modification and the like, to alter the physical properties and functionalities of the silk protein. See, e.g., PCT/US09/64673; U.S. Application Ser. No. 61/227,254; Ser. No. 61/224,618; Ser. No. 12/192,588, which are incorporated herein by reference in their entirety.

Additional functionalities may be conferred to the silk matrix, for example, through enzymatically polymerization, a conducting polymer can be generated between silk film and the substrate supporting the film, making an electroactive silk matrix, and providing potentials of electro-optical devices. See, e.g., WO 2008/140562, which is incorporated herein by reference in its entirety.

Example 5

Fabrication of Silk Metamaterial Composites

FIG. 7 depicts the fabrication process of silk metamaterials prepared by spraying the metamaterial elements on free-standing silk films.

The micro stencils with the desired patterns which represent the metamaterial structure were fabricated on a commercially purchased 4" silicon wafer. A 400 nm-thick super low-stress silicon nitride (SiNx) film was pre-deposited on both sides of the silicon wafer by low-pressure chemical vapor deposition (LPCVD). The patterns of resonator elements (e.g., SRRs) were fabricated using standard UV photolithography followed by reactive ion etching (RIE) using Sulfur hexafluoride ($SF_6$) and Helium (He) at 110 w for 6 minutes, with the MICROPOSIT® S1813 PHOTO RESISTS (Shipley, Marlborouge, Mass.) placed on the top side of the silicon wafer as the etching mask to define the stencil patterns. The silicon wafer was then flipped over. Open windows for performing backside wet-etching were patterned on backside of the wafer using a similar process as described above. This process was followed by backside wet-etching through rinsing the wafer in a stirred 25% concentrated KOH solution at 70° C. for a few hours. The suspended stencil structures were released when KOH etched through the wafer from the backside and reached the SiNx film on the top side. The stencils can be as large as a few $cm^2$ or even larger without an upper limit, depending on the quality of the pre-deposited SiNx film.

FIG. 8A and FIG. 8C show an exemplary as-fabricated micro stencil. A 7×7 stencil array was patterned on the 4" silicon wafer. The area of each stencil was approximately 1 cm×1 cm with a total area of SRR array being approximately 8 mm×8 mm in the center of the stencil. A 1 mm wide silicon frame was kept on the edges of the stencils as the supporting structure for later handling.

The micro stencils were carefully attached to the 80 µm thick silk films in contact mode. The micro stencils were aligned to the silk films under microscopy and the edges of the micro stencils were attached tightly to the silk films with scotch tapes. A thin layer of 100 nm thick gold was then "sprayed" on the silk substrates uniformly at a rate of ~3 Å/s using electron-beam evaporation. The evaporation process was controlled under 40° C., which is a safe temperature for maintaining the silk quality. After the spraying the metal layers, the micro stencils were removed by peeling off the tape and releasing the as-sprayed silk films, resulting silk metamaterial composites. The as-fabricated silk metamaterial composite comprising metamaterial structures on the free-standing silk films showed good uniformity, mechanical robustness and flexibility. The resulting silk metamaterial composite can be wrapped into a capsule-like cylinder with a diameter of ~3 mm with no distortion or cracking observed, as shown in FIG. 8E.

Example 6

Characterization of Silk Metamaterial Composites

Terahertz time-domain spectroscopy (THz-TDS) was used to characterize the electromagnetic response of the silk metamaterial composites. The measurements were performed at room temperature in a dry (<0.1% humidity) air atmosphere. The transmission of the THz electric field was measured for a sample and a reference respectively, with the reference being air in this example. The amplitude and phase of the electric field spectral were calculated through Fourier transformation of the time-domain pulses. The spectral transmission was then obtained by dividing the transmission of the sample by the transmission of the reference, as illustrated in the inset of FIG. 5.

THz-TDS measurement was carried out on a series of 80 µm thick pure silk films, which showed high field transmission of ~60% of terahertz radiation in the range from 0.15 THz to 1.5 THz, as shown in FIG. 5. The refractive index of the pure silk films was then experimentally determined, using standard approach described in previous publications, to be n=1.91+i0.12 from 0.15 THz to 1.5 THz. See Duvillaret et al., IEEE J. Sel. Top. Quantum Electron, 2: 739 (1996); Pupeza et al., Opt. Express, 24: 4335 (2007).

Silk metamaterial composites presenting numerous metamaterial structures were fabricated and characterized with THz-TDS measurements, including the canonical split ring resonators (single SRR: Sample No. 1) and purely electric resonators (e.g., polarization non-sensitive electric resonator: Sample No. 2, and polarization sensitive electric resonator: Sample No. 3). Sample No. 1 has a unit cell size of 50 µm×50 µm; and Samples No. 2 and Sample No. 3 have a unit cell of 100 µm×100 µm. The samples were diced into 1 cm×1 cm squares and mounted at normal incidence to the THz beam with the electric field perpendicular to the SRR gap.

The experimental and simulation results are shown in FIG. 6. The black solid lines show the experimentally measured field transmission as a function of frequency. The red dash lines are the results of electromagnetic simulations using CST MICROWAVE STUDIO™ 2008 (CST Computer Simulation Technology AG, Darmstadt, Germany). In the electromagnetic simulations, the dimensions shown in FIG. 6 were used for the resonator elements and the experimentally measured refractive index for silk substrates (n=1.91+i0.12) was used. As shown in FIG. 6, the experimental results are in reasonable agreement with the simulation data, although noticeable off-resonance disagreement occurs consistently in all three samples, which may arise partly from the fabrication imperfections and the surface roughness of the samples. As expected from simulation results, Sample No. 1, having a smaller unit cell than Sample No. 2 and Sample No. 3, presents a higher resonance frequency (0.85 THz) than those of Sample No. 2 (0.7 THz) and Sample No. 3 (0.4 THz). All of these samples display strong resonances comparable to those measured on semiconducting and polymer substrates. See Padilla et al., Phys. Rev. B, 75: 041102R (2007); Tao et al., J. Phys. D: Appl. Phys., 41: 232004 (2008). The resonance responses from these samples are associated with the LC resonant response that arises from circulating currents driven by the electric field that is aligned perpendicular to the SRR gap, i.e., the resonant changes in the transmission of terahertz radiation of these samples correspond to an effective permittivity.

Example 7

Fabrication of Silk Films Via Electrogelation ("e-Gel")

Current methods to produce silk films include casting and spin coating. We introduce a new method for the fabrication of silk films: electrogelation. By using a closed-loop anode, the controlled application of electrical current to regenerated silk fibroin (RSF) solution yields a silk gel which, upon drying, forms an optically transparent film. This technique allows for the rapid production of freestanding mechanically robust thin films with desirable characteristics that include exceptionally low surface roughness, curved geometries, and thicknesses into the nanoscale.

Recently it has been established that RSF solution, derived from *Bombyx mori* silkworms, responds to direct current (DC) electrical stimulation by aggregating around the anode and forming a gel, called an e-gel to specify the method of its formation.[1-3] A common thread in preceding works is the use of simple electrodes that are rod-like in their geometry. In this paper, we expound upon this 1-D approach to show that configuration of the positive electrode into a closed loop leads to the formation of silk films that are circumscribed by the loop itself. Moreover, in contrast to other electrodeposition studies, both with silk and other biopolymers, the resulting e-gel films possess no underlying surface, supported only at the films' edges.[1-10] In the simplest case, the loop lies within a 2-D plane, and a flat circular film is produced. In addition, through manipulation of the loop, a number of 3-D topologies can be realized.

The mechanism of e-gel assembly is primarily driven by a localized decrease in solution pH, a byproduct of the electrolysis of water.[2,3] The electrical current required is small, less than 1 mA. While a current is applied, the local pH in the vicinity of the anode decreases, and oxygen gas is released by the following reaction:

  (1)

Conversely, fluid in the vicinity of the cathode experiences an increase in pH and hydrogen bubbles are released as follows:

  (2)

Figure 16:
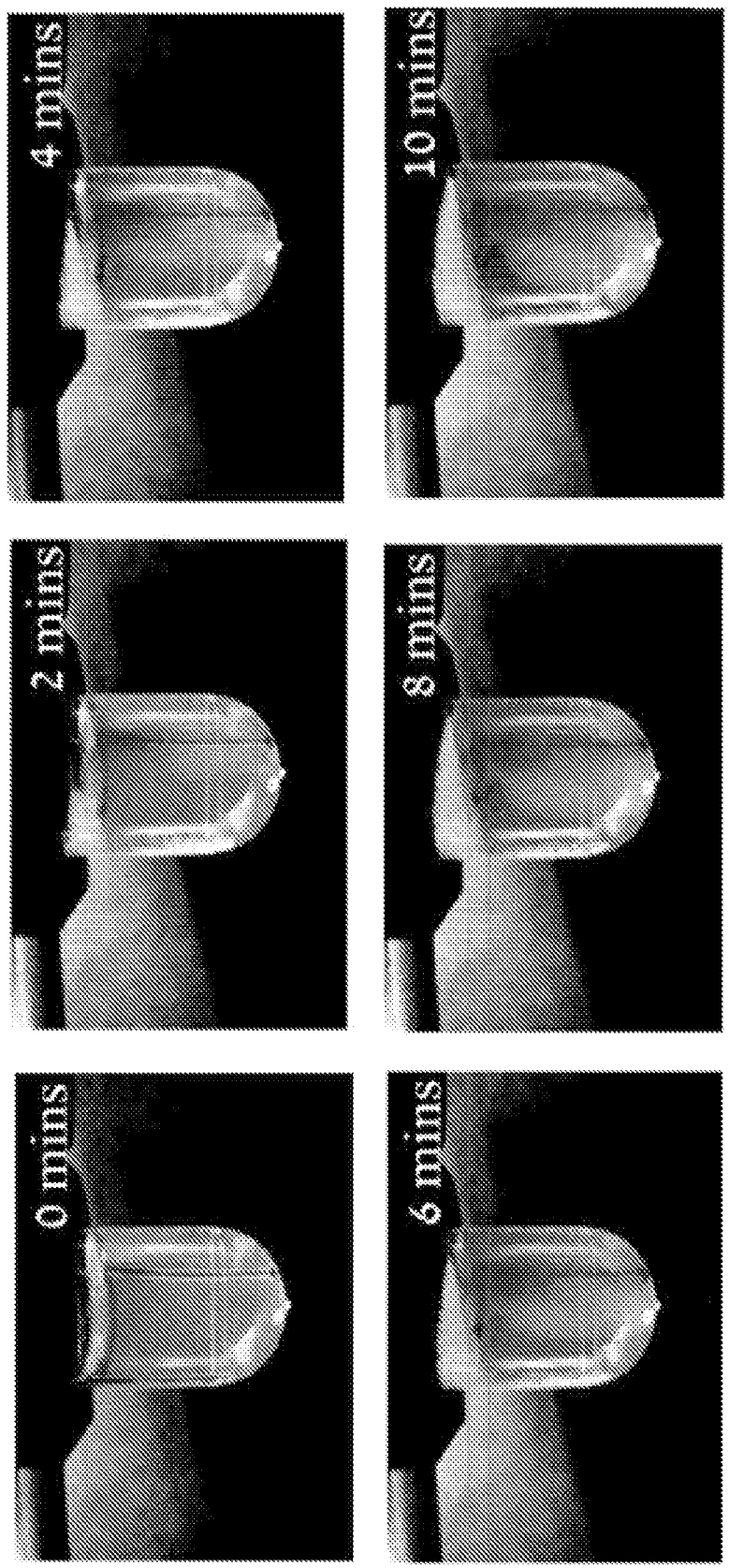
FIG. 16 provides images of silk e-gel formation which parallels pH gradient evolution. Using a DC power supply, 10V (constant voltage) were applied to a silk solution (initial pH: 6.5) containing methyl red indicator dye. With increasing time, fluid around the anode (right electrode) experiences a significant decrease in pH and a growing aggregate of e-gel mass is apparent.

FIG. 16 depicts the evolution of pH gradients within an RSF sample as shown through the use of methyl red, an indicator dye that is colorless for 4.4<pH<6.2. A solution more acidic than pH 4.4 appears red, while one that is more basic than pH 6.2 appears yellow. Using short-range pH paper, the initial pH of silk solution was measured as 6.5. With increasing time, acidification of the local environment around the anode is evident and expanding.

Figure 17:
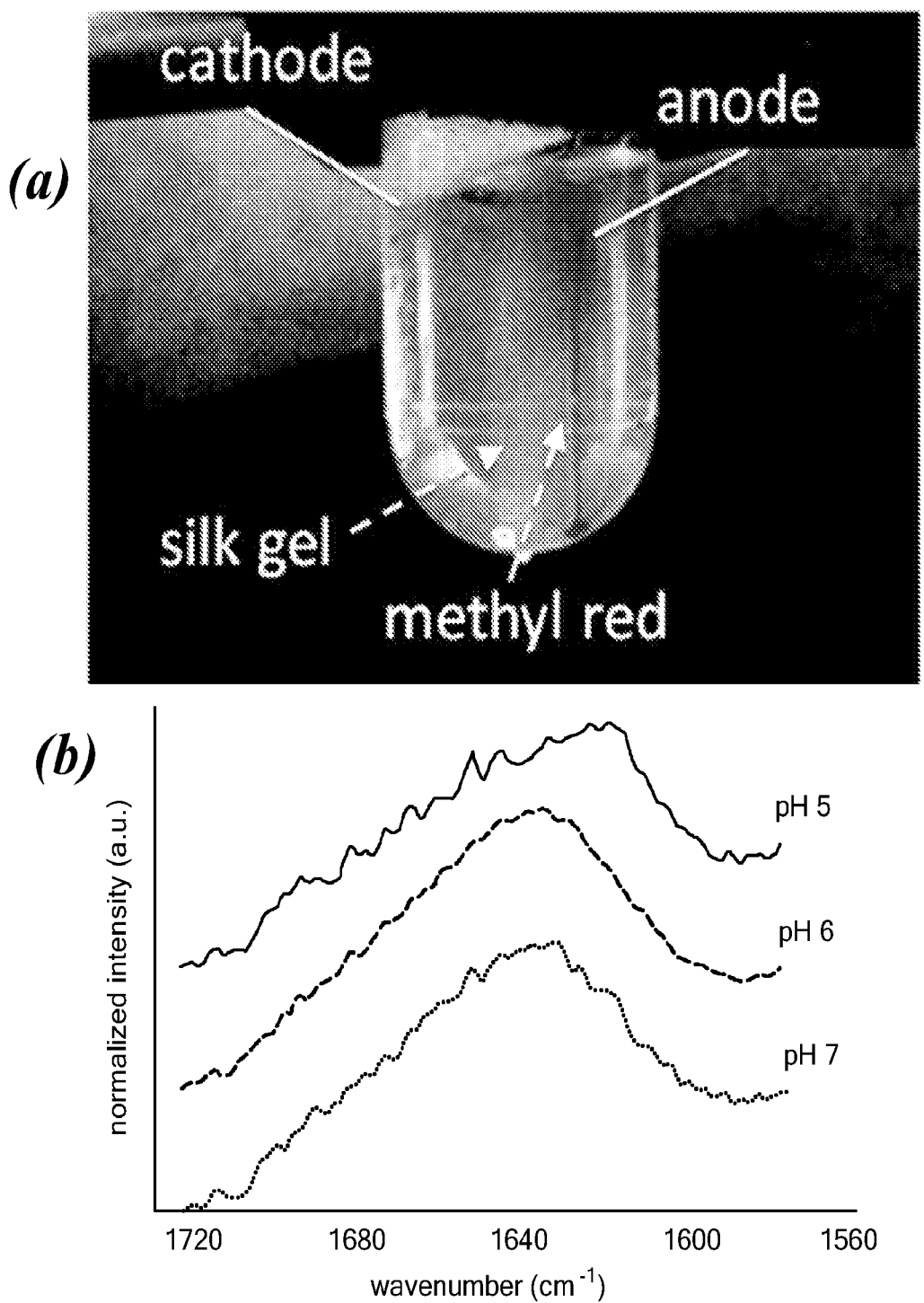
FIG. 17. (a) The silk gel, visible in white, leads the methyl red front, corresponding to thresholds for these events, pH 5.0 and 4.4, respectively. (b) Increasing acidity produces conformational changes within the protein, as shown by FTIR. This is particularly evident within the 1616-1637 $cm^{-1}$ region, representing enhanced beta-sheet content.

Local changes in pH induce conformational changes within the silk molecule, as shown in FIG. 17*b*.[11-13] A number of papers examining the gelation of silk solution have shown that a pH of approximately 5 serves as a critical threshold, below which silk solution will gel rapidly.[2,14,15] This also is consistent with studies of silkworm physiology which have found that the transition of silkworm silk solution dope in the gland to a spinnable gel occurs at pH 4.8.[16,17]

The role of electric charge in the process is significant as well. Silk molecules are negatively charged, and throughout the literature, experimental measurements of the isoelectric point (pI) of silk fibroin fall between 3.6-4.2, well below the initial pH of RSF solution.[18-21] Electrical stimuli thus promote the migration of silk molecules towards the positive electrode, a behavior validated by measured increases in silk concentration within the e-gel mass, relative to the surrounding solution. Independently-evolving pH gradients coincide with this behavior, as the anodic environment gradually approaches the threshold for silk gel formation.

Use of a ring-shaped anode forces the initial gel growth to form as a sheet that is confined to the plane of the electrode and circumscribed by the ring itself. Only after that space is occupied will silk gel develop above and below the initial plane and around the wire. This result is entirely different than what is observed in an incomplete loop, such as one interrupted by a cut, where gel formation envelops the wire uniformly both in and outside of the loop and no film is produced. The difference between these two events reflects the uniqueness of the closed loop result and suggests the role that electric field distribution may play in the e-gel film process, promoting an almost exclusive aggregation of silk mass within the plane of the ring.

Figure 18:
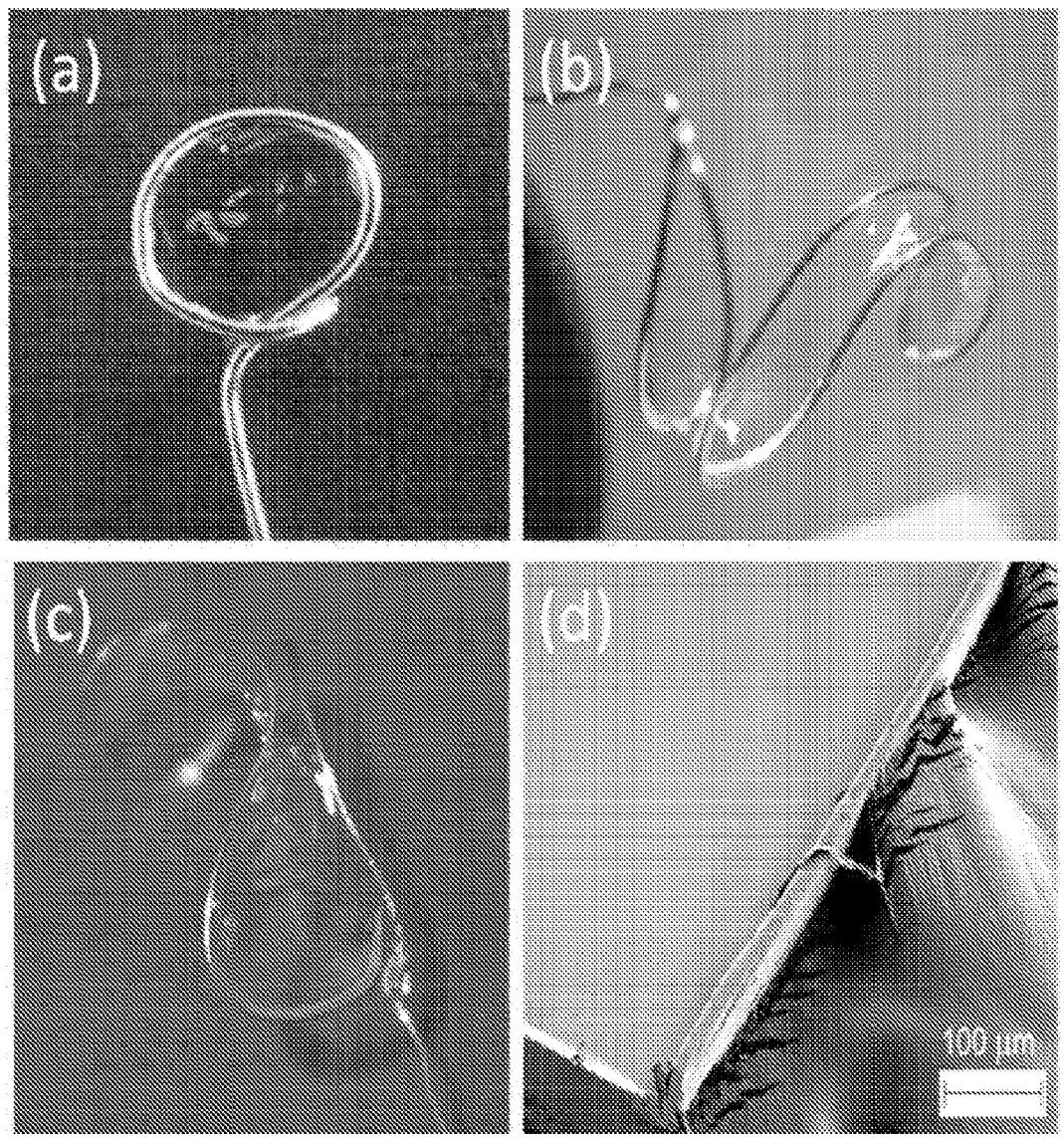
FIG. 18. A selection of anode geometries reflect the ability of this process to create silk films with varying non-planar topologies including: (a) a ring (b) 'S' and (c) saddle point. (d) An SEM image of an e-gel film segment illustrates gross smoothness of the e-gel film face across a larger area. The edge roughness is due to manual cutting with a razor blade.

Folding the ring allows for e-gel films with unique geometries as shown in FIG. 18, enabling silk films with topologies that can not be realized otherwise through existing silk film fabrication methods. The applications for this approach include biosensors and drug delivery devices with unusual geometries that can be molded to fit conformally upon target organs, as well as customized patient-specific tissue engineered scaffolds for curved but stratified tissue architectures. These ideas serve to complement a recent paper that introduced initially flat silk films that conformed to the brain through wetting. However, acceptable conformation to the underlying tissue geometry was only apparent for films less than 7 microns thick.[22]

Figure 19A:
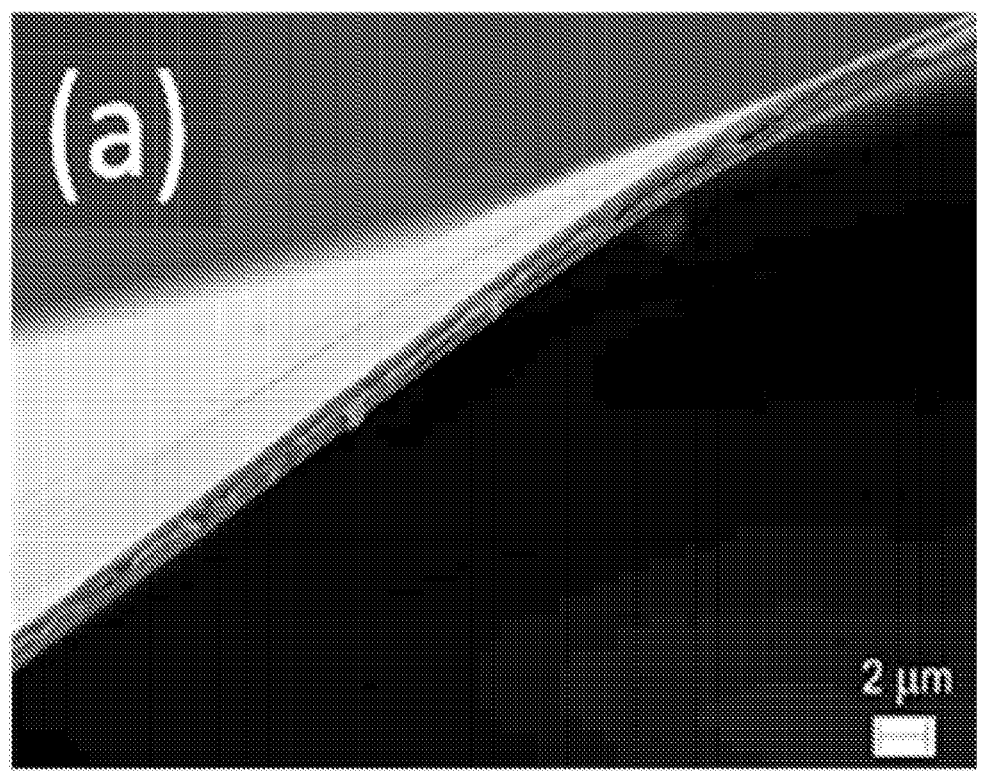
FIG. 19. E-gel films can be extremely thin and confer very low surface roughness. This latter quality makes them suitable for optical transmission. (a) An SEM image depicts a film whose thickness is on the order of 1 μm. (b) An AFM image, with a sample area 10 μm by 10 μm, shows minimal surface roughness. RMS values of 4-6 Å were seen along sample paths 1.5-2.5 μm in length, drawn orthogonal to the visible variations from adjacent horizontal line scans. (c) Silk e-gel film transparency is shown using a sample approximately 25 μm thick. (d) The corresponding optical transmission spectrum agrees with the preceding physical example.
Figure 19B:
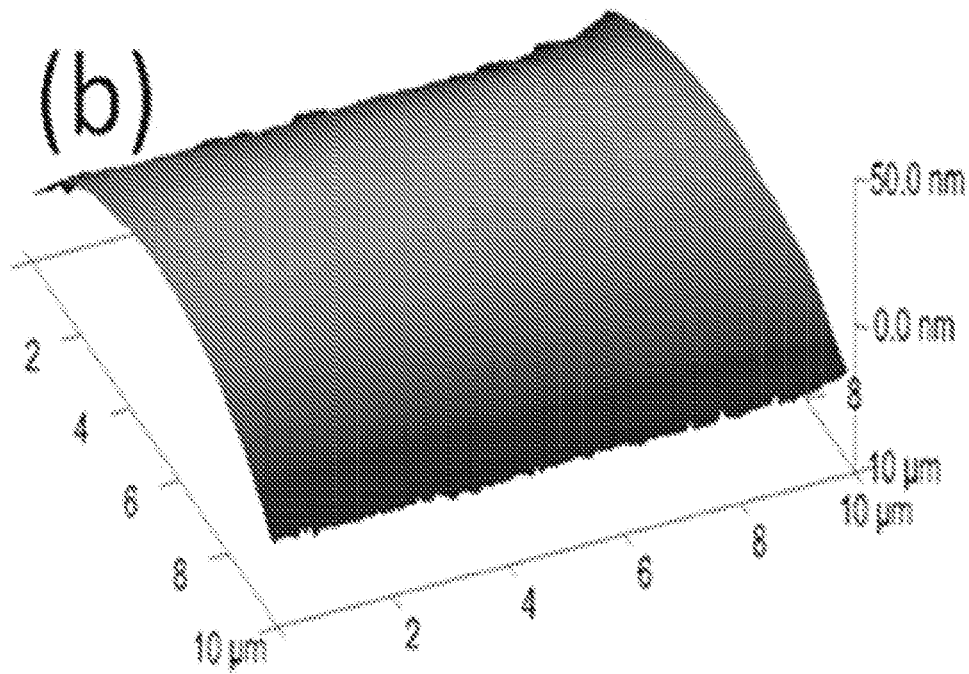
Figure 19C:
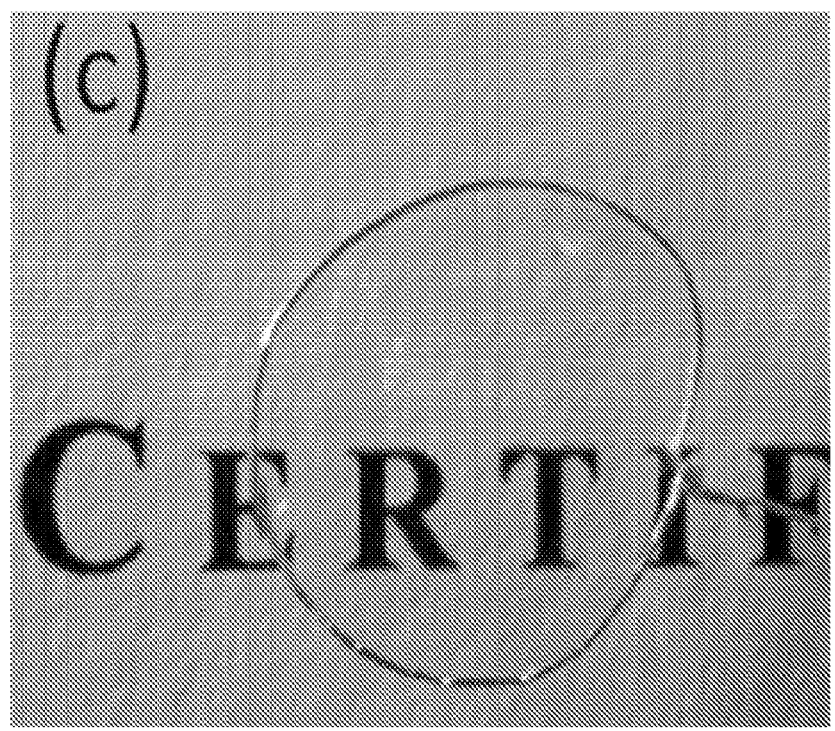
Figure 19D:
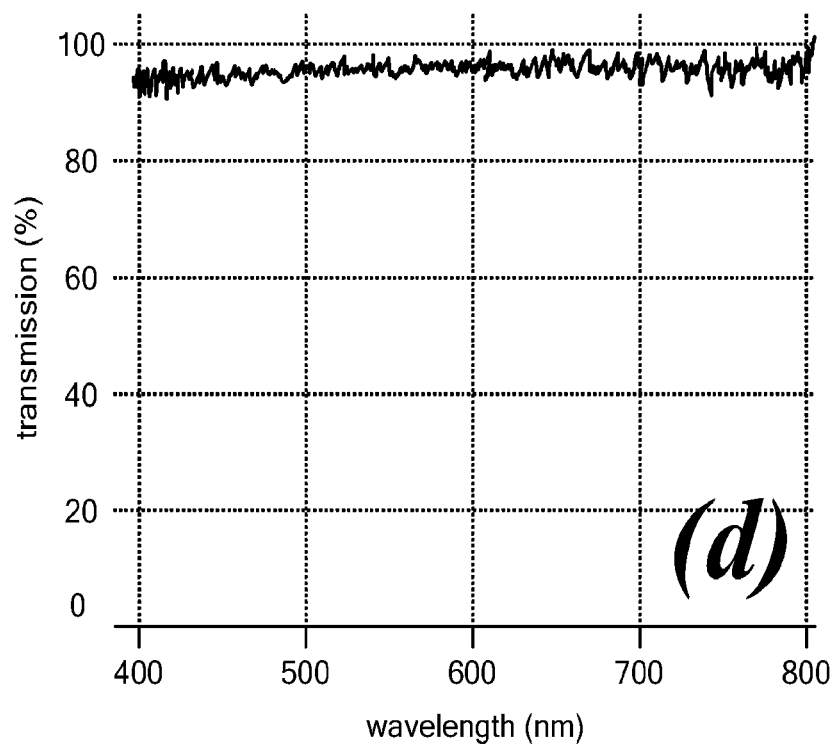

E-gel films allow for the production of curved films across a range of thicknesses. FIG. 19*b* shows cross-sectional scanning electron microscope (SEM) images of films ranging from those tens of microns thick to thin films with submicron thickness. Film thickness can be controlled by numerous factors including wire gauge, voltage, silk concentration and exposure time. Thin films are of particular interest as they lend to applications in photonics and optoelectronics.[23,24] Further, by comparison with other silk film fabrication methods, the electroglelation process allows for more facile fabrication and yields thin films that are easier to manipulate.[25]

Surfaces of e-gel films are extremely smooth, as shown in FIG. 18. Multiple straight line topographical measurements taken across a 10 μm×10 μm film section with an atomic force microscope (AFM) yielded root-mean-squared (RMS) values between 4-6 Å. On a larger scale, SEM images of a film section with dimensions of the order of a millimeter showed no detectable surface defects. These results are in contrast with results from alternating current (AC) experiments, where the mean roughness was two orders of magnitude higher, suggesting that silk molecules may align themselves in response to the DC field.[26]

Silk films produced via electrogelation are optically transparent, with characteristics similar to those observed in silk films made by other methods. Spectroscopic measurement of optical transmission is in excess of 90% across the visible spectrum for films 20-30 μm thick, as shown in FIG. 19, which compares favorably to previously reported results for cast silk films.[27,28] In addition, refractive index measurements of n=1.54 using a commercial refractometer showed little difference from previously published results employing other silk film fabrication techniques.[28-30]

Previous papers highlight the problematic role that bubble formation plays within the developing e-gel, as the gaseous products of water electroylsis. Electrode geometry is significant. With a rod-shaped anode, oxygen bubbles nucleate upon the electrode's surface and accumulate within the expanding gel, compromising mechanical stiffness and serving as an electrical insulator that retards continued gel formation.[1-3] At the cathode, hydrogen bubble nucleation takes place at a rate double that of anodic oxygen as per the overall electrolysis reaction:

  (3)

Flat ring-shaped anodes avoid significant bubble interference during film formation, an effect that can be explained by geometry: while a film develops within the ring, the silk-metal interface on the outside of the ring does not experience any significant e-gel mass accumulation, allowing bubbles to escape without becoming entrapped within the forming gel. Moreover, the rate of bubble formation can be minimized by regulating electrical current within the solution.[3,31] It is of note, however, that some three-dimensional configurations result in the entrapment of bubbles, though this effect can be minimized through the use of filters that capture or redirect bubbles away from the developing e-gel film.

Previously, electrogelation was noted for its potential to generate biocompatible adhesive silk as well as for its ability to serve as a complementary process to hydrogels and gels formed via sonication. Here, electrogelation with a closed-loop anode is shown to be a rapid, novel approach for generating silk films that are exceptionally smooth. Further, manipulation of the electrode can confer curvature to the resulting films, something unattainable via alternative methods. Fine control of the fabrication process has shown the capability to generate a range of film thicknesses from tens of microns to hundreds of nanometers, creating interesting opportunities in a number of fields spanning photonics and optoelectronics to biosensing, drug delivery and tissue engineering.

Regenerated silk fibroin (RSF) solution was produced through slight modifications to the standard process [1, 15, 32]. Degumming time within a 0.02 M sodium carbonate solution was limited to a 10 minute boil, shorter than in preceding papers discussing the e-gel process, to minimize fibroin protein degradation [1, 2]. Correspondingly, fibroin was solubilized in 9.3M lithium bromide for 16 hours in a 60° C. oven to allow for more complete unfolding of the comparatively longer fibroin chains. The chaotropic salt was subsequently removed through dialysis (3.5 kDa MWCO) against Milli-Q water for a total of 72 hours, yielding an 8% (w/v) silk solution. The resulting liquid was then purified by centrifugation at 8,800 rpm over two 25-minute long periods, with the temperature held constant at 4° C.

To examine the temporospatial evolution of pH gradients within silk solution exposed to DC current, 5 µL of methyl red indicator dye (Riedel-de-Haën) was added to 2 mL of silk solution. Methyl red is an azo dye that appears red below pH 4.4 and yellow above pH 6.2. The initial RSF pH, measured by short-range pH paper (Micro Essential Lab, Hydrion) was 6.5. Gold-plated rods, 0.6 mm in diameter, were used as electrodes at a separation distance of 5 mm Video was recorded for 10 minutes at 10V, constant voltage (Mastech, HY3005D-3 DC).

Ring-shaped electrodes were produced from a selection of gold (0.2 mm diameter) and gold-plated (0.6, 0.8 and 1.0 mm diameter) wires (Alfa Aesar and Paramount Wire Company). To assure reproducibility, each anode was created by hand by twisting the wire around rigid plastic cylinders of known diameter, ranging from 7 to 20 mm. Meanwhile, the cathode remained a straight segment of gold wire. For film fabrication, 2 mL of silk solution were deposited into polystyrene tubes prior to introduction of the ring anode and straight cathode. Current was delivered to the solution through a power supply at 5, 10 or 25V, constant voltage, for durations between 0.5-10 minutes. The positive electrode, circumscribing a silk film, was subsequently removed and allowed to air dry. Changes in silk concentration between the e-gel film and the surrounding solution were measured by comparing the wet and dry masses of samples collected following electrical stimluation.

Films were studied using a host of analytical tools. SEM (Carl Zeiss, Ultra55) images were collected, after sputter coating (Cressington, 208HR) with a Pt/Pd target, using both InLens and secondary backscatter detectors. AFM (Veeco, Nanoscope III) images were recorded in air using Research Nanoscope software version 7.30 (Veeco). A 225 mm long silicon cantilever with a spring constant of 3 N/m was used in tapping mode. FTIR spectra were taken using an ATR probe, with subsequent background subtraction.

Optical transmission was measured in software (Ocean Optics, SpectraSuite) using a tungsten-halogen light source (Ocean Optics, LSD and a visible-range spectrometer (Ocean Optics, USB2000) Refractive index was determined using a commercial refractometer (Metricon, 2010 M prism coupler).

[1] G. G. Leisk, T. J. Lo, T. Yucel, Q. Lu, D. L. Kaplan, *Adv Mater.* 2010, 22, 711.
[2] T. Yucel, N. Kojic, G. G. Leisk, T. J. Lo, D. L. Kaplan, *J. Struct. Biol.* 2010, 170, 406.
[3] D. Maniglio, W. Bonani, G. Bortoluzzi, E. Servoli, A. Motta, C. Migliaresi, *J. Bioact. Compatible Polym.* 2010, 25, 441.
[4] A. R. Boccaccini, S. Keim, R. Ma, Y. Li, I. Zhitomirsky, *Journal of the Royal Society Interface* 2010, 7, S581.
[5] Y. Liu, E. Kim, R. Ghodssi, G. W. Rubloff, J. N. Culver, W. E. Bentley, G. F. Payne, *Biofabrication* 2010, 2, 022002.
[6] X. W. Shi, Y. Liu, A. T. Lewandowski, L. Q. Wu, H. C. Wu, R. Ghodssi, G. W. Rubloff, W. E. Bentley, G. F. Payne, *Macromolecular Bioscience* 2008, 8, 451.
[7] X. W. Shi, X. H. Yang, K. J. Gaskell, Y. Liu, E. Kobatake, W. E. Bentley, G. F. Payne, *Adv Mater.* 2009, 21, 984.
[8] R. Ma, R. F. Epand, I. Zhitomirsky, *Colloids and Surfaces B-Biointerfaces* 2010, 77, 279.
[9] H. M. Yi, L. Q. Wu, W. E. Bentley, R. Ghodssi, G. W. Rubloff, J. N. Culver, G. F. Payne, *Biomacromolecules* 2005, 6, 2881.
[10] M. Cheong, I Zhitomirsky, *Colloids and Surfaces A-Physicochemical and Engineering Aspects* 2008, 328, 73.
[11] X. G. Li, L. Y. Wu, M. R. Huang, H. L. Shao, X. C. Hu, *Biopolymers* 2010, 89, 497.
[12] J. Zhu, Y. Zhang, H. Shao, X. Hu, *Polymer* 2008, 49, 2880.
[13] C. Dicko, F. Vollrath, J. M. Kenney, *Biomacromolecules* 2004, 5, 704.
[14] Z. H. Ayub, M. Arai, K. Hirabayashi, *Bioscience Biotechnology and Biochemistry* 1993, 57, 1910.
[15] U. Kim, J. Park, C. Li, H. Jin, R Valluzzi, D. L. Kaplan, *Biomacromolecules* 2004, 5, 786.
[16] A. E. Terry, D. P. Knight, D. Porter, F. Vollrath, *Biomacromolecules* 2004, 5, 768.
[17] C. W. P. Foo, E. Bini, J. Hensman, D. P. Knight, R. V. Lewis, D. L. Kaplan, *App. Phys A* 2006, 82, 223.
[18] T. Asakura, R. Sugino, J. Yao, H. Takashima, R. Kishore, *Biochemistry* 2002, 41, 4415.
[19] Y. H. Yang, Z. Z. Shao, X. Chen, *Acta Chimica Sinica* 2006, 64, 1730.
[20] A. M. Sookine, M. Harris, *Textile Res* 1939, 9, 374.
[21] S. Nagarkar, T. Nicolai, C. Chassenieux, A. Lele, *Phys. Chem. Chem. Phys.* 2010, 12, 3834.
[22] D. H. Kim, J. Viventi, J. J. Amsden, J. L. Xiao, L. Vigeland, Y. S. Kim, J. A. Blanco, B. E. Panilaitis, E. S. Frechette, D. Contreras, D. L. Kaplan, F. G. Omenetto, Y.

G. Huang, K. C. Hwang, M. R. Zakin, B. Litt, J. A. Rogers, *Nature Mat.* 2010, 9, 511.

[23] R. Popescu, C. Pirvu, M. Moldoveanu, J. G. Grote, F. Kajzar, I. Rau, *Molecular Crystals and Liquid Crystals* 2010, 522, 229.

[24] R. Popescu, M. Moldoveanu, I. Rau, *Key Engineering Materials* 2009, 415, 36.

[25] C. Jiang, X. Wang, R. Gunawidjaja, Y. H. Lin, M. K. Gupta, D. L. Kaplan, R. R. Naik, V. V. Tsukruk, *Adv. Funct. Mater.* 2007, 17, 2229.

[26] E. Servoli, D. Manigliio, A. Motta, C. Migliaresi, *Macromolecular Bioscience* 2008, 8, 827.

[27] F. G. Omenetto, D. L. Kaplan, *Nature Photonics* 2008, 2, 641.

[28] B. D. Lawrence, M. Cronin-Golomb, I. Georgakoudi, D. L. Kaplan, F. G. Omenetto, *Biomacromolecules* 2008, 9, 121.

[29] A. Frey-Wyssling, *Biochimica et Biophysica Acta* 1955, 17, 155.

[30] S. T. Parker, P. Domachuk, J. Amsden, J. Bressner, J. A. Lewis, D. L. Kaplan, and F. G. Omenetto, *Adv Mater.* 2009, 21, 2411.

[31] C. W. M. P. Sillen, E. Barendrecht, L. J. J. Janssen, S. J. D. Van Stralen, *Int. J. Hydrogen Energy.* 1982, 7, 577.

[32] J. J. Amsden, P. Domachuk, A. Gopinath, R. D. White, L. Dal Negro, D. L. Kaplan, F. G. Omenetto, *Adv Mater.* 2010, 22, 1746.

Example 8

Exemplary Silk Films

In some embodiments, the properties of the silk fibroin film, such as thickness and content of other components, as well as optical features, may be altered based on the concentration and/or the volume of the silk fibroin solution that is applied to a substrate. For instance, the thickness of the silk film may be controlled by changing the concentration of the silk fibroin in the solution, or by using desired volumes of silk fibroin solution, resulting silk fibroin film with a thickness ranging from approximately 2 nm to 1 mm. In one embodiment, one can spin-coat the silk fibroin onto a substrate to create films having thickness from about 2 nm to about 100 µm using various concentrations of silk fibroin and spinning speeds. The silk fibroin films formed therefrom have excellent surface quality and optical transparency.

In some embodiments, silk film used herein is a free-standing silk film. The silk film may be ultrathin, for instance, up to 100 µm, up to 75 µm, up to 25 µm, up to 7 µm, up to 2.5 µm, or up to 1 µm. Such ultrathin silk films, depending on the casting technique and curing parameters of silk films, may provide soft and flexible films for fabricating silk metamaterial composite that has non-planar structure.

The mechanical property of silk film can be modified by addictives, such as glycerol, to provide a more ductile and flexible silk fibroin film. See, e.g., PCT/US09/060,135, which is incorporated herein by reference in its entirety. Such modification of silk film can be used in many biomedical applications, such as tissue engineering, medical devices or implants, drug delivery, and edible pharmaceutical or food labels.

Example 9

Rapid Transfer-Based Micro Patterning and Dry Etching of Silk Microstructures ("STAMP")

Over the last two decades silk produced by the silkworm *Bombyx mori* has found new utility as a sustainable material platform for high-technology applications encompassing photonics, electronics and optoelectronics [1-4]. Silk fibers have been used as an FDA approved medical suture material for decades [5] due to their biocompatibility and mechanical properties [6]. These properties, along with the inherent biodegradability of silk, has driven the use of this protein for biological studies [6]. Native silk fibers can be solubilized and reprocessed into an aqueous silk fibroin protein solution [7], which can then be used to generate a multitude of new material formats [5] such as hydrogels [8], foams [9], electrospun mats [10] and sponges [11]. These new forms of silk are finding utility in drug delivery, cell culture and tissue engineering applications. Silk films with excellent optical properties (>90% transmission in the visible spectrum) [12] are currently being explored for applications in optics and biophotonics [3, 4]. Additionally, the environmentally benign, all-aqueous processing conditions and the chemistry of silk allow bioactive components, such as enzymes to be stabilized in the protein matrix [13].

Due to the excellent mechanical properties [14], micro- and nano patterning of silk films can be achieved across a wide range of feature sizes. Nanoimprinting and nano-casting [4, 15] techniques have been used to pattern silk films for photonic applications [16].

These films possess useful properties that allow interfacing with metals and thin-film semiconductor devices, and the opportunity to develop biocompatible hybrid silk devices. This was recently demonstrated by using silk-based electrodes to measure neural activity in-vivo [17]. Additionally, microfabricated metamaterial (MM) silk composites were demonstrated, with electromagnetic resonance responses in the THz frequency regime, with potential applications for in vivo bio sensors [18].

Device manufacturing with this protein would benefit from fabrication methods that simplify patterning techniques by avoiding prolonged times of sample preparation, elevated temperature or high vacuum [18], which, aside from providing more complexity, would also limit the use of biologically active species [13].

In this communication, we report a simple fabrication technique, which in a single step transfers metal micro patterns to free standing silk films under ambient processing conditions. We refer to this process as "Silk Transfer Applied Micro Pattering" or STAMP for short. Additionally, this method adds versatility and utility to silk protein device fabrication by allowing the use of the patterned films as hard masks for oxygen based reactive ion etching (RIE). RIE is a widely used tool for versatile and high throughput micro- and nano patterning. However, its utility for biopolymers is limited [19] due in part to the lack of convenient methods to apply etching masks to biopolymer films.

FIG. 9 illustrates the fabrication process that allows the direct transfer of microscale patterns onto the surface of the silk film. The effectiveness of the technique is demonstrated by manufacturing large-area silk film-based THz metamaterial (MM) structures composed of split-ring resonators (SRR) made with aluminum (Al) or gold (Au) at ambient pressure and temperature. The THz MM SRR structures employed have been described previously [18, 20]. Silicon (Si) wafers were first treated with a silanizing agent in order to reduce the adhesion of the metal to the Si surface and allow for easy pattern transfer to the silk film. Microscale patterns were deposited on the Si wafer either by using standard photolithography techniques or, alternatively, with a shadow masking approach [18].

Once the patterning step is complete, aqueous silk solution can be applied onto the patterned Si wafer. The silk solution was allowed to dry overnight to self-assemble and form a free-standing silk film, as previously described [21]. During the drying process silk binds to the metallic pattern on the surface causing the metal patterns to be transferred from the wafer onto the silk film. The exact molecular mechanisms underlining the observed adhesion between the metal patterns and the silk films is unclear. Among possible explanations is the presence of Cysteine (Cys)- and Tyrosine (Tyr) residues (a total of 8 Cys and 55 Tyr amino acids are present in the silk macromolecule [22]), which would affect the surface energy properties of the films, thereby favoring either thiol bonds of the Cys with Au [23] or interactions of Al-oxides with the hydroxyl groups on the Tyr residues [24, 25].

Figure 20:
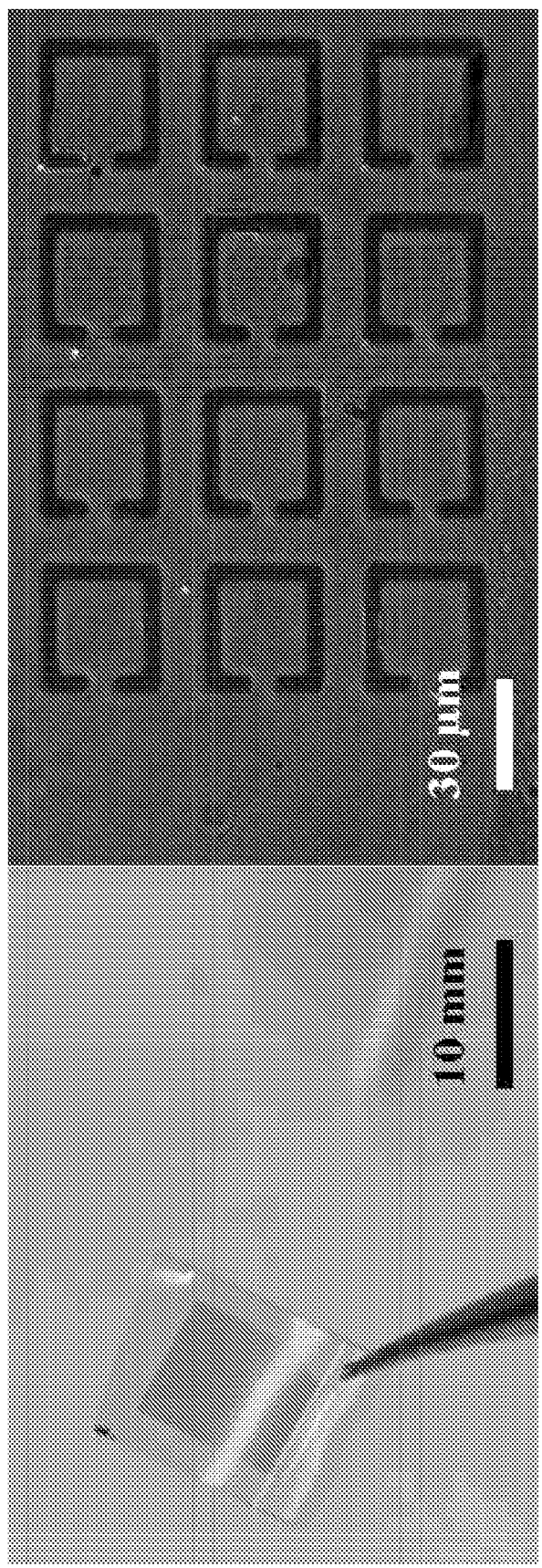
FIG. 20.

The silanization treatment prevents the silk film from adhering to the Si wafer surface and allows for its manual detachment from the substrate. Once this process is completed, the structures were examined by optical- and scanning electron microscopy (SEM) to verify successful transfer with high-fidelity on the microscale. The MM structures obtained in the STAMP process are shown in FIG. 20B which illustrates a free-standing micro patterned silk film. The transparent film was fabricated under ambient conditions and has a consistent smooth surface and thickness across the approximately 8 mm×8 mm patterned area. FIG. 20C shows an optical transmission micrograph of an Al MM patterned silk film. The critical dimensions in this SRR design are approximately 3 µm. The features of the SRR structures are found to be consistently maintained during the detachment process. In addition to the facile processing of a large-area free-standing silk based MM, it is worth pointing out that all of the processes described above are carried out under ambient conditions. This is particularly important since the activity of biological dopants, such as enzymes or antibodies, is preserved when they are incorporated in the silk matrix [13]. In order to manufacture hybrid systems with biochemical functionality in the silk films (e.g., pharmaceuticals [26]), the use of ambient temperature and ambient-pressure fabrication processes is important in order to maintain the bioactivity of these compounds. With this method, desired patterns of arbitrary complexity can be fabricated on a separate substrate and subsequently transferred onto the biologically doped silk film, under processing conditions that can preserve biological function.

To further demonstrate the convenience of the approach and the suitability of RIE as a manufacturing tool for silk micro- and nano patterning, we used the previously manufactured MM SRR structures as a mask for silk-RIE (FIG. 10). The previously transferred metal patterns provided a hard mask for the subsequent RIE step (FIG. 10A). For this approach we used our smallest size SRR arrays which had feature dimensions of approximately 1.5 µm at the gap, and a line width of the metal forming the resonator equal to 4 µm. The structures obtained from the etching process closely represent the SRR pattern in silk with the metal patterns still present on the etched film surface. In addition, the electromagnetic response of the etched structures was measured to demonstrate functionality of the MM silk composite structures and to illustrate fabrication consistency over the sampled region. FIG. 11B shows a SEM image of the Al MM mask and RIE etched structures. FIG. 11C shows the SEM image of an array of resonators from the RIE-silk film, the structure featured in FIG. 11B. As can be seen in FIG. 11C, the silk features produced with the STAMP method followed by RIE processing were consistent over the 100× 100 SRR array. FIG. 12D shows an SEM image of Au patterned SRR and RIE etched silk structures. These patterns were fabricated on the Si substrate with a previously described shadow masking technique [18]. The critical feature size in this SRR design was approximately 6 µm at the gap of the resonator. The features fabricated with the Au shadow masking technique were of comparable quality to traditional lithography fabricated features. Considerable difference was observed between RIE processed silk surfaces depending on the metal used. The Au coated specimens showed rough "grassy" surface structures (insert in FIG. 12D) in contrast to the smoother surfaces observed with the Al masked samples. We attribute the "grassy" surface structure to secondary Au micro masking, which can occur during RIE processing when using masking materials with a low sputtering threshold or a high sputtering yield, such as Au [27]. We chose Al as a mask material for the RIE processing step because of the Al-oxide formation caused when the sample is exposed to oxygen plasma. Such oxides have excellent resistance to sputtering and are less apt to induce micro masking effects and are therefore an excellent masking material for polymers. FIG. 12E shows an SEM micrograph of the etched wall profile of an Al masked sample. The etch depth was approximately 10 µm with vertical sidewalls, indicating the anisotropic nature of the silk dry etching process. As expected, the unmasked surfaces were found to be smooth and showing little residue. We hypothesize that the few features which can be seen on the etch floor in FIG. 12D could be attributed to dissimilar etching rates within the protein itself where the backbone would etch at slower rates than the bulk of the silk material because of its more stable structure [22].

Further demonstration of the quality of the etching process and the associated critical dimensions of the resulting structure was provided by measuring the electromagnetic response of the etched Al-MM structures (FIG. 13). The electromagnetic transmission spectrum corresponds to the Al MM structures shown in FIG. 11B and FIG. 11C. The samples were analyzed by terahertz time-domain spectroscopy (THz-TDS) as previously described [28]. A strong resonance response was detected right below 1 THz, indicating the functionality and integrity of the structures after the RIE processing. The THz beam was directed at the center of an 8 mm×8 mm RIE-etched MM patterned area, probing the resonance response and verify the consistency for two orthogonal polarizations. The MM resonance response is especially sensitive to changes in the SRRs structural dimensions, indicating even slight variation in manufacturing tolerances. We found from statistical analysis (Pearson correlation test) that the effect of the electromagnetic frequency on the transmission did not vary for the two polarizations (correlation coefficient $r > 0.99$, $p < 0.001$), indicating excellent symmetry of the structures and corroborating fabrication consistency. We also expect that RIE processed silk-MM sensors could potentially improve sensitivity in comparison to previously fabricated two dimensional structures, because of increased surface area and increased dielectric contrast of the etched three dimensional relief silk structures [18].

In conclusion, we have successfully transferred microfabricated patterns to silk biopolymer films under ambient processing conditions by employing a rapid transfer-based micro patterning technique. This method allows parallel fabrication of microstructures on large area, free standing and flexible silk films with high precision and eliminating the need for alignment. We have also demonstrated the use of this technique with various materials as masks for silk biopolymer RIE processing and a variety of SRR MM designs. This approach allows large area fabrication and is amenable to the transfer of different materials beyond metals. Additionally, individual feature sizes can be scaled to larger sizes to manufacture, for instance, metallic electrodes on silk films, or scaled down to the nanoscale for applications in photonic and plasmonic sensor systems [15].

Silk Extraction and Purification

The process to obtain aqueous silk fibroin solution from B. mori cocoons was previously described [7]. Briefly, sericin was removed by boiling the cocoons in an aqueous sodium carbonate solution for 30 minutes. After drying, the fibroin fibers were dissolved in a lithium bromide solution and subsequently the salt was removed by dialysis against deionized water (DI) until the solution reached a concentration of about 8-10% wt/v. To enhance the purity of the silk, we centrifuged a second time and filtered the solution through a 5 μm syringe filter (5 μm pore size, Millipore Inc, Bedford, Mass.) [29].

STAMP Process

A conventional 4" Si wafer (Nova wafers) was treated with the silanizing agent tridecafluoro-1,1,2,2-tetrahydrooctyl trichlorosilane (FOTS) to reduce sticking of the microfabricated features to the wafer during the transfer process. The Si wafer was placed in a vacuum chamber under house vacuum with a few drops of the FOTS solution to evaporate for approximately 24 hours. Subsequently, a thin layer (between 100 nm and 300 nm) of Al or Au was sputtered onto the FOTS treated Si wafer and standard photolithography was performed with S1813 photoresist (Rohm & Haas). Residual metal was wet etched in an appropriate etching solution and the remaining photoresist was removed, revealing the desired metal patterns. The MM design and mask was used from a previous study [20]. Approximately, 2 ml of 8% wt/v silk solution was evenly distributed over the whole wafer surface and allowed to dry at room temperature over night. The silk film with the transferred patterns was removed from the wafer surface with the help of a razor blade and tweezers.

RIE

The oxygen RIE process was performed in a custom made research RIE tool [30]. The patterned silk samples were mounted with double sided adhesive cupper tape (Ted Pella) to the cooled chuck to ensure proper thermal conductivity during the subsequent RIE step. The RIE processing conditions were 20 W plate power, <6 pTorr base pressure and 20 minutes processing time.

REFERENCES

[1] C. Li, C. Vepari, H. Jin, H. Kim, D. Kaplan, *Biomaterials* 2006, 27, 3115.
[2] G. H. Altman, F. Diaz, C. Jakuba, T. Calabro, R. L. Horan, J. S. Chen, H. Lu, J. Richmond, D. L. Kaplan, *Biomaterials* 2003, 24, 401.
[3] S. Parker, P. Domachuk, J. Amsden, J. Bressner, J. Lewis, D. Kaplan, F. Omenetto, *Advanced Materials* 2009.
[4] H. Perry, A. Gopinath, D. Kaplan, L. Dal Negro, F. Omenetto, 2008.
[5] F. Omenetto, D. Kaplan, *Science* 2010, 329, 528.
[6] G. H. Altman, F. Diaz, C. Jakuba, T. Calabro, R. L. Horan, J. Chen, H. Lu, J. Richmond, D. L. Kaplan, *Biomaterials* 2003, 24, 401.
[7] S. Sofia, M. B. McCarthy, G. Gronowicz, D. L. Kaplan, *Journal of Biomedical Materials Research* 2001, 54, 139.
[8] U. Kim, J. Park, C. Li, H. Jin, R. Valluzzi, D. Kaplan, *Biomacromolecules* 2004, 5, 786.
[9] D. Kang, D. Xu, Z. Zhang, K. Pal, D. Bang, J. Kim, *Macromolecular Materials and Engineering* 2009, 294, 620.
[10] H. Jin, J. Chen, V. Karageorgiou, G. Altman, D. Kaplan, *Biomaterials* 2004, 25, 1039.
[11] G. Chang, H. Kim, D. Kaplan, G. Vunjak-Novakovic, R. Kandel, *European Spine Journal* 2007, 16, 1848.
[12] B. Lawrence, M. Cronin-Golomb, I. Georgakoudi, D. Kaplan, F. Omenetto, *Biomacromolecules* 2008, 9, 1214.
[13] S. Lu, X. Wang, Q. Lu, X. Hu, N. Uppal, F. Omenetto, D. Kaplan, *Biomacromolecules* 2009, 217.
[14] C. Jiang, X. Wang, R. Gunawidjaja, Y. Lin, M. Gupta, D. Kaplan, R. Naik, V. Tsukruk, *Advanced functional materials* 2007, 17, 2229.
[15] J. Amsden, H. Perry, S. Boriskina, A. Gopinath, D. Kaplan, L. Dal Negro, F. Omenetto, *Optics Express* 2009, 17, 21271.
[16] F. Omenetto, D. Kaplan, *Nature Photonics* 2008, 2, 641.
[17] D. Kim, J. Viventi, J. Amsden, J. Xiao, L. Vigeland, Y. Kim, J. Blanco, B. Panilaitis, E. Frechette, D. Contreras, *Nature Materials* 2010, 9, 511.
[18] H. Tao, J. Amsden, A. Strikwerda, K. Fan, D. Kaplan, X. Zhang, R. Averitt, F. Omenetto, *Advanced Materials* 2010, 22.
[19] M. Lei, Y. Gu, A. Baldi, R. Siegel, B. Ziaie, *Langmuir* 2004, 20, 8947.
[20] H. Tao, N. Landy, C. Bingham, X. Zhang, R. Averitt, W. Padilla, *Opt. Lett* 2007, 32, 53.
[21] H. Jin, J. Park, V. Karageorgiou, U. Kim, R. Valluzzi, P. Cebe, D. Kaplan, *Advanced Functional Materials* 2005, 15, 1241.
[22] C. Zhou, F. Confalonieri, M. Jacquet, R. Perasso, Z. Li, J. Janin, *Proteins: Structure, Function, and Bioinformatics* 2001, 44, 119.
[23] C. Bain, E. Troughton, Y. Tao, J. Evall, G. Whitesides, R. Nuzzo, *Journal of the American Chemical Society* 1989, 111, 321.
[24] A. Murphy, P. John, D. Kaplan, *Biomaterials* 2008, 29, 2829.
[25] H. She, D. Malotky, M. Chaudhury, *Langmuir* 1998, 14, 3090.
[26] E. Pritchard, A. Wilz, T. Li, J. Lan, D. Boison, D. Kaplan, "Sustained-release silk biomaterials for drug delivery and tissue engineering scaffolds", presented at *Bioengineering Conference, 2009 IEEE 35th Annual Northeast*, 2009.
[27] D. Sameoto, Y. Li, C. Menon, *Advances in Science and Technology* 2009, 54, 439.
[28] S, Nishizawa, K. Sakai, M. Hangyo, T. Nagashima, M. Takeda, K. Tominaga, A. Oka, K. Tanaka, O. Morikawa, *Terahertz Optoelectronics* 2005, 203.
[29] H. Perry, Gopinath, A., Kaplan, D. L., Negro, L. D. & Omenetto, F. G., *Advanced Materials* 2008, In Press (2008).
[30] N. Forgotson, V. Khemka, J. Hopwood, Journal of Vacuum Science & Technology B: Microelectronics and Nanometer Structures 2009, 14, 732.

Example 10

THz Silk Metamaterials

In some embodiments, silk metamaterial composites of the invention are capable of modulating an incident electromagnetic radiation. In one embodiment, provided herein is a large-area silk metamaterial composite having metametarial structures patterned on free-standing biocompatible silk films showing strong resonance responses at terahertz frequencies. For example, FIG. 15 shows exemplary silk metamaterial composites of the invention and their different frequency responses in the terahertz regime. This discovery provides possibilities for fabrication of bioelectric and biophotonic devices integrating the metamaterial structures. For example, silk metamaterial composites which are resonant at the terahertz frequency regime may be used for identification and bio-sensing, as numerous chemical and biological agents show unique "fingerprints" at the THz regime. See Tao et al., Opt. Express, 16: 7181 (2008); O'Hara et al., Opt. Express, 16: 1786 (2008); Barber et al., J. Phys. Chem. A., 109: 3501 (2005).

By geometrically scaling the silk metamaterial composite design implemented in THz frequencies, the application of the designed silk metamaterial composite and devices comprising thereof can be applicable at a wide range of frequencies. This can encompass megahertz frequency regime to pecohertz frequency regime: the resonance frequency of the silk metamaterial composite may corresponds to a microwavelength, an infrared wavelength, a visible wavelength, or an ultraviolet wavelength. Scaling the silk metamaterial structure implemented at THz regime to a smaller dimension can enable the application of the material in a shorter wavelength, a visible wavelength, or even an ultraviolet wavelength, as long as the smaller sizes of the metamaterial elements can be fabricated.

Since silk films are optically transparent, it is possible to create a new collection of optical elements such as lenses and diffractive gratings, by 2D and/or 3D patterning of the silk films. See Omenetto & Kaplan, Nature Photon., 2: 641 (2008); Perry et al., Adv. Mater., 20: 3070-72 (2008). Furthermore, silk fibroin has been proven to be a biologically favorable carrier that enables bio-dopants such as enzymes and proteins to maintain their functionality. See Lawrence et al., Biomacromolecules, 9: 1214-20 (2008); Demura et al., J. Biotechnol., 10: 113 (1989). Additionally, the biodegradability of silk allows the devices to be implanted in human body where it can be resorbed and re-incorporated without the need for retrieval of the device after use. The versatile properties of silk allow for the creation of a new class of biophotonic devices that could be implanted into the human body to monitor interactions between specific targets and embedded dopants.

In addition to manipulating the silk films and embedding appropriate dopants, it is desirable to incorporate resonant electromagnetic structures with the silk films. In one embodiment, the invention thus provides an implantable device comprising a silk metamaterial composite comprising an array of metamaterial elements, disposed on or embedded in a silk matrix. As described above, the resonant electromagnetic structure of the silk metamaterial composite has a resonant response to the incident electromagnetic radiation therefore modulating the electromagnetic radiation. This enables hybrid silk-based sensors that couple biofunctionality with an easily measured electromagnetic response that changes in response to the local environment. The exemplary metamaterial elements and components of silk metameterial composites have been described herein in the above embodiments.

Example 11

Implantable Devices

In some embodiments, the present invention provides, for example, implantable devices that act as a biosensing device or a biodetecting device. Such an implantable device may further comprise one or more dopants that may be any active agents as described herein in the above embodiments. The dopants (or active agents) may be incorporated in the device through blending into the silk matrix. The dopants may or may not further interfere with the structure and properties of metamaterial elements or interfere with the modulation of electromagnetic properties of the silk metamaterials. For example, the dopants may change dielectric properties of silk metamaterial thereby changing the intensity/amplitude of the transmitted, reflected and absorbed waves, and/or the resonance frequency of the silk metamaterials.

Example 12

Conformable Devices

In some embodiments, the present invention provides devices (e.g., bio-integrated devices, such as an implantable medical device), which has a large fraction of the device flexible to easily conform to the surface of a subject to be contacted with the implantable medical device. For example, the device may be fabricated from an ultrathin silk metamaterial composite, where both the conductive metamaterial elements and silk matrix are ultrathin and flexible. Such implantable devices can hence form conformal contact with the curvilinear surfaces of various organs or tissues.

Conformal contact of a bio-integrated device comprising a silk metamaterial composite with a subject may be realized by contacting the device with aqueous solution, or a wet surface of the subject. In this regard, the silk matrix in the silk metamaterial composite of this embodiment is at least partially dissolvable upon contact with the aqueous solution or the wet surface, so as to enable the conformal contact of the implantable device with the surface of the subject to be contacted with the implantable medical device. Silk film herein is typically, for instance, no more than 100 µm, up to 75 µm, up to 25 µm, up to 7 µm, up to 2.5 µm, or up to 1 µm, to enable the fast dissolution upon contact with the aqueous solution or wet surface.

In some embodiments, the design of a bio-integrated device comprising the silk metamaterial composite has a large fraction of the device soluble and/or biodegradable. Hence the device will disappear or resorb, over time. A sufficiently small amount of the device may remain; however, the use of noble metals in small quantities renders the devices perfectly biocompatible and any biological response induced from the remaining material is usually negligible.

Example 13

Fabrication of Certain Silk Electronic Components Comprising Patterned Metal Structures on a Silk Matrix In some aspects, the present invention relates to a method of fabricating a silk metamaterial composite having resonant electromagnetic properties. In some embodiments, the method comprises the steps of contact-positioning a shadow mask on to a silk substrate; and spray-depositing a conductive material on a silk substrate through the shadow mask thereby forming an array of metamaterial elements on the silk substrate. The shadow mask provides a desired geometry (e.g., the structural feature of metamaterial elements and/or patterns for the array of metamaterial elements) for the metamaterial structures and metamaterial elements that define the resonant electromagnetic properties of the silk metamaterial composites. Any advantage of this progress lies in the flexibility offered using large area stencil-based deposition in conjunction with available soft fabrication techniques for processing silk films. These features, and others, allow for the development of novel flexible electronics and optics on silk substrates.

The microfabrication of metamaterial structures on silk films can be different when compared to patterning on other widely used substrates such as silicon and PDMS. To prevent possible contamination of the silk substrate while maintaining its bio-compatibility, the silk films are typically prevented from exposure to photoresist (PR) and chemical solutions such as acetone and PR developers, which are normally used for typical lithography-based metal patterning process.

A shadow mask metal patterning fabrication process may be used to fabricate silk metamaterial composite. The patterning is generally based on selective deposition of a target material through a micro/nano stencil-based shadow mask. See Cord et al., J. Vac. Sci. Technol. B, 24: 3139 (2006), which is incorporated herein by reference in its entirety.

The metamaterial structures may be sprayed directly on the silk films through the designed geometry of microfabricated stencils. The entire fabrication process may be conducted in a dry, chemical-free environment to assist in preventing any possible contamination that might be involved in other photolithography-based metal patterning methods, such as lift-off processes and wet-etching. Such methods help in maintaining the integrity and biocompatibility of the silk films while not adversely affecting the silk film, i.e., silk film after processing can still present high transparency at THz frequencies, and hence the silk metamaterial composites display a strong resonant electromagnetic response. The as-fabricated samples are suitable for incorporation into biological environments such as the human body for bio-tracking purposes by monitoring the resonance response behavior of the metamaterials. See Kim et al., Rogers, *Appl. Phys. Leh.*, 95: 133701 (2009), which is incorporated herein by reference in its entirety.

The shadow mask may be attached to the silk substrate in contact mode, i.e., the shadow mask is placed in contact with silk substrate and is aligned and positioned with respect to silk substrate without using additional adhesives between the shadow mask and silk substrate. The shadow mask can be removed freely after spraying the metal layers, without using additional solvents or treatments. Conductive material may be deposited on silk substrate through an evaporation source, e.g., evaporated through the openings of the shadow mask onto the silk substrate. Any known means of metal evaporations can be used herein, including, for instance, electron beam evaporation or thermal evaporation. Optionally, the evaporation process may be repeated with different conductive materials and/or different shadow mask designs to create multi-layered micropatterning.

To accurately position or fix the shadow mask relative to the silk substrate during the spraying process, the shadow mask may be aligned with the silk substrates under microscopy and the edges of the shadow mask may be attached tightly to the silk substrates with tapes. After the spraying, the shadow mask can then be removed by peeling off the tape and releasing the as-sprayed silk substrates. Otherwise, an adhesive can be used to attach the shadow mask to the silk substrate, which also typically involves the additional step of removing the adhesive afterwards with a solvent, as known in the art.

The spray-depositing technique through shadow mask as used in this invention typically utilizes the high degree of flatness of the substrates upon which conductive materials are deposited. Such approach is quite suitable for silk films, as the silk films exhibit sufficient flatness over large areas resulting from the all-aqueous processing of the protein. This property of silk film facilitates the direct spraying of large-area metallic and/or non-metallic patterns with good uniformity onto the silk films. The fabrication process could be readily adopted to fabricate silk metamaterial composites at wide range of wavelengths in electromagnetic spectrum, e.g., from the microwave to visible. For example, the technique for making the micro-stencils could be easily modified for making nano-stencils by switching from standard UV photolithography to electron-beam writing for much smaller features down to tens of nanometers. As such, the method of the invention can be used for fabricating devices for in-situ bio-sensing with implanted medical devices to covert tracking with biodegradable silk/metamaterial beacons. See Padilla et al., Phys. Rev. B, 75: 041102R (2007); Tao et al., J. Phys. D: Appl. Phys., 41: 232004 (2008).

The spray-depositing technique through shadow mask in contact mode with silk matrix has virtually no requirements on the sprayed patterns. Nevertheless, certain patterns may be difficult to be directly deposited on the silk matrix in contact mode, for instance, isolated patterns with no connecting paths to the stencil supporting frame such as features inside other closed patterns. In this regard, appropriate compensation strategies may be used. See, e.g., Apanius et al., Sensor Actuat. A: Phys., 140: 168 (2007).

Other Embodiments

It should be understood that this invention is not limited to the particular methodology, protocols, and reagents, etc., described herein and as such may vary. The terminology used herein is for the purpose of describing particular embodiments only, and is not intended to limit the scope of the invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

We claim:

1. A silk electronic component comprising:
   a silk matrix; and
   a plurality of conductive metamaterial elements that are coupled to the silk matrix,
   wherein elements of the plurality of conductive metamaterial elements are arranged in an array to form at least one patterned structure, and
   wherein at least one dimension of the structure is smaller than a wavelength of incident electromagnetic radiation so that, when the silk electronic component is exposed to the electromagnetic radiation, the radiation is modulated such that the silk electronic component exhibits a subwavelength resonant electromagnetic response.

2. The silk electronic component of claim 1, wherein the silk matrix has a surface roughness of less than 5 nm.

3. The silk electronic component of claim 1, wherein the silk matrix comprises silk fibroin.

4. The silk electronic component of claim 1, wherein the silk matrix is a film, hydrogel, foam, e-gel or microsphere.

5. The silk electronic component of claim 1, wherein the silk matrix comprises a dopant.

6. The silk electronic component of claim 5, wherein the dopant is a pharmaceutical, antibody, fragment or portion of an antibody, antibiotic, enzyme, organic indicator, photoactive dye, cell, protein, peptide, nucleic acid analogue, nucleotide, oligonucleotide, peptide nucleic acid, aptamer, hormone, hormone antagonist, growth factor, fragment of a growth factor, variant of a growth factor, recombinant growth factor, fragment of a recombinant growth factor, variant of a recombinant growth factor, cytokine, antimicrobial compound, virus, antiviral, toxin, prodrug, drug, chemotherapeutic agent, small molecule, chromophore, light-emitting organic compound, light-emitting inorganic compounds, light-harvesting compound, light-capturing complex, or combinations thereof.

7. The silk electronic component of claim 5, wherein the dopant modulates the electromagnetic radiation.

8. The silk electronic component of claim 1, wherein the silk matrix conforms to a surface upon contact with the surface.

9. The silk electronic component of claim 1, wherein the silk matrix adheres to a surface upon contact with the surface.

10. The silk electronic component of claim 1, wherein a portion of the silk matrix dissolves upon contact with aqueous solution to adhere to a surface upon contact with the surface.

11. The silk electronic component of claim 1, wherein the patterned conductive structure is disposed on a surface of the silk matrix.

12. The silk electronic component of claim 1, wherein the patterned conductive structure is embedded in the silk matrix.

13. The silk electronic component of claim 1, wherein the patterned conductive structure comprises a conductive material, wherein the conductive material optionally comprises gold, aluminum, chromium, silver, platinum, copper, titanium, nickel, rhodium, cobalt, iron, zirconium, molybdenum, palladium, hafnium, iridium, tungsten, tantalum, indium tin oxide (ITO), polysilicon, graphite, or any combination thereof.

14. The silk electronic component of claim 1, wherein the patterned conductive structure comprises a resonator, split-ring resonator, polarization-sensitive electric resonator, polarization non-sensitive electric resonator, radio-frequency identification (RFID) device, metamaterial structure, antenna, conductive coil, or any combination thereof.

15. The silk electronic component of claim 1, wherein the silk electronic component responds to microwave radiation, infrared radiation, visible radiation, ultraviolet radiation, or any combination thereof.

16. The silk electronic component of claim 1, wherein the silk electronic component responds to the electromagnetic radiation to exhibit an electromagnetic signature in the terahertz (THz) frequencies, megahertz (MHz) frequencies, gigahertz (GHz) frequencies, petahertz (PHz) frequencies, or any combination thereof.

17. The silk electronic component of claim 1, wherein the silk electronic component responds to the electromagnetic radiation to exhibit an electromagnetic signature, the electromagnetic signature comprising a resonance response.

18. The silk electronic component of claim 1, wherein the silk electronic component modulates the electromagnetic radiation.

19. The silk electronic component of claim 1, wherein the plurality of conductive metamaterial elements that are coupled to the silk matrix conductive material comprise a metal.

20. The silk electronic component of claim 19, wherein the metal comprises copper, gold, silver, platinum, chromium, cobalt, aluminum, nickel, rhodium, titanium, magnesium, iron, zirconium, molybdenum, palladium, hafnium, iridium, tungsten, tantalum, and combinations thereof.

21. The silk electronic component of claim 19, wherein the non-metal comprises indium tin oxide (ITO), polysilicon, graphite, and combinations thereof.

22. The silk electronic component of claim 1, wherein the plurality of conductive metamaterial elements that are coupled to the silk matrix conductive material comprise a non-metal.

23. A method of fabricating a silk electronic component of claim 1, the method comprising:
    positioning a shadow mask on a silk matrix;
    depositing a metamaterial on the silk matrix through openings in the shadow mask; and
    removing the shadow mask from the silk matrix.

24. The method of claim 23, wherein depositing the metamaterial comprises spray-depositing the metamaterial.

25. The method of claim 23, wherein depositing the metamaterial comprises evaporating the metamaterial through the openings in the shadow mask.

26. A method of fabricating a silk electronic component of claim 1, the method comprising:
    depositing a conductive material in a pattern on a substrate;
    applying an aqueous silk solution over the substrate;
    drying the aqueous silk solution to form a silk matrix, the silk matrix encapsulating the conductive material as the silk matrix dries to form a silk metamaterial composite having at least one patterned conductive structure coupled to the silk matrix;
    detaching the silk metamaterial composite from the substrate; and
    wherein the silk metamaterial composite is characterized in that when the composite responds to electromagnetic radiation, the composite exhibits a resonant response.

27. The method of claim 26, further comprising etching a structure in the silk matrix according to the pattern of the conductive material.

* * * * *

SEQUENCE LISTING

<160> NUMBER OF SEQ ID NOS: 22

<210> SEQ ID NO 1
<211> LENGTH: 90
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (7)..(90)
<223> OTHER INFORMATION: Wherein any of residues 7-90 may be missing.

<400> SEQUENCE: 1

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
        35                  40                  45

Gly Ala Gly Ala Gly Ser Gly Ala Gly Ala Gly Ser Gly Ala Gly Ala
    50                  55                  60

Gly Ser Gly Ala Gly Ala Gly Ser Gly Ala Gly Ala Gly Ser Gly Ala
65                  70                  75                  80

Gly Ala Gly Ser Gly Ala Gly Ala Gly Ser
                85                  90

<210> SEQ ID NO 2
<211> LENGTH: 30
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Wherein X is V, I or A.
<220> FEATURE:
<221> NAME/KEY: MISC_FEATURE
<222> LOCATION: (3)..(30)
<223> OTHER INFORMATION: Wherein any of residues 3-30 may be missing
<220> FEATURE:
<221> NAME/KEY: MISC_FEATURE
<222> LOCATION: (4)..(4)
<223> OTHER INFORMATION: Wherein X is V, I or A.
<220> FEATURE:
<221> NAME/KEY: MISC_FEATURE
<222> LOCATION: (6)..(6)
<223> OTHER INFORMATION: Wherein X is V, I or A.
<220> FEATURE:
<221> NAME/KEY: MISC_FEATURE
<222> LOCATION: (8)..(8)
<223> OTHER INFORMATION: Wherein X is V, I or A.
<220> FEATURE:
<221> NAME/KEY: MISC_FEATURE
<222> LOCATION: (10)..(10)
<223> OTHER INFORMATION: Wherein X is V, I or A.
<220> FEATURE:
<221> NAME/KEY: MISC_FEATURE
<222> LOCATION: (12)..(12)
<223> OTHER INFORMATION: Wherein X is V, I or A.
<220> FEATURE:
<221> NAME/KEY: MISC_FEATURE
<222> LOCATION: (14)..(14)
<223> OTHER INFORMATION: Wherein X is V, I or A.
<220> FEATURE:
<221> NAME/KEY: MISC_FEATURE
<222> LOCATION: (16)..(16)
<223> OTHER INFORMATION: Wherein X is V, I or A.
<220> FEATURE:
<221> NAME/KEY: MISC_FEATURE

```
<222> LOCATION: (18)..(18)
<223> OTHER INFORMATION: Wherein X is V, I or A.
<220> FEATURE:
<221> NAME/KEY: MISC_FEATURE
<222> LOCATION: (20)..(20)
<223> OTHER INFORMATION: Wherein X is V, I or A.
<220> FEATURE:
<221> NAME/KEY: MISC_FEATURE
<222> LOCATION: (22)..(22)
<223> OTHER INFORMATION: Wherein X is V, I or A.
<220> FEATURE:
<221> NAME/KEY: MISC_FEATURE
<222> LOCATION: (24)..(24)
<223> OTHER INFORMATION: Wherein X is V, I or A.
<220> FEATURE:
<221> NAME/KEY: MISC_FEATURE
<222> LOCATION: (26)..(26)
<223> OTHER INFORMATION: Wherein X is V, I or A.
<220> FEATURE:
<221> NAME/KEY: MISC_FEATURE
<222> LOCATION: (28)..(28)
<223> OTHER INFORMATION: Wherein X is V, I or A.
<220> FEATURE:
<221> NAME/KEY: MISC_FEATURE
<222> LOCATION: (30)..(30)
<223> OTHER INFORMATION: Wherein X is V, I or A.

<400> SEQUENCE: 2

Gly Xaa Gly Xaa Gly Xaa Gly Xaa Gly Xaa Gly Xaa Gly Xaa Gly Xaa
1               5                   10                  15

Gly Xaa Gly Xaa Gly Xaa Gly Xaa Gly Xaa Gly Xaa Gly Xaa
            20                  25                  30

<210> SEQ ID NO 3
<211> LENGTH: 4
<212> TYPE: PRT
<213> ORGANISM: Bombyx mori

<400> SEQUENCE: 3

Gly Ala Ala Ser
1

<210> SEQ ID NO 4
<211> LENGTH: 15
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Wherein residue S may be missing
<220> FEATURE:
<221> NAME/KEY: MISC_FEATURE
<222> LOCATION: (14)..(15)
<223> OTHER INFORMATION: Wherein any of residues 14-15 may be missing

<400> SEQUENCE: 4

Ser Ser Ala Ala Ala Ala Ala Ala Ala Ala Ala Ala Ala Ala Ala
1               5                   10                  15

<210> SEQ ID NO 5
<211> LENGTH: 8
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(5)
<223> OTHER INFORMATION: Wherein any of residues 2-5 may be missing
<220> FEATURE:
```

```
<221> NAME/KEY: MISC_FEATURE
<222> LOCATION: (2)..(2)
<223> OTHER INFORMATION: Wherein X is any residue
<220> FEATURE:
<221> NAME/KEY: MISC_FEATURE
<222> LOCATION: (3)..(3)
<223> OTHER INFORMATION: Wherein X is any residue
<220> FEATURE:
<221> NAME/KEY: MISC_FEATURE
<222> LOCATION: (4)..(4)
<223> OTHER INFORMATION: Wherein X is any residue
<220> FEATURE:
<221> NAME/KEY: MISC_FEATURE
<222> LOCATION: (5)..(5)
<223> OTHER INFORMATION: Wherein X is any residue
<220> FEATURE:
<221> NAME/KEY: MISC_FEATURE
<222> LOCATION: (8)..(8)
<223> OTHER INFORMATION: Wherein X is any residue

<400> SEQUENCE: 5

Gly Xaa Xaa Xaa Xaa Gly Gly Xaa
1               5

<210> SEQ ID NO 6
<211> LENGTH: 4
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (4)..(4)
<223> OTHER INFORMATION: Wherein X is A, S, Y, R, D, V or W

<400> SEQUENCE: 6

Gly Gly Gly Xaa
1

<210> SEQ ID NO 7
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Wherein residue S may be missing
<220> FEATURE:
<221> NAME/KEY: MISC_FEATURE
<222> LOCATION: (4)..(6)
<223> OTHER INFORMATION: Wherein any residues 4-6 may be missing

<400> SEQUENCE: 7

Ser Ser Ala Ala Ala Ala Ser Ser Ala Ala Ala Ala
1               5                   10

<210> SEQ ID NO 8
<211> LENGTH: 6
<212> TYPE: PRT
<213> ORGANISM: Galleria mellonella

<400> SEQUENCE: 8

Gly Leu Gly Gly Leu Gly
1               5

<210> SEQ ID NO 9
<211> LENGTH: 6
<212> TYPE: PRT
<213> ORGANISM: Artificial sequence
```

```
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Wherein X is L, I, V or P
<220> FEATURE:
<221> NAME/KEY: MISC_FEATURE
<222> LOCATION: (5)..(5)
<223> OTHER INFORMATION: Wherein X is L, I, V or P

<400> SEQUENCE: 9

Gly Xaa Gly Gly Xaa Gly
1               5

<210> SEQ ID NO 10
<211> LENGTH: 21
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (5)..(5)
<223> OTHER INFORMATION: Wherein X is Y, V, S or A
<220> FEATURE:
<221> NAME/KEY: MISC_FEATURE
<222> LOCATION: (6)..(20)
<223> OTHER INFORMATION: Wherein any of 6-20 may be missing
<220> FEATURE:
<221> NAME/KEY: MISC_FEATURE
<222> LOCATION: (10)..(10)
<223> OTHER INFORMATION: Wherein X is Y, V, S or A
<220> FEATURE:
<221> NAME/KEY: MISC_FEATURE
<222> LOCATION: (15)..(15)
<223> OTHER INFORMATION: Wherein X is Y, V, S or A
<220> FEATURE:
<221> NAME/KEY: MISC_FEATURE
<222> LOCATION: (20)..(20)
<223> OTHER INFORMATION: Wherein X is Y, V, S or A

<400> SEQUENCE: 10

Gly Pro Gly Gly Xaa Gly Pro Gly Gly Xaa Gly Pro Gly Gly Xaa Gly
1               5                   10                  15

Pro Gly Gly Xaa Tyr
            20

<210> SEQ ID NO 11
<211> LENGTH: 5
<212> TYPE: PRT
<213> ORGANISM: Argiope trifasciata

<400> SEQUENCE: 11

Gly Arg Gly Gly Ala
1               5

<210> SEQ ID NO 12
<211> LENGTH: 13
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (5)..(10)
<223> OTHER INFORMATION: Wherein any of 5-10 may be missing

<400> SEQUENCE: 12

Gly Ala Gly Ala Ala Ala Ala Ala Ala Ala Gly Gly Ala
1               5                   10
```

-continued

```
<210> SEQ ID NO 13
<211> LENGTH: 8
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (3)..(3)
<223> OTHER INFORMATION: Wherein X is Q, Y, L, A, S or R
<220> FEATURE:
<221> NAME/KEY: MISC_FEATURE
<222> LOCATION: (5)..(5)
<223> OTHER INFORMATION: Wherein X is Q, Y, L, A, S or R
<220> FEATURE:
<221> NAME/KEY: MISC_FEATURE
<222> LOCATION: (7)..(7)
<223> OTHER INFORMATION: Wherein X is Q, Y, L, A, S or R
<220> FEATURE:
<221> NAME/KEY: MISC_FEATURE
<222> LOCATION: (8)..(8)
<223> OTHER INFORMATION: Wherein X is Q, Y, L, A, S or R

<400> SEQUENCE: 13

Gly Gly Xaa Gly Xaa Gly Xaa Xaa
1               5

<210> SEQ ID NO 14
<211> LENGTH: 16
<212> TYPE: PRT
<213> ORGANISM: Bombyx mori

<400> SEQUENCE: 14

Thr Gly Ser Ser Gly Phe Gly Pro Tyr Val Asn Gly Gly Tyr Ser Gly
1               5                   10                  15

<210> SEQ ID NO 15
<211> LENGTH: 8
<212> TYPE: PRT
<213> ORGANISM: Bombyx mandarina

<400> SEQUENCE: 15

Tyr Glu Tyr Ala Trp Ser Ser Glu
1               5

<210> SEQ ID NO 16
<211> LENGTH: 7
<212> TYPE: PRT
<213> ORGANISM: Antheraea mylitta

<400> SEQUENCE: 16

Ser Asp Phe Gly Thr Gly Ser
1               5

<210> SEQ ID NO 17
<211> LENGTH: 7
<212> TYPE: PRT
<213> ORGANISM: Antheraea yamamai

<400> SEQUENCE: 17

Arg Arg Ala Gly Tyr Asp Arg
1               5

<210> SEQ ID NO 18
<211> LENGTH: 8
<212> TYPE: PRT
<213> ORGANISM: Galleria mellonella
```

```
<400> SEQUENCE: 18

Glu Val Ile Val Ile Asp Asp Arg
1               5

<210> SEQ ID NO 19
<211> LENGTH: 18
<212> TYPE: PRT
<213> ORGANISM: Nephila madascariensis

<400> SEQUENCE: 19

Thr Thr Ile Ile Glu Asp Leu Asp Ile Thr Ile Asp Gly Ala Asp Gly
1               5                   10                  15

Pro Ile

<210> SEQ ID NO 20
<211> LENGTH: 8
<212> TYPE: PRT
<213> ORGANISM: Nephila clavipes

<400> SEQUENCE: 20

Thr Ile Ser Glu Glu Leu Thr Ile
1               5

<210> SEQ ID NO 21
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 21

Gly Ser Gly Ala Gly Ala
1               5

<210> SEQ ID NO 22
<211> LENGTH: 5
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (4)..(4)
<223> OTHER INFORMATION: Wherein X is any residue
<220> FEATURE:
<221> NAME/KEY: MISC_FEATURE
<222> LOCATION: (5)..(5)
<223> OTHER INFORMATION: Wherein X is any residue

<400> SEQUENCE: 22

Gly Pro Gly Xaa Xaa
1               5
```